United States Patent
Hackenberger et al.

(10) Patent No.: US 11,572,384 B2
(45) Date of Patent: Feb. 7, 2023

(54) UNUSUAL SUBSTRATES OF TUBULIN TYROSINE LIGASE

(71) Applicants: FORSCHUNGSVERBUND BERLIN E.V., Berlin (DE); LUDWIG-MAXIMILIANS-UNIVERSITÄT MÜNCHEN, Munich (DE)

(72) Inventors: Christian Hackenberger, Berlin (DE); Dominik Schumacher, Berlin (DE); Jonas Helma-Smets, Munich (DE); Heinrich Leonhardt, Munich (DE)

(73) Assignees: Forschungsverbund Berlin e.V., Berlin (DE); Ludwig-Mavimilians-Universität München, Munich (DE)

( * ) Notice: Subject to any disclaimer, the term of this patent is extended or adjusted under 35 U.S.C. 154(b) by 923 days.

(21) Appl. No.: 16/096,787

(22) PCT Filed: Apr. 27, 2017

(86) PCT No.: PCT/EP2017/060070
§ 371 (c)(1),
(2) Date: Oct. 26, 2018

(87) PCT Pub. No.: WO2017/186855
PCT Pub. Date: Nov. 2, 2017

(65) Prior Publication Data
US 2019/0144493 A1    May 16, 2019

(30) Foreign Application Priority Data

Apr. 28, 2016 (LU) .......................................... 93051
Mar. 7, 2017 (EP) ..................................... 17159594

(51) Int. Cl.
*C07K 1/107* (2006.01)
*C12P 21/02* (2006.01)

(52) U.S. Cl.
CPC ............ *C07K 1/1075* (2013.01); *C12P 21/02* (2013.01); *C12Y 603/02025* (2013.01)

(58) Field of Classification Search
None
See application file for complete search history.

(56) References Cited

FOREIGN PATENT DOCUMENTS

| WO | 2011150495 | * | 12/2011 |
| WO | 2011150495 | A1 | 12/2011 |
| WO | 2013003555 | A1 | 1/2013 |
| WO | 2015041729 | * | 3/2015 |
| WO | 2015041729 | A2 | 3/2015 |

OTHER PUBLICATIONS

Erck et al., Neurochemical Research, vol. 25, No. 1, 2000, pp. 5-10 (Year: 2000).*
Prota et al., J. Cell Biol. 2013;200:259-270 (Year: 2013).*
Kalisz et al., Biochimica Et Biophysica Acta. Protein Structure and Molecular Enzymology, Elsevier, Amsterdam; NL, vol. 1481, No. 1, Aug. 31, 2000 (Aug. 31, 2000), pp. 131-138 (Year: 2000).*

(Continued)

*Primary Examiner* — Karl J Puttlitz
(74) *Attorney, Agent, or Firm* — Seed IP Law Group LLP

(57) ABSTRACT

The present invention provides means and methods for functionalizing a polypeptide of interest at its C-terminus with an amino acid derivative.

Figure 1:
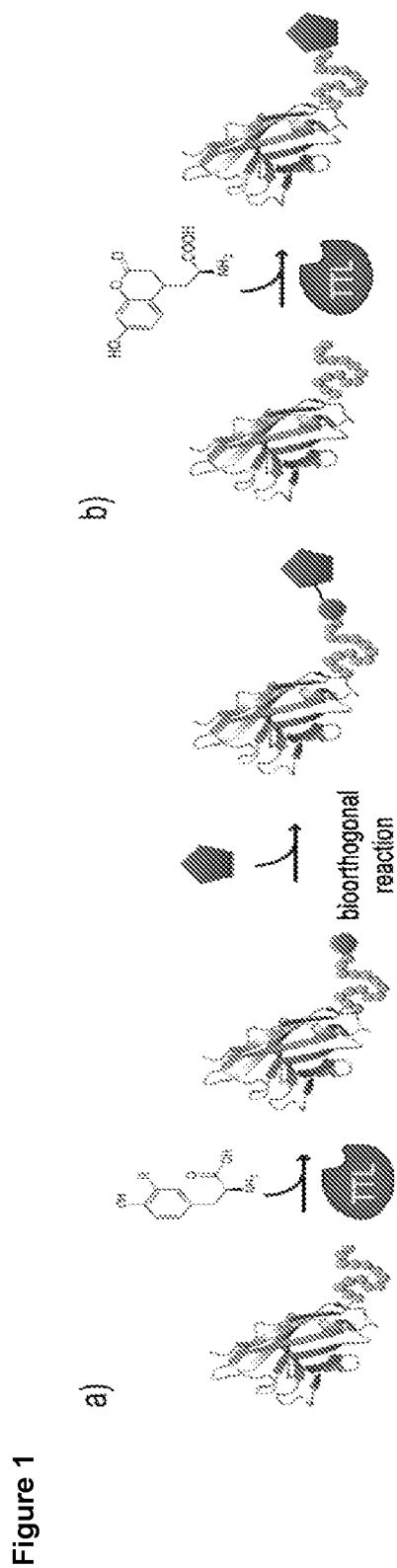

25 Claims, 11 Drawing Sheets
Specification includes a Sequence Listing.

(56) References Cited

OTHER PUBLICATIONS

Raybin et al., Biochemistry, Jan. 1, 1977 (Jan. 1, 1977), pp. 2189-2194 (Year: 1977).*
Banerjee et al., ACS Chem. Biol. 2010, 5, 8, 777-785 (Year: 2010).*
Ng et al., Org. Biomol. Chem., 2015,13, 374-378 (Year: 2015).*
Schumacher et al., Angew. Chem. Int. Ed. 2015, 54, 13787-13791 (Year: 2015).*
Raybin et al., Biochemistry, Jan. 1, 1977, vol. 16, No. 19, pp. 2189-2194.
Kalisz et al., Biochimica et Biophysica Acta, Aug. 31, 2000, vol. 1481, No. 1, pp. 131-138.
PCT International Search Report and Written Opinion dated Jul. 31, 2017 from corresponding Application No. PCT/EP2017/060070, 12 pages.
Hackenberger et al., Angewandte Chemie International Edition 47, 2008, pp. 10030-10074.
Szyk et al., Nature Struc. Mol. Biol., Nov. 2011, vol. 18, No. 11, pp. 1250-1259.
Prota et al., J. Cell. Bio., Jan. 28, 2013, vol. 200, No. 3, pp. 259-270.
Arce et al., Journal of Neurochemistry (1978), vol. 33, pp. 205-210.
Rudiger et al., Eur. J. Biochem 220, pp. 309-320 (1994), FEBS © 1994.
Banerjee et al., (2010), ACS Chemical Biology, vol. 5, No. 8, pp. 777-785.
Schumacher et al., Angew. Chem. Int. Ed. 2015, vol. 54, pp. 13787-13791.

\* cited by examiner

Figure 2

Coumarin

Coumarin

UNUSUAL SUBSTRATES OF TUBULIN TYROSINE LIGASE

BACKGROUND

Protein engineering has become a widely used tool in many areas of protein biochemistry. For example, protein fusion tags are indispensable tools used to improve recombinant protein expression yields, enable protein purification, and accelerate the characterization of protein structure and function. Solubility-enhancing tags, genetically engineered epitopes, and recombinant endoproteases have resulted in a versatile array of combinatorial elements that facilitate protein detection and purification. However, also protein modifications are of importance to study structure and function relationships.

Instead of the random labeling of amino acids, such as lysine residues, methods have been developed to (sequence) specific label proteins. Next to chemical modifications, tools to integrate new chemical groups for bioorthogonal reactions/modifications or chemoselective modifications have been applied. Alternatively, proteins can also be selectively modified by enzymes. By modifying existing amino acids or introducing non-natural amino acids, proteins can be manipulated at the single amino acid level. Several methods involving the site-specific modification of proteins have been reported in the last decade. This allows the spatial and temporal control of proteins in vivo, as well as single molecule tracking. Modifications are introduced during protein translation, as post translational modification or chemically, after protein isolation.

After translation, almost all proteins require post-translational modifications (PTMs) before becoming mature. The oxidation of cysteines is a common PTM and is important for protein folding and stability. Other PTMs increase the functional diversity of proteins by the modification of amino acids including phosphorylation, glycosylation, ubiquitination, nitrosylation, methylation, acetylation and proline cis-trans isomerization. Site-specific enzymatic PTMs are of particular interest since they can be used to manipulate and/or study proteins.

Examples for PTM are membrane associated modifications facilitated by farnesyl-and N-myristoyltransferases. In another approach the native formylglycine generating enzyme (FGE) is used to introduce formylglycine in both prokaryotes and eukaryotes. The aldehyde tagged protein can be readily functionalized with aminooxy- or hydrazide-functionalized biomolecules. Besides the modification of other proteins, some enzymes can be used for self-modification such as human O6-alkylguanine-DNA alkyl transferase (hAGT), cutinase and halo alkane dehalogenase.

A straightforward class of enzymes for modifying proteins after translation are the ligases. Biotin ligase (BirA) was shown to accept also a ketone isostere of biotin as a cofactor. Ligation of this biotin analog to proteins bearing the 15-amino-acid acceptor peptide (AP) was demonstrated in vitro and in vivo, followed by subsequent ketone-hydrazine conjugation. Second, the microbial lipoic acid ligase (LpIA) was used to specifically attach an alkyl azide onto proteins with an engineered LpIA acceptor peptide (LAP). Another ligase is the intein-based protein ligation system. A prerequisite for this intein-mediated ligation method is that the target protein is expressed as a correctly folded fusion with the intein, which may be challenging.

Another set of post-translational modifications is performed by phosphopantetheinyl transferases (PPTases). PPTases transfer a phosphopantetheinyl (P-pant) group through a phosphodiester bond onto peptidyl/acyl carrier protein (PCP/ACP) domains. These typically 80-120 residues long domains are present on nonribosomal peptide synthetases (NRPSs), polyketide synthases (PKSs), and fatty acid synthases (FASs). Interestingly, orthogonal fluorescent labeling of cell surface receptors was demonstrated by using the PPTases Sfp and AcpS selective peptide tags Instead of exploring the chemical space in which biomolecules can be modified by functional groups and subsequently incorporated in proteins of interest, some general applicable enzymatic modifications preexist in nature. Transpeptidation is, for example, catalyzed by sortases, a transpeptidase from Staphylococcus aureus, has emerged as a general method for derivatizing proteins with various types of modifications. For conventional sortase modifications, target proteins are engineered to contain a sortase recognition motif (LPXT) near their C-termini. When incubated with synthetic peptides containing one or more N-terminal glycine residues and a recombinant sortase, these artificial sortase substrates undergo a transacylation reaction resulting in the exchange of residues C-terminal to the threonine residue with the synthetic oligoglycine peptide, resulting in the protein C-terminus being ligated to the N-terminus of the synthetic peptide (WO 2013/003555).

Other techniques for protein engineering are based on chemoselective ligation and incorporation of modified amino acid residues which may serve as joint connection for the addition of functional moieties such as drugs, dyes, etc. (Hackenberger, C. P. & Schwarzer, D. Chemoselective ligation and modification strategies for peptides and proteins. Angewandte Chemie International Edition 47, 10030-10074, doi:10.1002/anie.200801313 (2008)).

Site-specific modification of proteins has emerged as powerful tool to study proteins at the single amino acid level. However, it is still challenging to engineer a protein after its translation, i.e., making post-translational modifications, since the reactions required to functionalize a translated protein, e.g. by adding a label at only one specific amino acid are oftentimes difficult, time- and material-consuming. Thus, there is still a demand for engineering a protein so as to have readily available a protein with an adaptor that allows a functionalization of said polypeptide.

The present application satisfies this demand by the provision of means and methods for equipping a protein of interest at the C-terminus with an amino acid or amino acid derivative according to the invention which allows a functionalization of said protein as described herein below, characterized in the claims and illustrated by the appended Examples and Figures.

The inventors have unexpectedly discovered that, in contrast to the widespread prejudice in the prior art, tubulin-tyrosine ligase (TTL) is able to functionalize polypeptides modified to comprise a TTL-recognition sequence, with an amino acid or amino acid derivative according to the invention, other than tyrosine or derivatives thereof. In other words, the present inventors transferred action of TTL out of its context, i.e., its action on tubulin and showed that TTL is also active on heterologous substrates such as peptides or polypeptides that merely contain a TTL recognition sequence at their C-terminus, but are otherwise not structurally related to α tubulin, i.e., non-tubulin peptides or polypeptides and they showed that TTL is able to ligate such peptides or polypeptides to amino acids and derivatives thereof according to the invention, which are structurally different to the naturally applied tyrosine (see Examples 9-11). Thus, TTL is able to incorporate an amino acid or amino acid derivative according to the invention, which is different to tyrosine, into a non-tubulin polypeptide in a non-natural environment, while it was taught in the art that TTL is strictly tubulin and tyrosine dependent.

Accordingly, this finding enables the attachment of an amino acid or amino acid derivative according to the invention to a plethora of different polypeptides, and, by further addition of other moieties, opens new perspectives for research, diagnosis, and treatment. The ability of TTL to ligate various amino acids including non-natural amino acids and derivatives thereof according to the invention, allows the incorporation of amino acid derivatives, which are itself fluorescent, like tryptophan derivatives or coumarin derivatives and thereby a fluorescence labeling of proteins and polypeptides in a single step (see Examples 9-11). A subsequent bio-orthogonal functionalization of protein or polypeptide can thereby be omitted, resulting in a simplified method to produce labeled proteins and polypeptides, since only one final purification step is needed. Another advantage is the small size of tryptophan or coumarin derivatives compared to common fluorescent labels like Alexa-Fluor or Green Fluorescent Protein (GFP), resulting in reduced steric bulk and thereby a reduction of a potential steric clash of the fluorescent label with other biologically active molecules and/or with interaction partners of the labeled protein or polypeptide. Further, by making use of the action of TTL, it is possible to functionalize a polypeptide of interest (POI), since an amino acid or amino acid derivative according to the invention added by TTL to the C-terminus of a protein having a TTL recognition sequence allows coupling of moieties by way of a non-peptidic bond which serve, e.g. as labels, enzymes, drugs, etc. Thus, having recognized and proofed that TTL is active on heterologous substrates such as peptides or polypeptides that merely contain a TTL recognition sequence at their C-terminus, but are otherwise not structurally related to α tubulin, makes TTL a tool for equipping a POI with an amino acid or amino acid derivative according to the invention that acts as versatile adaptor that itself is connected with moieties which functionalize a POI for, e.g. research, diagnosis, and treatment.

Tubulin-tyrosine ligase (TTL), which was first isolated from brain extracts in 1977, catalyzes the post-translational retyrosination of detyrosinated α-tubulin. It has a marked degree of sequence conservation from echinoderms to humans, and exhibits >96% identity among mammalian orthologs (Szyk et al. (2011), Nature Struc Mol Biol 18(11): 1250-1259). Remarkably, the enzyme is indispensable for cell and organism development, and TTL suppression has been linked to cell transformation and correlates with poor prognosis in patients suffering from diverse forms of cancers (Prota et al. (2013), J Cell Biol 200(3): 259-270).

In nature, TTL plays an important role in recurrent α-tubulin detyrosination/tyrosination cycles. The high substrate specificity of TTL has early been acknowledged. Even before TTL had been isolated, Acre et al. (Arce et al. (1978), J. Neurosci. 31: 205-210) reported in 1975 that when brain extracts are incubated with radioactive tyrosine, the label is only incorporated into α tubulin. In 1994, Rüdiger et al. (Rüdiger et al. (1994), FEBS J. 220: 309-320) assessed TTL substrate requirements by using a variety of synthetic peptides corresponding to the C-terminal sequence of α-tubulin.

Interestingly, the prejudice that αβ-tubulin or fragments thereof were the only substrate accepted by TTL for efficient tyrosination persisted in the prior art. In consequence, research on TTL activity was, in the following years, confined to assess whether TTL would accept tyrosine derivatives and attach them to the αβ-tubulin heterodimer. For example, Kalisz et al. (2000), Biochim Biophys Acta 1481: 131-138 pioneered in generating recombinant TTL in $E.$ $coli$. The recombinant TTL exhibited similar catalytic properties as the mammalian brain tissue derived enzyme and was capable of covalently incorporating nitrotyrosine into the C-terminus of α-tubulin in vitro, albeit at 35-fold lower affinity than for tyrosine. Recently, Banerjee et al. (2010), ACS chemical biology 5: 777-785 successfully employed the TTL to conjugate a fluorescent label to αβ-tubulin. The authors developed a two step labeling systems under mild conditions and used 3-formyltyrosine as a TTL substrate and attached it to the C-terminus of α tubulin. Subsequently, 7-hydrazino-4-methyl coumarin was added by hydrazone formation to the modified tubulin as a fluorescent label under mild conditions, allowing fluorescently labeled tubulin to retain its ability to assemble into microtubules. Again, the authors here emphasize that the only TTL substrate is the C-terminus of α tubulin with the minimal requirement of EE as the last amino acids.

However, the idea to use TTL for attaching an amino acid (or derivatives thereof) according to the invention, in particular other than tyrosine (or derivatives thereof) to polypeptides, in particular other than tubulin, did not evolve— presumably because preceding studies implied that a unique interaction between TTL and αβ-tubulin was required in order to enable tyrosination, i.e. ligating αβ-tubulin with tyrosine. Recently, the prejudice has been confirmed by two studies conducted by (Szyk et al. (2011), Nature Struc Mol Biol 18(11): 1250-1259) and (Prota et al. (2013), J Cell Biol 200(3): 259-270).

Szyk et al. (2011), Nature Struc Mol Biol 18(11): 1250-1259 determined the crystal structure of frog TTL. The study revealed that TTL has an elongated shape and is composed of an N-terminal domain, a central domain and a C-terminal domain, which together form the active site of the enzyme. The authors further reported that TTL recognizes tubulin by a bipartite strategy. It engages the tubulin tail through low-affinity, high-specificity interactions, and co-opts what is otherwise a homo-oligomerization interface to form a tight hetero-oligomeric complex with the tubulin body. Put it differently, Szyk et al. clearly teach that TTL is highly specific for tubulin and tyrosine and for its action it requires a tight interplay with tubulin.

Prota et al. (2013), J Cell Biol 200(3): 259-270 recently revealed the structural basis of TTL-tubulin interaction and tubulin tyrosination. Interestingly, based on the structural information obtained during the study, the authors conclude that a characteristic bipartite αβ tubulin-TTL binding and α tubulin tail-TTL binding mode account for the high specificity of TTL for α tubulin. The authors state that the complex bipartite interaction mode observed between tubulin and TTL reveal how the enzyme has specifically evolved to recognize and modify tubulin with tyrosine; they virtually preclude that the enzyme modifies additional substrates.

The only indication, that TTL might also accept polypeptides other than tubulin was recently provided by Schumacher et al ((2015) Angew. Chem. Int. Ed. Engl. 54, 13787-13791). The authors reported that recombinant TTL was repurposed to attach tyrosine or small tyrosine derivatives like 3-$N_3$-L-tyrosine or 3-formyl-L-tryrosine to polypeptides containing a short tubulin-derived recognition sequence (Tub-tag). The possibility that TTL might be able to attach amino acids or amino acid derivatives other than tyrosine or derivatives thereof is neither mentioned nor suggested.

In sum, the prior art implies that TTL may be able to vary the polypeptide substrate for the ligation reaction, i.e.

employing also polypeptides different to the natural substrate αβtubulin, but being restricted to tyrosine or small tyrosine derivatives as coupling partners. Clearly, the finding of the present invention, allowing the ligation/tailing by TTL of amino acids or derivatives thereof, other than tyrosine, was unexpected and could not be foreseen (see Example 6). It was also surprising and unexpected, that TTL ligates amino acids and amino acid derivatives other than tyrosine to virtually any polypeptide carrying a TTL recognition motif (see Example 7).

SUMMARY

The present invention provides a method for the production of a functionalized polypeptide comprising
(a) introducing or adding at the C-terminus of a polypeptide a recognition sequence for tubulin tyrosine ligase;
(b) contacting the polypeptide obtained in step (a) in the presence of tubulin tyrosine ligase and a compound under conditions suitable for the tubulin tyrosine ligase to functionalize said polypeptide with said compound, wherein said compound having a structure according to Formula I

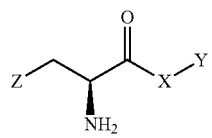

(I)

wherein
X is O, $NR^1$ or S;
Y is selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl;
Z is selected from the group consisting of substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl; and
$R^1$ is selected from the group consisting of hydrogen, substituted or unsubstituted $(C_1-C_6)$alkyl, substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_6-C_{14})$aryl and substituted or unsubstituted $(C_3-C_{14})$heteroaryl;
with the proviso that Z is not a substituted or unsubstituted monocyclic six-membered aryl; and
(c) optionally conjugating a moiety to said functionalized polypeptide obtained in step (b).

Step (c) is also envisaged to be a preferred step of the above method. Hence, in a preferred embodiment, said above method of the present invention further comprises step (c) conjugating a moiety to said functionalized polypeptide obtained in step (b), preferably a moiety as described herein.

In some embodiments the compound having a structure according to Formula I may be characterized in that,
X is O, $NR^1$ or S;
Y is hydrogen or substituted or unsubstituted $(C_1-C_6)$alkyl;
Z is selected from the group consisting of substituted or unsubstituted $(C_1-C_6)$alkyl, substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_7-C_{14})$aryl, substituted or unsubstituted $(C_6-C_{14})$aryl$(C_1-C_6)$alkyl, substituted or unsubstituted $(C_3-C_{14})$heteroaryl, substituted or unsubstituted $(C_3-C_{14})$heteroaryl$(C_1-C_6)$alkyl, substituted or unsubstituted $(C_3-C_{14})$heterocyclyl, substituted or unsubstituted $(C_1-C_6)$heteroalkyl, substituted or unsubstituted $(C_2-C_6)$heteroalkenyl and substituted or unsubstituted $(C_2-C_6)$heteroalkynyl; and
$R^1$ is hydrogen or substituted or unsubstituted $(C_1-C_6)$alkyl;
with the proviso that Z is not a substituted or unsubstituted monocyclic six-membered aryl.

In another embodiment the compound having a structure according to Formula I may be characterized in that,
X is O, $NR^1$ or S;
Y is hydrogen or substituted or unsubstituted $(C_1-C_6)$alkyl;
Z is selected from the group consisting of substituted or unsubstituted 2H-1-benzopyranyl (2H-chromenyl), substituted or unsubstituted benzodihydropyranyl (chromanyl), substituted or unsubstituted 4H-1-benzopyranyl (4H-chromenyl), substituted or unsubstituted 1H-2-benzopyranyl (1H-isochromenyl), substituted or unsubstituted isochromanyl, substituted or unsubstituted 3H-2-benzopyranyl (3H-isochromenyl), substituted or unsubstituted 1-benzopyran-4-on-yl (chromonyl), substituted or unsubstituted 4-chromanonyl, substituted or unsubstituted 1-benzopyran-2-on-yl (coumarinyl), substituted or unsubstituted dihydrocoumarinyl, substituted or unsubstituted 3-isochromanonyl, substituted or unsubstituted 2-coumaranonyl, substituted or unsubstituted $(C_1-C_6)$alkyl, substituted or unsubstituted $(C_1-C_6)$heteroalkyl, substituted or unsubstituted imidazolyl, substituted or unsubstituted azaindolyl including 7-azaindolyl, 6-azaindolyl, 5-azaindolyl and 4-azaindolyl, substituted or unsubstituted diazaindolyl and substituted or unsubstituted indolyl; and
$R^1$ is hydrogen or substituted or unsubstituted $(C_1-C_6)$alkyl.

The present invention also provides a polypeptide which is obtainable by the methods, particularly by said above method of the present invention. Such polypeptide obtainable by the methods of the present invention and applied therein may advantageously have a length of more than 19 amino acids and/or may be a polypeptide other than tubulin or the polypeptide may be tubulin.

The present invention, as an alternative to the afore described method, provides a method for the production of a functionalized polypeptide comprising (a') introducing or adding at the C-terminus of a polypeptide a recognition sequence for tubulin tyrosine ligase; and (b') contacting the polypeptide obtained in step (a') in the presence of tubulin tyrosine ligase and a compound conjugated to a moiety under conditions suitable for the tubulin tyrosine ligase to functionalize said polypeptide with said compound conjugated to said moiety, wherein said compound having a structure according to Formula I

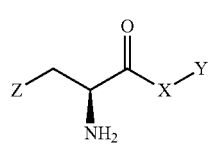
(I)

wherein
X is O, NR$^1$ or S;
Y is selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl;
Z is selected from the group consisting of substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl; and
R$^1$ is selected from the group consisting of hydrogen, substituted or unsubstituted (C$_1$-C$_6$)alkyl, substituted or unsubstituted (C$_2$-C$_6$)alkenyl, substituted or unsubstituted (C$_2$-C$_6$)alkynyl, substituted or unsubstituted (C$_3$-C$_8$)cycloalkyl, substituted or unsubstituted (C$_6$-C$_{14}$)aryl and substituted or unsubstituted (C$_3$-C$_{14}$)heteroaryl, and
wherein said moiety is conjugated to the Y-group and/or Z-group, with the proviso that
(i) said Y group is not hydrogen when conjugated to said moiety;
(ii) Z is not a substituted or unsubstituted monocyclic six-membered aryl.

The compound having a structure according to Formula I may be characterized in that,
X is O, NR$^1$ or S;
Y is hydrogen or substituted or unsubstituted (C$_1$-C$_6$) alkyl;
Z is selected from the group consisting of substituted or unsubstituted (C$_1$-C$_6$)alkyl, substituted or unsubstituted (C$_2$-C$_6$)alkenyl, substituted or unsubstituted (C$_2$-C$_6$)alkynyl, substituted or unsubstituted (C$_3$-C$_8$)cycloalkyl, substituted or unsubstituted (C$_7$-C$_{14}$)aryl, substituted or unsubstituted (C$_6$-C$_{14}$)aryl(C$_1$-C$_6$)alkyl, substituted or unsubstituted (C$_3$-C$_{14}$)heteroaryl, and substituted or unsubstituted (C$_3$-C$_{14}$)heteroaryl(C$_1$-C$_6$)alkyl, substituted or unsubstituted (C$_3$-C$_{14}$)heterocyclyl, substituted or unsubstituted (C$_1$-C$_6$)heteroalkyl, substituted or unsubstituted (C$_2$-C$_6$)heteroalkenyl and substituted or unsubstituted (C$_2$-C$_6$)heteroalkynyl; and
R$^1$ is hydrogen or substituted or unsubstituted (C$_1$-C$_6$) alkyl.

In another embodiment the compound having a structure according to Formula I may be characterized in that,
X is O, NR$^1$ or S;
Y is hydrogen or substituted or unsubstituted (C$_1$-C$_6$) alkyl;
Z is selected from the group consisting of substituted or unsubstituted 2H-1-benzopyranyl (2H-chromenyl), substituted or unsubstituted benzodihydropyranyl (chromanyl), substituted or unsubstituted 4H-1-benzopyranyl (4H-chromenyl), substituted or unsubstituted 1H-2-benzopyranyl (1H-isochromenyl), substituted or unsubstituted isochromanyl, substituted or unsubstituted 3H-2-benzopyranyl (3H-isochromenyl), substituted or unsubstituted 1-benzopyran-4-on-yl (chromonyl), substituted or unsubstituted 4-chromanonyl, substituted or unsubstituted 1-benzopyran-2-on-yl (coumarinyl), substituted or unsubstituted dihydrocoumarinyl, substituted or unsubstituted 3-isochromanonyl, substituted or unsubstituted 2-coumaranonyl, substituted or unsubstituted (C$_1$-C$_6$)alkyl, substituted or unsubstituted (C$_1$-C$_6$)heteroalkyl, substituted or unsubstituted imidazolyl, substituted or unsubstituted azaindolyl including 7-azaindolyl, 6-azaindolyl, 5-azaindolyl and 4-azaindolyl, substituted or unsubstituted diazaindolyl and substituted or unsubstituted indolyl; and
R$^1$ is hydrogen or substituted or unsubstituted (C$_1$-C$_6$) alkyl.

The present invention also provides a polypeptide obtainable by said alternative method of the present invention. Such a polypeptide may, for example, also be tubulin, since the prior art did not provide tubulin comprising an compound having a structure according to Formula I and a further moiety, preferably a moiety as described herein. Such polypeptide obtainable by the methods of the present invention and applied therein may advantageously have a length of more than 19 amino acids.

The present invention, as an alternative to the afore described methods, provides a method for the production of a functionalized polypeptide comprising
(a'') introducing or adding at the C-terminus of a polypeptide a recognition sequence for tubulin tyrosine ligase;
(b'') contacting the polypeptide obtained in step (a) in the presence of tubulin tyrosine ligase and a compound under conditions suitable for the tubulin tyrosine ligase to functionalize said polypeptide with said compound having a structure according to Formula I

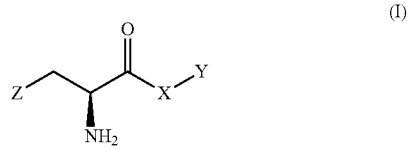
(I)

wherein

X is O, $NR^1$ or S;

Y is selected from the group consisting of a substituted or unsubstituted aliphatic group, a substituted or unsubstituted heteroaliphatic group, substituted or unsubstituted aryl, substituted or unsubstituted arylalkyl, substituted or unsubstituted heteroaryl, substituted or unsubstituted heteroarylalkyl, substituted or unsubstituted heterocyclyl, a click chemistry handle, biotin, a carrier, a polypeptide, a detectable label, a chemical compound, a nucleic acid, a carbohydrate, or a lipid;

Z is selected from the group consisting of a substituted or unsubstituted aliphatic group, a substituted or unsubstituted heteroaliphatic group, substituted or unsubstituted aryl, substituted or unsubstituted arylalkyl, substituted or unsubstituted heteroaryl, substituted or unsubstituted heteroarylalkyl, substituted or unsubstituted heterocyclyl, a click chemistry handle, biotin, a carrier, a polypeptide, a detectable label, a chemical compound, a nucleic acid, a carbohydrate, or a lipid; and $R^1$ is selected from the group consisting of hydrogen, substituted or unsubstituted $(C_1-C_6)$alkyl, substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_6-C_{14})$aryl and substituted or unsubstituted $(C_3-C_{14})$heteroaryl; and with the proviso that Z is not a substituted or unsubstituted monocyclic six-membered aryl.

Such a polypeptide that is conjugated to a functionalized polypeptide may be an antibody or fragment thereof selected from the group consisting of a monoclonal antibody, chimeric antibody, humanized antibody, human antibody, scFv, a DART, domain antibody, nanobody, an adnectin, an affibody, an anticalin, a DARPin, or an aptamer. Such a detectable label may comprise a fluorophore, an enzyme (peroxidase, luciferase), a radioisotope, a PET-tracer, a fluorescent protein, or a fluorescent dye. Such a chemical compound may be a small molecule, a polymer, such as a synthetic polymer (PEG) or a therapeutic agent. Such a nucleic acid may be DNA, RNA, or an aptamer.

The present invention also provides a polypeptide obtainable by said alternative method of the present invention. Such a polypeptide may be tubulin or may be a polypeptide other than tubulin. Such polypeptide obtainable by the methods of the present invention and applied therein may advantageously have a length of more than 19 amino acids.

The recognition sequence for tubulin tyrosine ligase of a polypeptide that is subjected to a method of the present invention and that may also be comprised by a polypeptide of the present invention may preferably have at least the amino acid sequence $X_1X_2X_3X_4$ (SEQ ID No: 9), wherein $X_1$ and $X_2$ is any amino acid, $X_3$ is E, D or C and $X_4$ is E. Advantageously, $X_2$ may be G, S, A, V, or F and/or $X_1$ may be E, D, A, K, or P. The recognition sequence may be EGEE (SEQ ID No. 2), VDSVEGEGEEEGEE (SEQ ID No. 3), SVEGEGEEEGEE (SEQ ID No. 4), SADGEDEGEE (SEQ ID No. 5), SVEAEAEEGEE (SEQ ID No. 6), SYEDEDEGEE (SEQ ID No. 7), or SFEEENEGEE (SEQ ID No. 8).

The polypeptide that is produced and thus obtainable by the methods of the invention may comprise a linker sequence preceding the recognition sequence of tubulin tyrosine ligase.

The moiety that may be conjugated to a functionalized polypeptide by way of the methods of the present invention and that may be comprised by a polypeptide of the present invention may a carrier, a polypeptide, a detectable label, a chemical compound, a nucleic acid, a carbohydrate, or a lipid. Such a polypeptide that is conjugated to a functionalized polypeptide may be an antibody or fragment thereof selected from the group consisting of a monoclonal antibody, chimeric antibody, humanized antibody, human antibody, scFv, a DART, domain antibody, nanobody, an adnectin, an affibody, an anticalin, a DARPin, or an aptamer. Such a detectable label may comprise a fluorophore, an enzyme (peroxidase, luciferase), a radioisotope, a PET-tracer, a fluorescent protein, or a fluorescent dye. Such a chemical compound may be a small molecule, a polymer, such as a synthetic polymer (PEG) or a therapeutic agent. Such a nucleic acid may be DNA, RNA, or an aptamer.

Suitable conditions applied in the methods for producing a polypeptide of the invention may comprise a buffer containing a nucleoside triphosphate, such as ATP, potassium chloride, magnesium chloride, a reducing agent such as DTT. The suitable conditions may comprise a pH-value in the range of 5 to 9. The suitable conditions may comprise a concentration of the compound having a structure according to formula I in the range of 0.1 mM to 10 mM. The suitable conditions may comprise a reaction temperature in the range of 1° C. to 70° C., preferably 19° C. to 37° C. The suitable conditions may comprise a reaction time in the range of 5 minutes to 4 hours, preferably 1 hour to 3 hours.

A polypeptide that is provided herein which is, for example, obtainable by the present invention has at its C-terminus a recognition sequence for tubulin tyrosine ligase (TTL) which has preferably at least the amino acid sequence $X_4X_3X_2X_1$, wherein $X_2$ is E, D or C and $X_1$ is E. Advantageously, such a polypeptide is modified to introduce or add said recognition sequence. Said polypeptide has advantageously biological activity.

$X_4$ can be E, D, A, K, or P. $X_3$ can be G, S, A, V, or F. $X_2$ may also be G, S, A, V, or F. $X_1$ may also be E, D, A, K, or P. Preferably, the recognition sequence may be EGEE (SEQ ID No. 2), VDSVEGEGEEEGEE (SEQ ID No. 3), SVEGEGEEEGEE (SEQ ID No. 4), SADGEDEGEE (SEQ ID No. 5), SVEAEAEEGEE (SEQ ID No. 6), SYEDEDEGEE (SEQ ID No. 7), or SFEEENEGEE (SEQ ID No. 8).

The polypeptide can comprise a linker sequence preceding the recognition sequence of tubulin tyrosine ligase.

In the polypeptide of the invention, a compound having a structure according to Formula I can be covalently bonded to said recognition sequence for tubulin tyrosine ligase (TTL). Further, a moiety can be conjugated to said compound having a structure according to Formula I. Said moiety can be a carrier, a polypeptide, a detectable label, a chemical compound, a nucleic acid, a carbohydrate, or a lipid. The polypeptide can be, in particular, an antibody or fragment thereof selected from the group consisting of a monoclonal antibody, chimeric antibody, humanized antibody, human antibody, scFv, a DART, domain antibody, nanobody, an adnectin, an affibody, an anticalin, a DARPin, or an aptamer. The detectable label may comprise a fluorophore, an enzyme (peroxidase, luciferase), a radioisotope, a fluorescent protein, or a fluorescent dye. The chemical compound can be a small molecule, a polymer, such as a synthetic polymer (PEG) or a therapeutic agent. The nucleic acid can be DNA, RNA, or an aptamer.

Also provided by the present invention is a diagnostic composition comprising a polypeptide that is, for example, obtainable by the methods of the present invention.

Furthermore, also provided is a pharmaceutical composition a polypeptide that is, for example, obtainable by the methods of the present invention.

The present invention moreover provides a kit comprising means for performing the method of the present invention. The kit may comprise an expression vector which allows expression of a protein of interest fused at its C-Terminus to a recognition sequence for tubulin tyrosine ligase, tubulin tyrosine ligase and a compound having a structure according to formula I

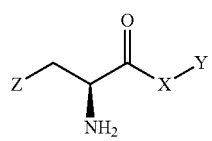

wherein
X is O, $NR^1$ or S;
Y is selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl;
Z is selected from the group consisting of substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl; and
$R^1$ is selected from the group consisting of hydrogen, substituted or unsubstituted $(C_1-C_6)$alkyl, substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_6-C_{14})$aryl and substituted or unsubstituted $(C_3-C_{14})$heteroaryl; and
with the proviso that Z is not a substituted or unsubstituted monocyclic six-membered aryl.

The kit may comprise an expression vector which allows expression of a protein of interest fused at its C-Terminus to a recognition sequence for tubulin tyrosine ligase, tubulin tyrosine ligase and a compound having a structure according to formula I

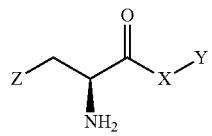

wherein
X is O, $NR^1$ or S;
Y is selected from the group consisting of a substituted or unsubstituted aliphatic group, a substituted or unsubstituted heteroaliphatic group, substituted or unsubstituted aryl, substituted or unsubstituted arylalkyl, substituted or unsubstituted heteroaryl, substituted or unsubstituted heteroarylalkyl, substituted or unsubstituted heterocyclyl, a click chemistry handle, biotin, a carrier, a polypeptide, a detectable label, a chemical compound, a nucleic acid, a carbohydrate, or a lipid;
Z is selected from the group consisting of a substituted or unsubstituted aliphatic group, a substituted or unsubstituted heteroaliphatic group, substituted or unsubstituted aryl, substituted or unsubstituted arylalkyl, substituted or unsubstituted heteroaryl, substituted or unsubstituted heteroarylalkyl, substituted or unsubstituted heterocyclyl, a click chemistry handle, biotin, a carrier, a polypeptide, a detectable label, a chemical compound, a nucleic acid, a carbohydrate, or a lipid; and
$R^1$ is selected from the group consisting of hydrogen, substituted or unsubstituted $(C_1-C_6)$alkyl, substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_6-C_{14})$aryl and substituted or unsubstituted $(C_3-C_{14})$heteroaryl;
with the proviso that Z is not a substituted or unsubstituted monocyclic six-membered aryl.

Such a polypeptide that is conjugated to a functionalized polypeptide may be an antibody or fragment thereof selected from the group consisting of a monoclonal antibody, chimeric antibody, humanized antibody, human antibody, scFv, a DART, domain antibody, nanobody, an adnectin, an affibody, an anticalin, a DARPin, or an aptamer. Such a detectable label may comprise a fluorophore, an enzyme (peroxidase, luciferase), a radioisotope, a PET-tracer, a fluorescent protein, or a fluorescent dye. Such a chemical compound may be a small molecule, a polymer, such as a synthetic polymer (PEG) or a therapeutic agent. Such a nucleic acid may be DNA, RNA, or an aptamer.

Also provided by the present invention is the use of tubulin tyrosine ligase for functionalizing a polypeptide having at its C-terminus a recognition sequence for tubulin tyrosine ligase, a compound having a structure according to formula I

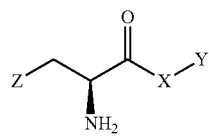

wherein
X is O, $NR^1$ or S;
Y is selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl;
Z is selected from the group consisting of substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl; and $R^1$ is selected from the group consisting of hydrogen, substituted or unsubstituted $(C_1$-$C_6)$alkyl, substituted or unsubstituted $(C_2$-$C_6)$alkenyl, substituted or unsubstituted $(C_2$-$C_6)$alkynyl, substituted or unsubstituted $(C_3$-$C_8)$cycloalkyl, substituted or unsubstituted $(C_6$-$C_{14})$aryl and substituted or unsubstituted $(C_3$-$C_{14})$heteroaryl;

with the proviso that Z is not a substituted or unsubstituted monocyclic six-membered aryl.

Also provided by the present invention is the use of tubulin tyrosine ligase for functionalizing a polypeptide having at its C-terminus a recognition sequence for tubulin tyrosine ligase, a compound having a structure according to formula I

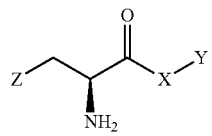

wherein

X is O, $NR^1$ or S;

Y is selected from the group consisting of a substituted or unsubstituted aliphatic group, substituted or unsubstituted aryl, substituted or unsubstituted arylalkyl, substituted or unsubstituted heteroaryl, substituted or unsubstituted heteroarylalkyl, a substituted or unsubstituted heteroaliphatic group, substituted or unsubstituted heterocyclyl, a click chemistry handle, biotin, a carrier, a polypeptide, a detectable label, a chemical compound, a nucleic acid, a carbohydrate, or a lipid;

Z is selected from the group consisting of a substituted or unsubstituted aliphatic group, a substituted or unsubstituted heteroaliphatic group, substituted or unsubstituted aryl, substituted or unsubstituted arylalkyl, substituted or unsubstituted heteroaryl, substituted or unsubstituted heteroarylalkyl, substituted or unsubstituted heterocyclyl, a click chemistry handle, biotin, a carrier, a polypeptide, a detectable label, a chemical compound, a nucleic acid, a carbohydrate, or a lipid; and $R^1$ is selected from the group consisting of hydrogen, substituted or unsubstituted $(C_1$-$C_6)$alkyl, substituted or unsubstituted $(C_2$-$C_6)$alkenyl, substituted or unsubstituted $(C_2$-$C_6)$alkynyl, substituted or unsubstituted $(C_3$-$C_8)$cycloalkyl, substituted or unsubstituted $(C_6$-$C_{14})$aryl and substituted or unsubstituted $(C_3$-$C_{14})$heteroaryl;

with the proviso that Z is not a substituted or unsubstituted monocyclic six-membered aryl.

Such a polypeptide that is conjugated to a functionalized polypeptide may be an antibody or fragment thereof selected from the group consisting of a monoclonal antibody, chimeric antibody, humanized antibody, human antibody, scFv, a DART, domain antibody, nanobody, an adnectin, an affibody, an anticalin, a DARPin, or an aptamer. Such a detectable label may comprise a fluorophore, an enzyme (peroxidase, luciferase), a radioisotope, a PET-tracer, a fluorescent protein, or a fluorescent dye. Such a chemical compound may be a small molecule, a polymer, such as a synthetic polymer (PEG) or a therapeutic agent. Such a nucleic acid may be DNA, RNA, or an aptamer.

In some embodiments the polypeptide to be functionalized by TTL, may be polypeptide other than tubulin.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range. It includes, however, also the concrete number, e.g., about 20 includes 20.

The term "less than" or "greater than" includes the concrete number. For example, less than 20 means less than or equal to. Similarly, more than or greater than means more than or equal to, or greater than or equal to, respectively.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

In order that the present invention may be more readily understood, certain terms are first defined. Additional definitions are set forth throughout the description.

FIGURES

FIG. 1: Site-specific functionalization of proteins by the enzyme TTL. (A) Already known, two step approach for the site-specific functionalization of a polypeptide using tyrosine-derivatives. (B) One-step approach for the site specific functionalization of a polypeptide with a coumarin derivative mediated by TTL. TTL: tubulin-tyrosine ligase.

Figure 2:
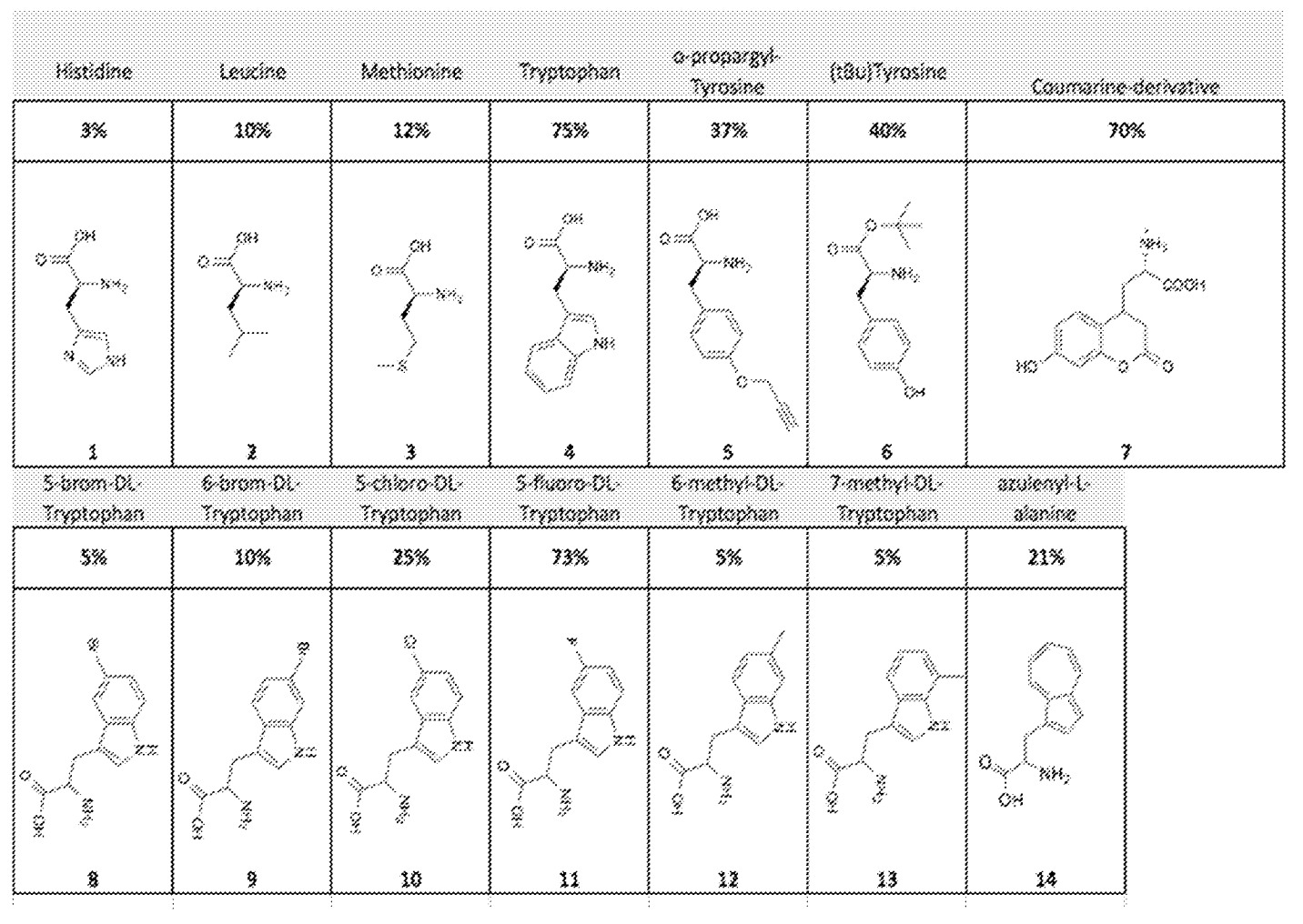

FIG. 2: Incorporation yields of various amino acids and amino acid derivatives into the model peptide carboxyfluorescein-VDSVEGEGEEEGEE (18) mediated by TTL after five hours of incubation time.

Figure 3:
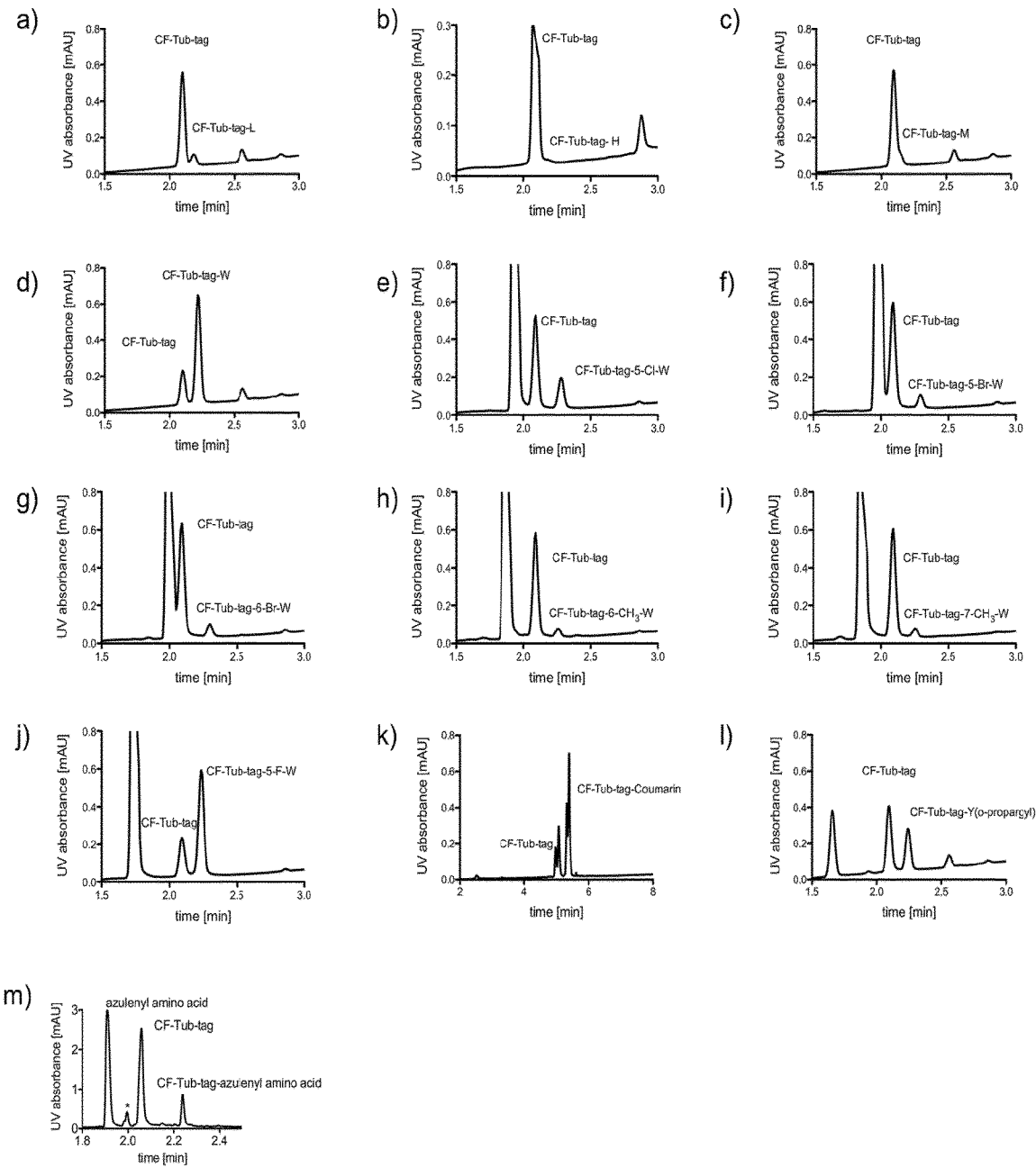

FIG. 3: UPLC UV-traces (220 nm) showing the incorporation of several substrates (A-L) to the CF-Tub-tag peptide Carboxyfluorescein-VDSVEGEGEEEGEE (18) after five hours of incubation. (A) leucine 2, (B) histidine 1, (C) methionine 3, (D) tryptophan 4, (E) 5-chloro-tryptophan 10, (F) 5-bromo-tryptophan 8, (G) 6-bromo-tryptophan 9, (H) 6-methyl-tryptophan 12, (I) 7-methyl-tryptophan 13, (J) 5-fluoro-tryptophan 11, (K) coumarin derivative 7, (L) tyrosine derivative 5, (M) derivative 14.

Figure 4:
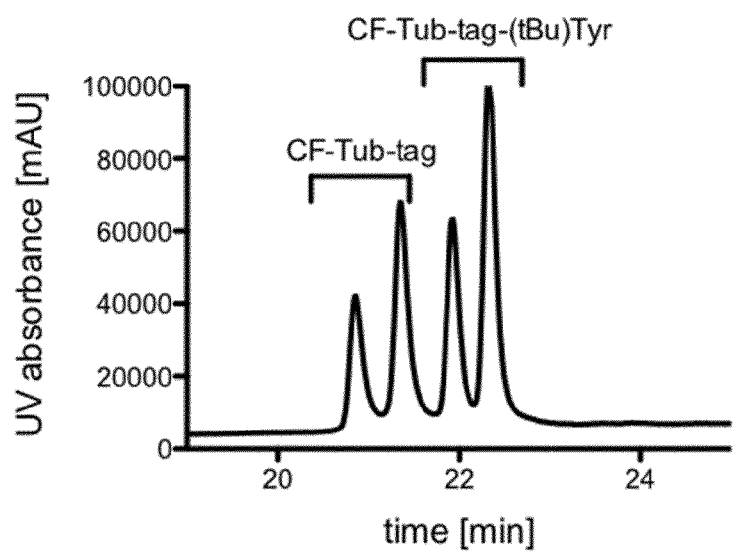

FIG. 4: HPLC UV-trace (220 nm) showing the incorporation of (tButyl)tyrosine (6) to the CF-Tub-tag peptide Carboxyfluorescein-VDSVEGEGEEEGEE (8) after five hours of incubation. The isomers of carboxyfluorescein are separated by the HPLC method.

Figure 5:
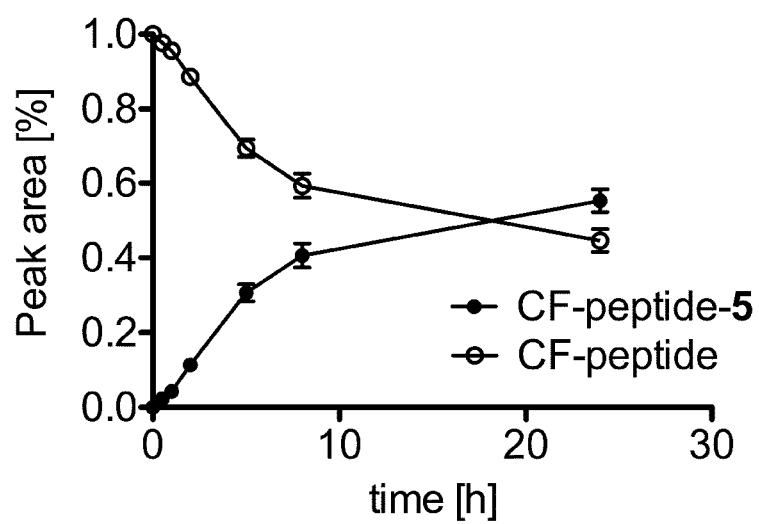

FIG. 5: Ligation efficiency of 5 to the Tub-tag peptide 8. UPLC-MS traces were taken at different time points of the TTL reaction and quantitation of substrate and product was performed through peak integration as described before. The mean values and standard deviation (SD) of three replicate reactions are shown.

Figure 6:
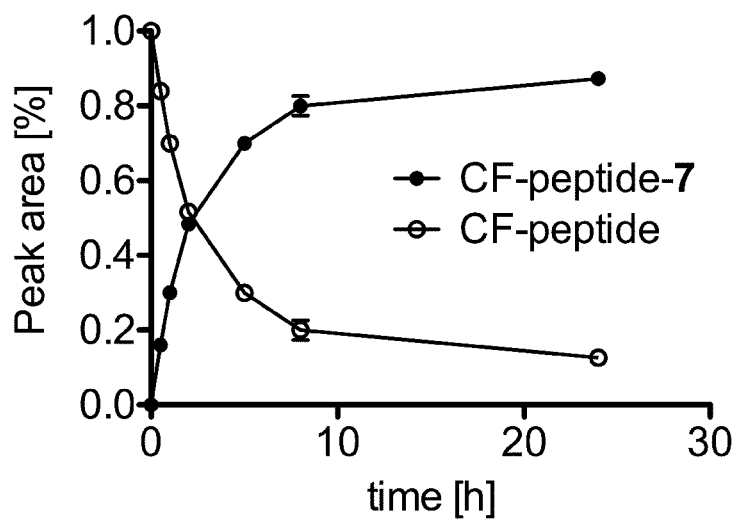

FIG. 6: Ligation efficiency of 7 to the Tub-tag peptide 8. UPLC-MS traces were taken at different time points of the TTL reaction and quantitation of substrate and product was performed through peak integration as described before. The mean values and standard deviation (SD) of three replicate reactions are shown.

Figure 7:
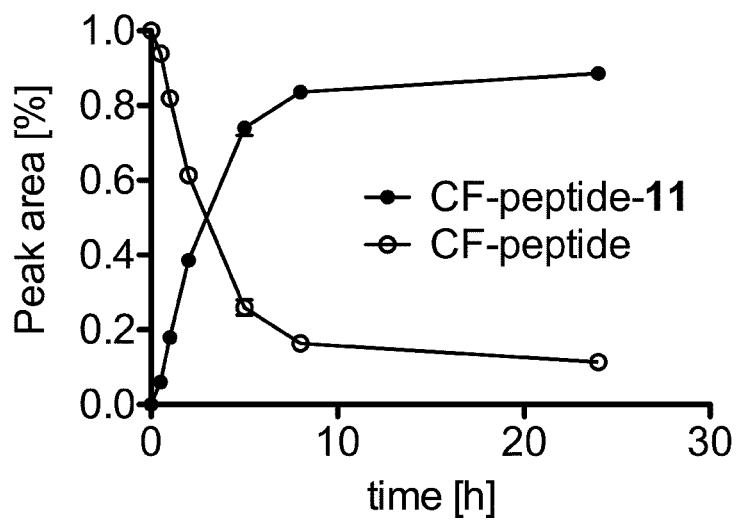

FIG. 7: Ligation efficiency of 11 to the Tub-tag peptide 8. UPLC-MS traces were taken at different time points of the TTL reaction and quantitation of substrate and product was performed through peak integration as described before. The mean values and standard deviation (SD) of three replicate reactions are shown.

Figure 8:
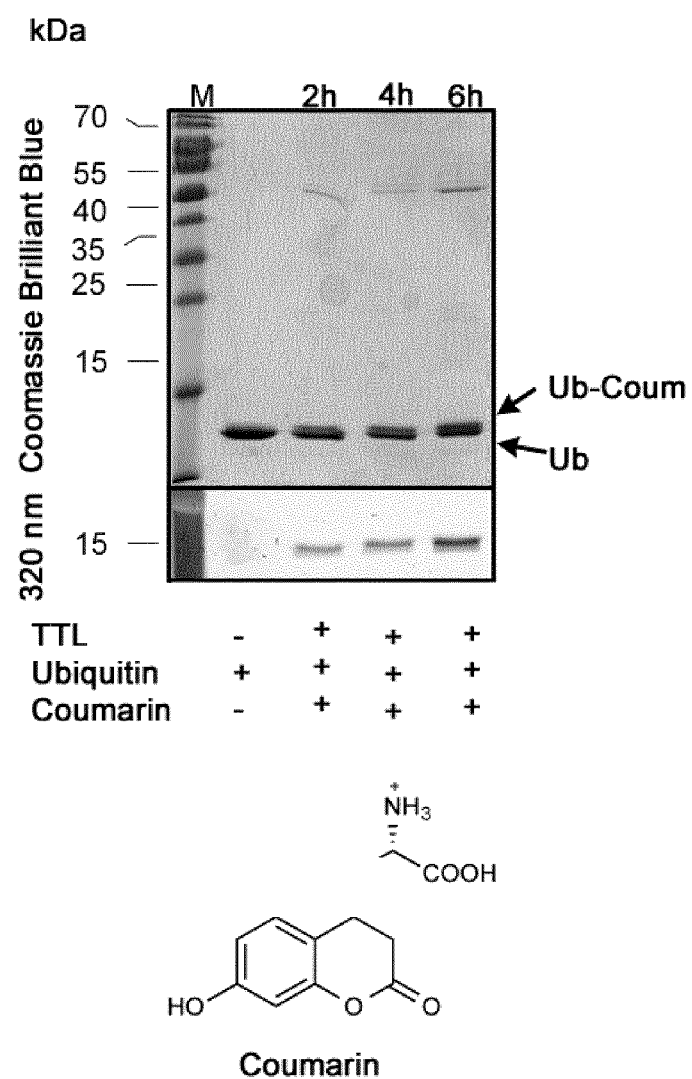

FIG. 8: SDS-PAGE analysis of the TTL catalysed coumarin incorporation to ubiquitin. Ub: Ubiquitin, Ub-Coum: Ubiquitin with incorporated coumarin derivative, TTL: tubulin-tyrosine ligase.

Figure 9:
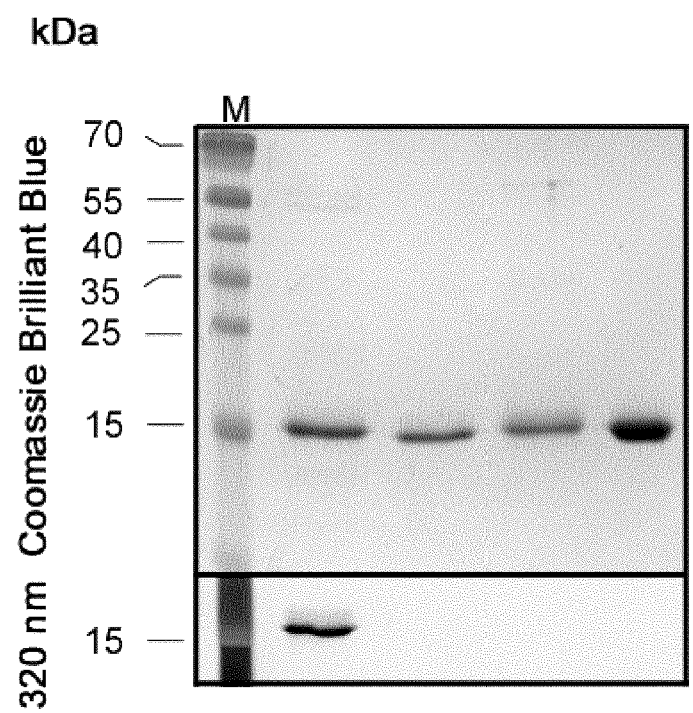
Figure 9:
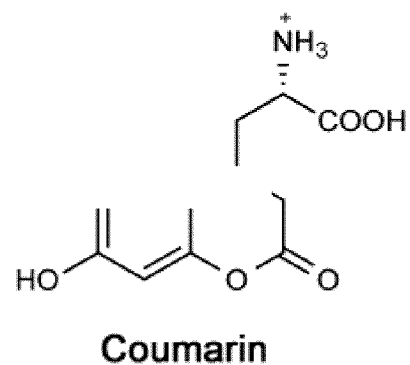

FIG. 9: SDS-PAGE analysis of the TTL catalysed coumarin incorporation to a GFP binding nanobody (GBP). TTL: tubulin-tyrosine ligase.

Figure 10:
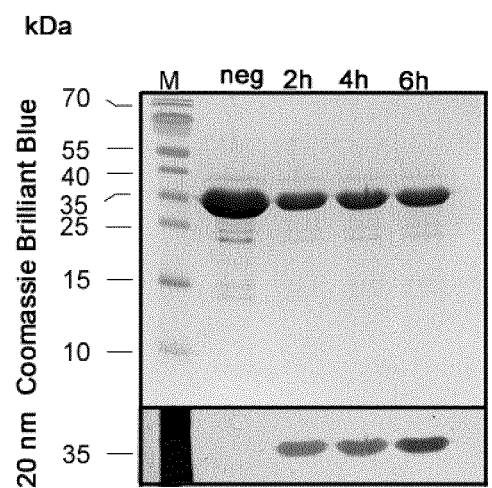
Figure 10:
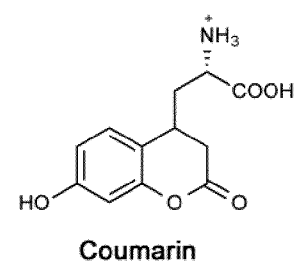

FIG. 10: SDS-PAGE analysis of the TTL catalysed coumarin incorporation to Annexin V. TTL: tubulin-tyrosine ligase.

Figure 11:
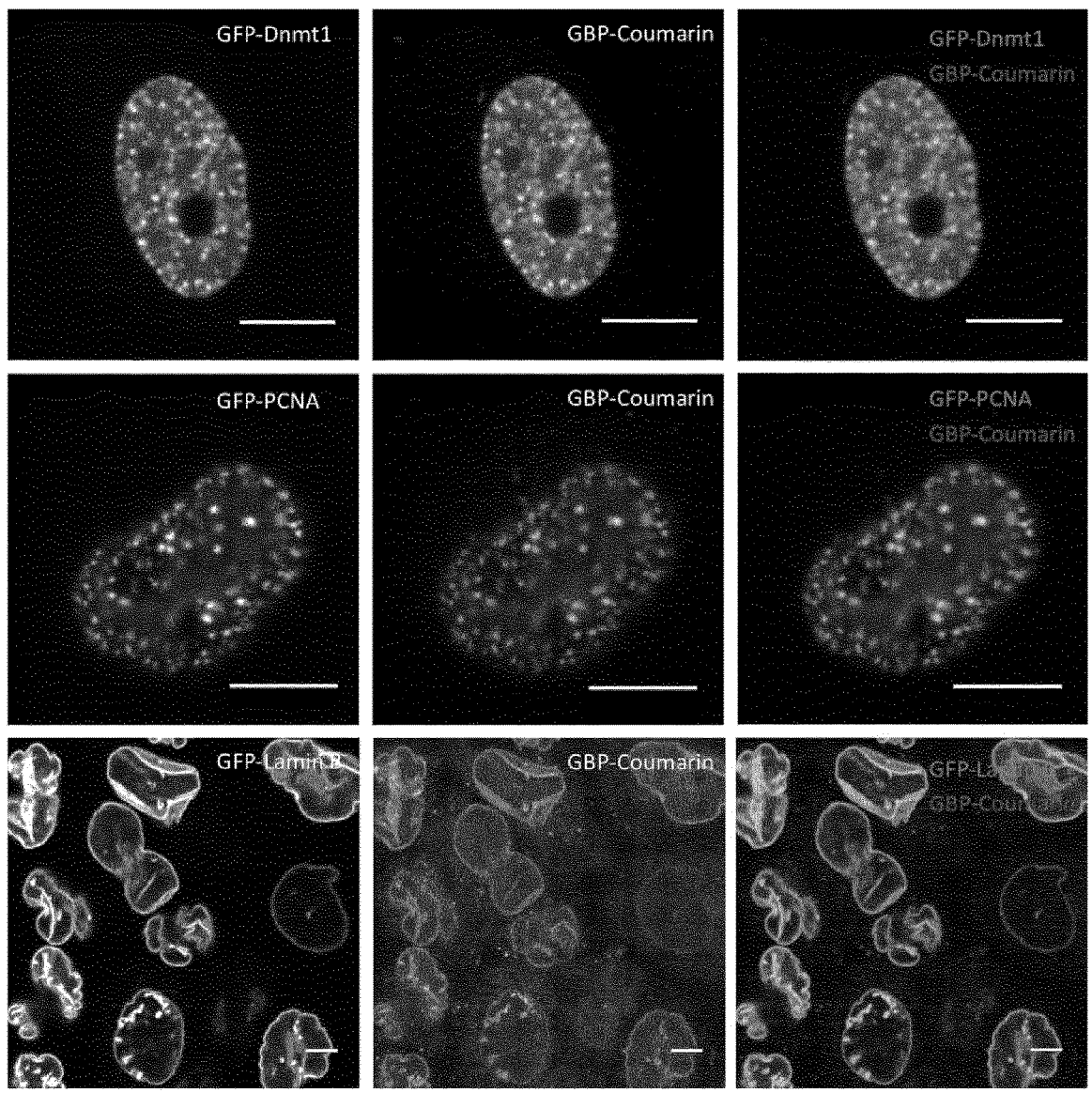

FIG. 11: A GFP binding nanobody was site-specifically labelled with the fluorescent coumarin derivative 7 using the enzyme TTL and in a subsequent experiment used to detect GFP fusion proteins (GFP-PCNA, GFP-Dmnt and GFP-Lamin) in fixed Hela cells. TTL: tubulin-tyrosine ligase, GFP: Green fluorescent protein, PCNA: Proliferating-cell-nuclear-antigen, Dmnt: DNA methyltransferase.

Figure 12:
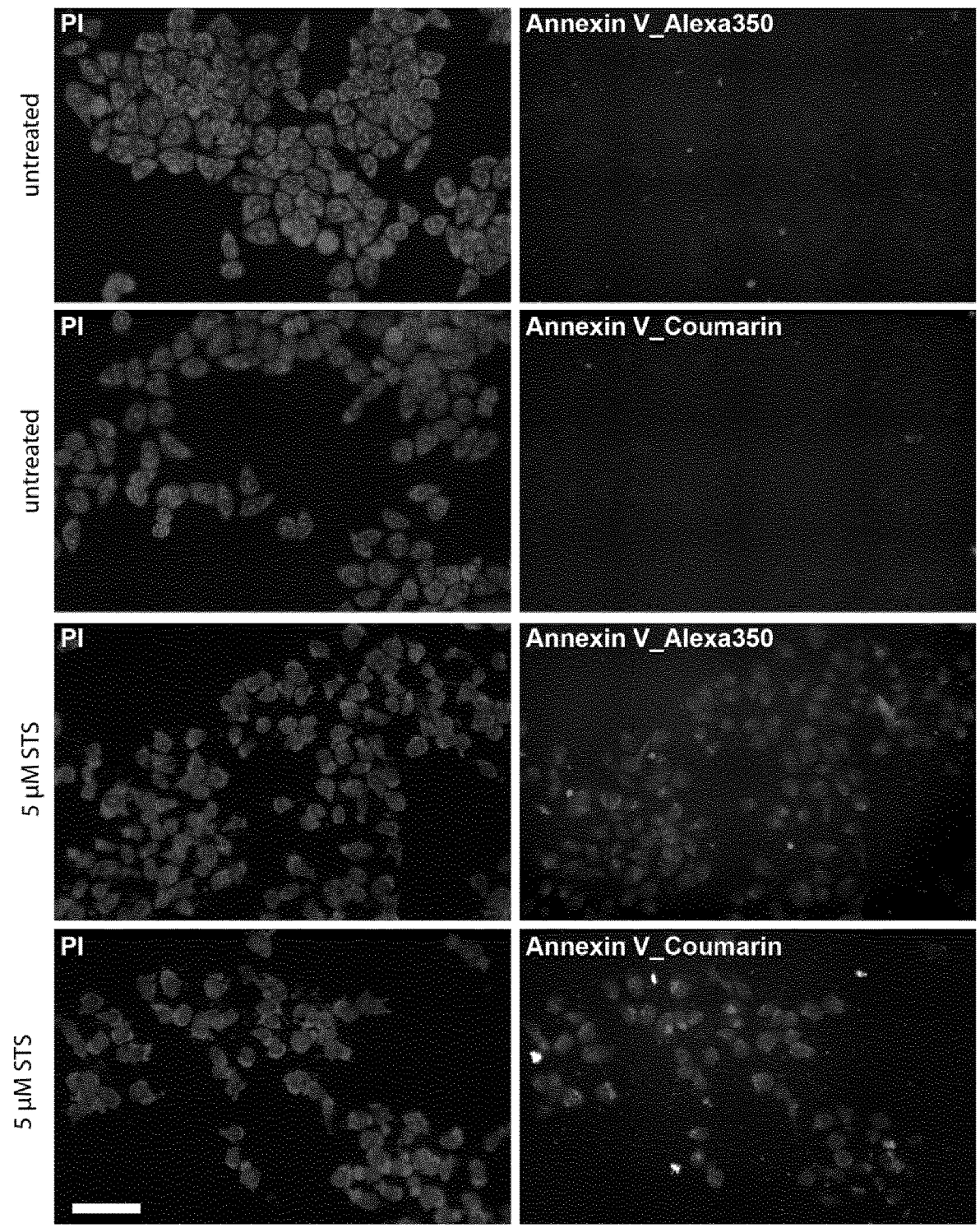

FIG. 12: Detection of apoptotic cells with Annexin V_Coumarin and commercial Annexin V_Alexa350. Staurosporine-treated (5 µM; lower panels) and untreated cells (upper panels) were stained with commercial Annexin V_Alexa350 or Annexin V_Coumarin, generated via Tub-tag mediated functionalization and counterstained with Propidium Iodide.

Figure 13:
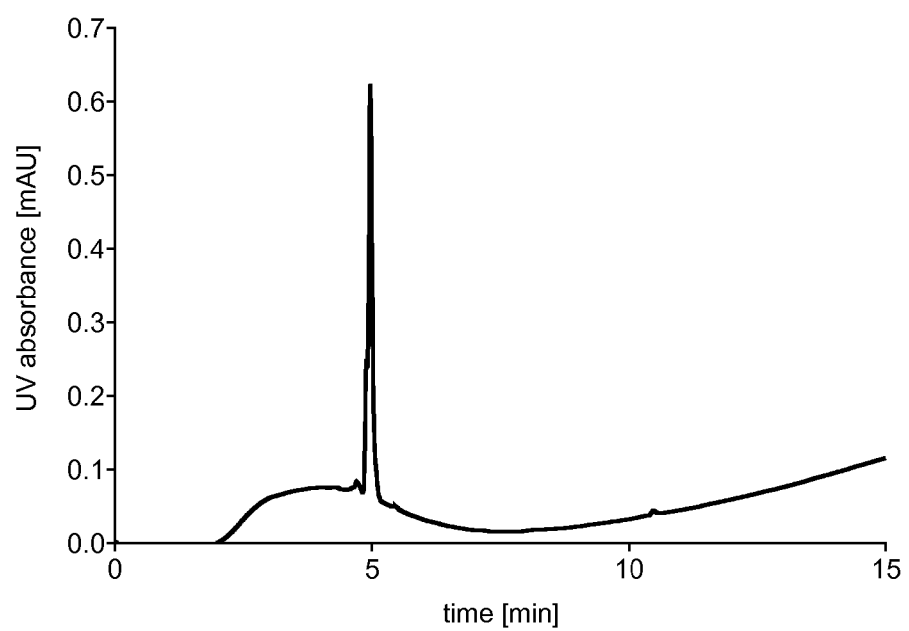

FIG. 13: LC-UV at 220 nm of purified peptide (18) (method A).

DETAILED DESCRIPTION

The present inventors have, for the first time, acknowledged that TTL activity is not limited to tubulin and tyrosine, but that TTL is capable of ligating a compound having a structure according to Formula I according to the present invention virtually to any polypeptide having a C-terminal TTL recognition motif in its amino acid sequence. This insight was by far not self-evident—in the past, several studies investigated the principles of TTL-tubulin interaction, and came to the conclusion that the unique interaction of TTL and its substrate tubulin was essential for effective tyrosination. Only recently it has been found that TTL is also able to ligate polypeptides containing a short tubulin-derived recognition sequence (Tub-tag) with tyrosine or small tyrosine derivatives. The insight that TTL could functionalize any polypeptide carrying the specific recognition motif with a compound having a structure according to Formula I according to the invention therefore came as a surprise. This surprising finding opens up new avenues for post-translational modifications of polypeptides, since the incorporated compound having a structure according to Formula I may comprise a functional entity that allows its conjugation to whatever moiety that can confer functionality to a polypeptide of interest that is functionalized by such compound having a structure according to Formula I. The present invention therefore provides novel polypeptides carrying a C-terminal TTL recognition sequence; which can, inter alia, act as TTL substrates to become functionalized by a compound having a structure according to Formula I and, advantageously further functionalized, since—as explained—the C-terminal compound having a structure according to Formula I can beneficially be used as an "adapter" for attaching further moieties, e.g. fluorescent labels or therapeutic agents. Another advantage of the present invention is, that the methods provide herein allow the incorporation of amino acids or derivatives thereof, which are itself fluorescent, like tryptophan derivatives or coumarin derivatives and thereby a fluorescence labeling of proteins and polypeptides in a single step (see Examples 9-11). A subsequent bio-orthogonal functionalization of protein or polypeptide can thereby be omitted, resulting in a simplified method to produce labeled proteins and polypeptides, since only one final purification step is needed. Another advantage is the small size of tryptophan or coumarin derivatives compared to common fluorescent labels like Alexa-Fluor or Green Fluorescent Protein (GFP), resulting in reduced steric bulk and thereby a reduction of a potential steric clash of the fluorescent label with other biologically active molecules and/or with interaction partners of the labeled protein or polypeptide. Therefore, the present invention provides means and methods that hold considerable potential for therapy, diagnosis and research.

Thus, the present invention provides a preferably recombinant or synthetic polypeptide having at its C-terminus a recognition sequence for tubulin tyrosine ligase (TTL). Said recognition sequence has preferably at least the amino acid sequence $X_4X_3X_2X_1$, wherein $X_2$ is E, D or C and $X_1$ is E. Said polypeptide is, as described herein, modified to introduce or add said recognition sequence. Said polypeptide has advantageously biological activity. Said polypeptide has preferably a length of more than 19 amino acids, such as 20, 30, 40, 50, 60, 70, 80, 90, 100, 150, 200, 250, or more amino acids in length. Said polypeptide is preferably a polypeptide other than tubulin.

The present invention also provides a method for the production of a functionalized polypeptide comprising
 (a) introducing or adding at the C-terminus of a polypeptide a recognition sequence for tubulin tyrosine ligase;
 (b) contacting the polypeptide obtained in step (a) in the presence of tubulin tyrosine ligase and a compound under conditions suitable for the tubulin tyrosine ligase to functionalize said polypeptide with said compound, wherein said compound having a structure according to Formula I

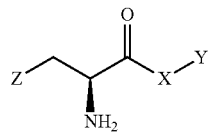

(I)

wherein
 X is O, $NR^1$ or S;
 Y is selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl;
 Z is selected from the group consisting of substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl; and
 $R^1$ is selected from the group consisting of hydrogen, substituted or unsubstituted $(C_1-C_6)$alkyl, substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_6-C_{14})$aryl and substituted or unsubstituted $(C_3-C_{14})$heteroaryl;
 with the proviso that Z is not a substituted or unsubstituted monocyclic six-membered aryl; and
 (c) optionally conjugating a moiety to said functionalized polypeptide obtained in step (b).

Step (c) is also envisaged to be a preferred step of the above method. Hence, in a preferred embodiment, said above method of the present invention further comprises step (c) conjugating a moiety to said functionalized polypeptide obtained in step (b), preferably a moiety as described herein.

As an alternative, the present invention also provides a method for the production of a functionalized polypeptide comprising
 (a') introducing or adding at the C-terminus of a polypeptide a recognition sequence for tubulin tyrosine ligase; and
 (b') contacting the polypeptide obtained in step (a') in the presence of tubulin tyrosine ligase and a compound conjugated to a moiety under conditions suitable for the tubulin tyrosine ligase to functionalize said polypeptide with said compound conjugated to said moiety, wherein said compound having a structure according to Formula I

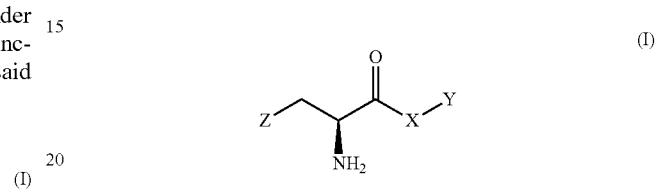

(I)

wherein
 X is O, $NR^1$ or S;
 Y is selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl;
 Z is selected from the group consisting of substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl; and
 $R^1$ is selected from the group consisting of hydrogen, substituted or unsubstituted $(C_1-C_6)$alkyl, substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_6-C_{14})$aryl and substituted or unsubstituted $(C_3-C_{14})$heteroaryl, and
 wherein said moiety is conjugated to the Y-group and/or Z-group, with the proviso that
 (i) said Y group is not hydrogen when conjugated to said moiety;
 (ii) Z is not a substituted or unsubstituted monocyclic six-membered aryl.

Said alternative method allows, so to say, a one-step functionalization of a polypeptide in that tubulin tyrosine ligase functionalizes a polypeptide into which a recognition sequence for tubulin tyrosine ligase is introduced or added at its C-terminus with a compound having a structure according to Formula I conjugated to a moiety. Thus, said method, so to say, simplifies the functionalization in that no extra functionalization step is required, where tubulin tyrosine ligase first adds a compound having a structure according to Formula I to the C-terminus of a polypeptide into which a recognition sequence for tubulin tyrosine ligase is introduced or added in order to then conjugate a moiety to said functionalized polypeptide. Rather, tubulin tyrosine ligase was found by the present inventors to functionalize a polypeptide into which a recognition sequence for tubulin tyrosine ligase is introduced or added at its C-terminus with a compound having a structure according to Formula I already conjugated to a moiety. The moiety may be conjugated to group Y or group Z. In case that the moiety is conjugated to Y, Y is not hydrogen. In some embodiments the moiety may be conjugated to the β-methylene-group of the amino acid or amino acid derivative according to formula I. The moiety is preferably covalently conjugated to group Y, group Z or the β-methylene-group of the amino acid or amino acid derivative according to formula I. The moiety may be conjugated to such group by common methods in the art such as Staudinger reactions (e.g. Staudinger-ligation, Staudinger-Phosphite reaction), strain-promoted cycloadditions, tetrazine ligations, inverse-electron demand Diels-Alder reactions, thiazolidine-forming reactions of aldehydes or ketones with 1,2-aminothiols, oxazolidine-forming reactions of aldehydes or ketones with 1,2-aminoalcohols, acetal-forming reactions of aldehydes or ketones with 1,2-diols, metal-catalyzed, in particular Pd—, Cu, Ni and Fe-catalyzed cross couplings, amide formation and the like. It is also obvious for the skilled person that the group Y, group Z or the β-methylene-group of the amino acid or amino acid derivative according to formula I and/or the moiety may require modification in order to be attached to each other.

Said moiety may be a carrier, a polypeptide, a detectable label, a chemical compound, a nucleic acid, a carbohydrate, or a lipid. The polypeptide can be, in particular, an antibody or fragment thereof selected from the group consisting of a monoclonal antibody, chimeric antibody, humanized antibody, human antibody, scFv, a DART, domain antibody, nanobody, an adnectin, an affibody, an anticalin, a DARPin, or an aptamer. The detectable label may comprise a fluorophore, an enzyme (peroxidase, luciferase), a radioisotope, a fluorescent protein, or a fluorescent dye. The chemical compound can be a small molecule, a polymer, such as a synthetic polymer (PEG) or a therapeutic agent. The nucleic acid can be DNA, RNA, or an aptamer. The moiety and possibilities to attach said moiety to the compound having a structure according to Formula I will be described and discussed in detail below.

As used herein and throughout the entire description, the terms "protein," "peptide" and "polypeptide" are used interchangeably herein, and refer to a polymer of amino acid residues linked together by peptide (amide) bonds. Said term also encompasses fragments of polypeptides. Said fragments have preferably biological activity. Said fragments may have a length of 10, 20, 30, 40, 50, 60, 70, 80, 90, 100, 150, 200, 250, 300, 350, 400, 450 or more amino acids. In some embodiments the terms refer to a protein, peptide, or polypeptide of any size, structure, or function, with the exception of tubulin. In some embodiments the terms refer to a protein, peptide, or polypeptide of any size, structure, or function, including tubulin.

As used herein and throughout the entire description, the term "tubulin" as used herein comprises any isoform (i.e., α-, β-, γ-, δ-, ∈-, ζ-tubulin), mutant, variant or derivative of tubulin. As explained herein, the finding of the present invention is, inter alia, that polypeptides, i.e. polypeptides are functionalized with a compound having a structure according to Formula I by TTL, provided they have a TTL recognition sequence. In other words, the present inventors found that TTL is active on heterologous substrates, such as peptides or polypeptides that merely contain a TTL recognition sequence at their C-terminus, but are otherwise not structurally related to α tubulin. Further, the inventors found that TTL is also able to ligate amino acids or derivatives thereof, different to the natural coupling partner tyrosine, to said polypeptide, wherein said amino acids or amino acid derivatives having a structure according to Formula I.

As used herein and throughout the entire description, "Heterologous substrate" means a peptide or polypeptide on which TTL is active by way of functionalization, but which is not α tubulin.

As used herein and throughout the entire description, "functionalized polypeptide or functionalized protein" means a polypeptide or protein which may or may not be structurally related to α tubulin polypeptide, carrying a TTL recognition sequence at their C-terminus and wherein said TTL recognition sequence has been functionalized by TTL with a compound having a structure according to Formula I. In other words TTL attaches a compound having a structure according to Formula I to the C-terminus of said TTL recognition sequence, which is itself bound to the polypeptide or protein.

As used herein and throughout the entire description, the term "funtionalizing" in all its grammatical forms as used herein means "covalently attaching a compound having a structure according to Formula I" to a polypeptide. Without wishing to be bound by a specific theory, it is envisaged that the TTL adds a compound having a structure according to Formula I to the ultimate C-terminal amino acid of the TTL recognition motif. Said a compound having a structure according to Formula I may already be conjugated to a moiety as described herein. Conjugation of a moiety to a compound having a structure according to Formula I may be done as is known in the art or preferably be done as described herein. Accordingly, it is thus also envisaged that the term "functionalizing" encompassed that tubulin tyrosine ligase functionalizes a polypeptide having a recognition sequences for TTL as described herein with a compound having a structure according to Formula I that is (already) conjugated with a moiety as described herein. This finding of the present inventors was again surprising in that TTL is able to use even a compound having a structure according to Formula I conjugated to large or bulky moieties.

As used herein and throughout the entire description, "a polypeptide or peptide other than tubulin" or "a non-tubulin peptide or polypeptide" encompasses a polypeptide which is not structurally related to α tubulin polypeptide. Such α tubulin polypeptide has preferably an amino acid sequence having a sequence identity of 60% or more, such as 70%, 80%, 90% or 100%, to SEQ ID No. 1.

```
                                                      (SEQ ID NO. 1)
MRECISIHVG QAGVQIGNAC WELYCLEHGI QPDGQMPSDK TIGGGDDSFN    50

TFFSETGAGK HVPRAVFVDL EPTVIDEVRT GTYRQLFHPE QLITGKEDAA   100

NNYARGHYTI GKEIIDLVLD RIRKLADQCT GLQGFLVFHS FGGGTGSGFT   150
```

```
                                                   -continued

SLLMERLSVD  YGKKSKLEFS  IYPAPQVSTA  VVEPYNSILT  THTTLEHSDC    200

AFMVDNEAIY  DICRRNLDIE  RPTYTNLNRL  IGQIVSSITA  SLRFDGALNV    250

DLTEFQTNLV  PYPRIHFPLA  TYAPVISAEK  AYHEQLSVAE  ITNACFEPAN    300

QMVKCDPRHG  KYMACCLLYR  GDVVPKDVNA  AIATIKTKRT  IQFVDWCPTG    350

FKVGINYQPP  TVVPGGDLAK  VQRAVCMLSN  TTAIAEAWAR  LDHKFDLMYA    400

KRAFVHWYVG  EGMEEGEFSE  AREDMAALEK  DYEEVGVDSV  EGEGEEEGEE
```

Thus, such tubulin polypeptides are preferably excluded from a polypeptide of the present invention that is functionalized with a compound having a structure according to Formula I and further modified by conjugation of a moiety to the compound having a structure according to Formula I of the functionalized polypeptide or that is functionalized with a compound having a structure according to Formula I (already) conjugated to a moiety. A variety of sequence based alignment methodologies, which are well known to those skilled in the art, can be used to determine identity among sequences. These include, but not limited to, the local identity/homology algorithm of Smith, F. and Waterman, M. S. (1981) Adv. Appl. Math. 2: 482-89, homology alignment algorithm of Peason, W. R. and Lipman, D. J. (1988) Proc. Natl. Acad. Sci. USA 85: 2444-48, Basic Local Alignment Search Tool (BLAST) described by Altschul, S. F. et al. (1990) J. Mol. Biol. 215: 403-10, or the Best Fit program described by Devereau, J. et al. (1984) Nucleic Acids. Res. 12: 387-95, and the FastA and TFASTA alignment programs, preferably using default settings or by inspection. Alternatively, an alignment may be done manually/visually as follows: the percent identity between an amino acid sequence in question and the amino acid sequence shown in SEQ ID No. 1 (reference sequence) is determined by pairwise alignment in such a way that the maximum identity is obtained between both amino acid sequences. The identical amino acid residues between both amino acid sequences are counted and divided by the total number of residues of the amino acid sequence shown in SEQ ID No. 1 (including positions that do not contain amino acid residues, e.g. one or more gaps) yielding the percentage of identity.

As used herein and throughout the entire description, a protein, peptide, or polypeptide may refer to an individual protein or a collection of proteins. One or more of the amino acids in the polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, a fusion partner for half-life extension, an affinity tags, such as a histidine tag, Flag-tag, streptavidin tag, strep II tag, an intein, a maltose-binding protein, an IgA or IgG Fc portion, protein A or protein G, and other modifications. Other possible chemical modifications of the polypeptide include acylation or acetylation of the amino-terminal end or amidation or esterification of the carboxy-terminal end or, alternatively, on both. The modifications may also affect the amino group in the side chain of lysine or the hydroxyl group of threonine. Other posiible modifications include, e.g., extension of an amino group with polypeptide chains of varying length (e.g., XTEN technology or PASylation®), N-glycosylation, O-glycosylation, and chemical conjugation of carbohydrates, such as hydroxyethyl starch (e.g., HESylation®) or polysialic acid (e.g., PolyXen® technology). Chemical modifications such as alkylation (e. g., methylation, propylation, butylation), arylation, and etherification may be possible and are also envisaged. It is however preferred that the modification does not abolish the capability of TTL to recognize the TTL recognition sequence and/or to functionalize the polypeptide of the invention with a compound having a structure according to Formula I. A protein, peptide, or polypeptide may also be a single molecule or may be a multi-molecular complex. A protein, peptide, or polypeptide may be just a fragment of a naturally occurring protein or peptide, as long as it exhibits biological activity as defined herein As used herein and throughout the entire description, the term "Tubulin tyrosine ligase", abbreviated sometimes herein as "TTL", encompasses polypeptides that are capable of functionalizing polypeptides, i.e. covalently attaching a compound having a structure according to Formula I to a polypeptide. Preferably a TTL is capable of functionalizing a polypeptide at the C-terminus of said polypeptide with a compound having a structure according to Formula I. For that action it is preferred that said polypeptide comprises a recognition sequence for TTL. Said term encompasses TTLs from eukaryotes, preferably mammals, more preferably from humans. A preferred TTL is shown in SEQ ID No: 10. Also encompassed by said term is a TTL that has 70%, 80%, 90% or 95% or more identity over its entire amino acid sequence with the amino acid sequence of the TTL shown in SEQ ID No: 10. Preferably, such polypeptides having an amino acid sequence which shares an identity as described before have TTL activity. TTL activity can be tested as is known in the art or described herein. The percentage of sequence identity can, for example, be determined herein as described above. Preferably the amino acid sequence shown in SEQ ID No: 10 is used as reference in a pairwise comparison. It is calculated as the percentage of numbers of "positives" (homologous amino acids) indicated as result in the BLASTP program output divided by the total number of amino acids selected by the program for the alignment.

As used herein and throughout the entire description, the term "covalently bonded" is used herein interchangeably with the terms "covalently attached to" and "covalently joined" and refers to a type of chemical bond involving the sharing of two electron pairs between atoms. Without wishing to be bound by a specific theory, it is envisaged that the compound having a structure according to Formula I is covalently attached to the TTL recognition sequence by the action of the TTL, so that the compound having a structure according to Formula I is attached to the ultimate C-terminal amino acid of the recognition sequence, which is designated $X_1$ herein. The resulting C-terminal amino acid sequence will then be $X_4X_3X_2X_1X_0$, wherein $X_0$ refers to a compound having a structure according to Formula I.

As used herein and throughout the entire description, the term "alkyl" refers to a monoradical of a saturated straight or branched hydrocarbon. Preferably, the alkyl group comprises from 1 to 12 (such as 1 to 10) carbon atoms, i.e., 1, 2, 3, 4, 5, 6, 7, 8, 9, 10, 11, or 12 carbon atoms (such as 1, 2, 3, 4, 5, 6, 7, 8, 9, or 10 carbon atoms), more preferably 1 to 8 carbon atoms, such as 1 to 6 or 1 to 4 carbon atoms. In some embodiments, the alkyl group employed in the invention contains 1-20 carbon atoms ($C_{1-20}$ alkyl). In another embodiment, the alkyl group employed contains 1-15 carbon atoms ($C_{1-15}$ alkyl). In another embodiment, the alkyl group employed contains 1-10 carbon atoms ($C_{1-20}$ alkyl). In another embodiment, the alkyl group employed contains 1-8 carbon atoms ($C_{1-8}$ alkyl). In another embodiment, the alkyl group employed contains 1-6 carbon atoms ($C_{1-6}$ alkyl). In another embodiment, the alkyl group employed contains 1-5 carbon atoms ($C_{1-5}$-alkyl). In another embodiment, the alkyl group employed contains 1-4 carbon atoms ($C_{1-4}$ alkyl). In another embodiment, the alkyl group employed contains 1-3 carbon atoms ($C_{1-3}$ alkyl). In another embodiment, the alkyl group employed contains 1-2 carbon atoms ($C_{1-2}$ alkyl). Examples of alkyl radicals include, but are not limited to, methyl, ethyl, propyl, iso-propyl, butyl, iso-butyl, tert-butyl, n-pentyl, iso-pentyl, sec-pentyl, neo-pentyl, 1,2-dimethyl-propyl, iso-amyl, n-hexyl, iso-hexyl, sec-hexyl, n-heptyl, iso-heptyl, n-octyl, 2-ethyl-hexyl, n-nonyl, n-decyl, n-undecyl, n-dodecyl, and the like, which may bear one or more substituents. Alkyl group substituents include, but are not limited to, any of the substituents described herein, that result in the formation of a stable moiety. In some embodiments the alkyl chain is a linear. In some embodiments the alkyl chain is branched. In some embodiments the alkyl chain is substituted. In some embodiment the alkyl chain is unsubstituted. In some embodiments the alkyl chain is linear and substituted or unsubstituted. In some embodiments the alkyl chain is branched and substituted or unsubstituted.

As used herein and throughout the entire description, the term term "alkylene" refers to a diradical of a saturated straight or branched hydrocarbon. Preferably, the alkylene comprises from 1 to 10 carbon atoms, i.e., 1, 2, 3, 4, 5, 6, 7, 8, 9, or 10 carbon atoms, more preferably 1 to 8 carbon atoms, such as 1 to 6 or 1 to 4 carbon atoms. Exemplary alkylene groups include methylene, ethylene (i.e., 1,1-ethylene, 1,2-ethylene), propylene (i.e., 1,1-propylene, 1,2-propylene (—CH(CH$_3$)CH$_2$—), 2,2-propylene (—C(CH$_3$)$_2$—), and 1,3-propylene), the butylene isomers (e.g., 1,1-butylene, 1,2-butylene, 2,2-butylene, 1,3-butylene, 2,3-butylene (cis or trans or a mixture thereof), 1,4-butylene, 1,1-iso-butylene, 1,2-iso-butylene, and 1,3-iso-butylene), the pentylene isomers (e.g., 1,1-pentylene, 1,2-pentylene, 1,3-pentylene, 1,4-pentylene, 1,5-pentylene, 1,1-iso-pentylene, 1,1-sec-pentyl, 1,1-neo-pentyl), the hexyleneisomers (e.g., 1,1-hexylene, 1,2-hexylene, 1,3-hexylene, 1,4-hexylene, 1,5-hexylene, 1,6-hexylene, and 1,1-isohexylene), and the like. Alkylene groups may be cyclic or acyclic, branched or unbranched, substituted or unsubstituted. Alkylene group substituents include, but are not limited to, any of the substituents described herein, that result in the formation of a stable moiety.

As used herein and throughout the entire description, the term "halogen" or "halo" means fluoro, chloro, bromo, or iodo.

As used herein and throughout the entire description, the term "azido" means N$_3$.

As used herein and throughout the entire description, the term "optionally substituted" or "substituted" indicates that one or more (such as 1 to the maximum number of hydrogen atoms bound to a group, e.g., 1, 2, 3, 4, 5, 6, 7, 8, 9, or up to 10, such as between 1 to 5, 1 to 4, or 1 to 3, or 1 or 2) hydrogen atom(s) may be replaced with a group different from hydrogen such as alkyl (preferably, $C_{1-6}$ alkyl), alkenyl (preferably, $C_{2-6}$ alkenyl), alkynyl (preferably, $C_{2-6}$ alkynyl), aryl (preferably, 3- to 14-membered aryl), heteroaryl (preferably, 3- to 14-membered heteroaryl), cycloalkyl (preferably, 3- to 14-membered cycloalkyl), heterocyclyl (preferably, 3- to 14-membered heterocyclyl), halogen, —CN, azido, —NO$_2$, —OR$^{71}$, —N(R$^{72}$)(R$^{73}$), —ON(R$^{72}$)(R$^{73}$), —N$^+$(—O$^-$)(R$^{72}$)(R$^{73}$),—S(O)$_{0-2}$R$^{71}$, —S(O)$_{0-2}$OR$^{71}$, —OS(O)$_{0-2}$R$^{71}$, —OS(O)$_{0-2}$OR$^{71}$, —S(O)$_{0-2}$N(R$^{72}$)(R$^{73}$), —OS(O)$_{0-2}$N(R$^{72}$)(R$^{73}$), —N(R$^{71}$)S(O)$_{0-2}$R$^{71}$, —NR$^{71}$S(O)$_{0-2}$OR$^{71}$, —NR$^{71}$S(O)$_{0-2}$N(R$^{72}$)(R$^{73}$), —C(=W$^1$)R$^{71}$, —C(=W$^1$)W$^1$R$^{71}$, —W$^1$C(=W$^1$)R$^{71}$, and —W$^1$C(=W$^1$)W$^1$R$^{71}$;

wherein R$^{71}$, R$^{72}$, and R$^{73}$ are independently selected from the group consisting of —H, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl, wherein each of the alkyl, alkenyl, alkynyl, cycloalkyl, aryl, heteroaryl, and heterocyclyl groups is optionally substituted with one, two or three substituents selected from the group consisting of $C_{1-3}$ alkyl, halogen, —CF$_3$, —CN, azido, —NO$_2$, —OH, —O($C_{1-3}$ alkyl), —S($C_{1-3}$ alkyl), —NH$_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{2-z}$($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl; W$^1$ is independently selected from O, S, and NR$^{84}$, wherein R$^{84}$ is —H or $C_{1-3}$ alkyl.

As used herein and throughout the entire description, the term "alkenyl" refers to a monoradical of an unsaturated straight or branched hydrocarbon having at least one carbon-carbon double bond. Generally, the maximal number of carbon-carbon double bonds in the alkenyl group can be equal to the integer which is calculated by dividing the number of carbon atoms in the alkenyl group by 2 and, if the number of carbon atoms in the alkenyl group is uneven, rounding the result of the division down to the next integer. For example, for an alkenyl group having 9 carbon atoms, the maximum number of carbon-carbon double bonds is 4. Preferably, the alkenyl group has 1 to 4, i.e., 1, 2, 3, or 4, carbon-carbon double bonds. Preferably, the alkenyl group comprises from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkenyl group comprises from 2 to 10 carbon atoms and 1, 2, 3, 4, or 5 carbon-carbon double bonds, more preferably it comprises 2 to 8 carbon atoms and 1, 2, 3, or 4 carbon-carbon double bonds, such as 2 to 6 carbon atoms and 1, 2, or 3 carbon-carbon double bonds or 2 to 4 carbon atoms and 1 or 2 carbon-carbon double bonds. In certain embodiments, the alkenyl group employed in the invention contains 2-20 carbon atoms ($C_{2-20}$ alkenyl). In some embodiments, the alkenyl group employed in the invention contains 2-15 carbon atoms ($C_{2-15}$ alkenyl). In another embodiment, the alkenyl group employed contains 2-10 carbon atoms ($C_{2-10}$ alkenyl). In still other embodiments, the alkenyl group contains 2-8 carbon atoms ($C_{2-8}$ alkenyl). In yet other embodiments, the alkenyl group contains 2-6 carbons ($C_{2-6}$ alkenyl). In yet other embodiments, the alkenyl group contains 2-5 carbons ($C_{2-5}$ alkenyl). In yet other embodiments, the alkenyl group contains 2-4 carbons ($C_{2-4}$ alkenyl). In yet other embodiments, the alkenyl group contains 2-3 carbons ($C_{2-3}$ alkenyl). In yet other embodiments, the alkenyl group contains 2 carbons ($C_2$ alkenyl). The carbon-carbon double bond(s) may be in cis (Z) or trans (E) configuration. Exemplary alkenyl groups include vinyl, 1-propenyl, 2-propenyl (i.e., allyl), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, and the like. If an alkenyl group is attached to a nitrogen atom, the double bond cannot be alpha to the nitrogen atom. In some embodiments the alkenyl chain is a linear. In some embodiments the alkenyl chain is branched. In some embodiments the alkenyl chain is substituted. In some embodiment the alkenyl chain is unsubstituted. In some embodiments the alkenyl chain is linear and substituted or unsubstituted. In some embodiments the alkenyl chain is branched and substituted or unsubstituted. Alkenyl group substituents include, but are not limited to, any of the substituents described herein, that result in the formation of a stable moiety.

As used herein and throughout the entire description, the term "alkenylene" refers to a diradical of an unsaturated straight or branched hydrocarbon having at least one carbon-carbon double bond. Generally, the maximal number of carbon-carbon double bonds in the alkenylene group can be equal to the integer which is calculated by dividing the number of carbon atoms in the alkenylene group by 2 and, if the number of carbon atoms in the alkenylene group is uneven, rounding the result of the division down to the next integer. For example, for an alkenylene group having 9 carbon atoms, the maximum number of carbon-carbon double bonds is 4. Preferably, the alkenylene group has 1 to 4, i.e., 1, 2, 3, or 4, carbon-carbon double bonds. Preferably, the alkenylene group comprises from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkenylene group comprises from 2 to 10 carbon atoms and 1, 2, 3, 4, or 5 carbon-carbon double bonds, more preferably it comprises 2 to 8 carbon atoms and 1, 2, 3, or 4 carbon-carbon double bonds, such as 2 to 6 carbon atoms and 1, 2, or 3 carbon-carbon double bonds or 2 to 4 carbon atoms and 1 or 2 carbon-carbon double bonds. The carbon-carbon double bond(s) may be in cis (Z) or trans (E) configuration. Exemplary alkenylene groups include ethen-1,2-diyl, vinyliden, 1-propen-1,2-diyl, 1-propen-1,3-diyl, 1-propen-2,3-diyl, allyliden, 1-buten-1,2-diyl, 1-buten-1,3-diyl, 1-buten-1,4-diyl, 1-buten-2,3-diyl, 1-buten-2,4-diyl, 1-buten-3,4-diyl, 2-buten-1,2-diyl, 2-buten-1,3-diyl, 2-buten-1,4-diyl, 2-buten-2,3-diyl, 2-buten-2,4-diyl, 2-buten-3,4-diyl, and the like. If an alkenylene group is attached to a nitrogen atom, the double bond cannot be alpha to the nitrogen atom. Alkenylene groups may be cyclic or acyclic, branched or unbranched, substituted or unsubstituted. Alkenylene group substituents include, but are not limited to, any of the substituents described herein, that result in the formation of a stable moiety.

As used herein and throughout the entire description, the term "alkynyl" refers to a monoradical of an unsaturated straight or branched hydrocarbon having at least one carbon-carbon triple bond. Generally, the maximal number of carbon-carbon triple bonds in the alkynyl group can be equal to the integer which is calculated by dividing the number of carbon atoms in the alkynyl group by 2 and, if the number of carbon atoms in the alkynyl group is uneven, rounding the result of the division down to the next integer. For example, for an alkynyl group having 9 carbon atoms, the maximum number of carbon-carbon triple bonds is 4. Preferably, the alkynyl group has 1 to 4, i.e., 1, 2, 3, or 4, more preferably 1 or 2 carbon-carbon triple bonds. Preferably, the alkynyl group comprises from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkynyl group comprises from 2 to 10 carbon atoms and 1, 2, 3, 4, or 5 (preferably 1, 2, or 3) carbon-carbon triple bonds, more preferably it comprises 2 to 8 carbon atoms and 1, 2, 3, or 4 (preferably 1 or 2) carbon-carbon triple bonds, such as 2 to 6 carbon atoms and 1, 2 or 3 carbon-carbon triple bonds or 2 to 4 carbon atoms and 1 or 2 carbon-carbon triple bonds. In certain embodiments, the alkynyl group employed in the invention contains 2-20 carbon atoms ($C_{2-20}$ alkynyl). In some embodiments, the alkynyl group employed in the invention contains 2-15 carbon atoms ($C_{215}$ alkynyl). In another embodiment, the alkynyl group employed contains 2-10 carbon atoms ($C_{2-10}$ alkynyl). In still other embodiments, the alkynyl group contains 2-8 carbon atoms ($C_{2-8}$ alkynyl). In still other embodiments, the alkynyl group contains 2-6 carbon atoms ($C_{2-6}$ alkynyl). In still other embodiments, the alkynyl group contains 2-5 carbon atoms ($C_{2-5}$ alkynyl). In still other embodiments, the alkynyl group contains 2-4 carbon atoms ($C_{2-4}$ alkynyl). In still other embodiments, the alkynyl group contains 2-3 carbon atoms ($C_{2-3}$ alkynyl). In still other embodiments, the alkynyl group contains 2 carbon atoms ($C_2$ alkynyl). Exemplary alkynyl groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonylyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, 9-decynyl, and the like, which may bear one or more substituents. Alkynyl group substituents include, but are not limited to, any of the substituents described herein, that result in the formation of a stable moiety. If an alkynyl group is attached to a nitrogen atom, the triple bond cannot be alpha to the nitrogen atom. In some embodiments the alkynyl chain is a linear. In some embodiments the alkynyl chain is branched. In some embodiments the alkynyl chain is substituted. In some embodiment the alkynyl chain is unsubstituted. In some embodiments the alkynyl chain is linear and substituted or unsubstituted. In some embodiments the alkynyl chain is branched and substituted or unsubstituted.

As used herein and throughout the entire description, the term "alkynylene" refers to a diradical of an unsaturated straight or branched hydrocarbon having at least one carbon-carbon triple bond. Generally, the maximal number of carbon-carbon triple bonds in the alkynylene group can be equal to the integer which is calculated by dividing the number of carbon atoms in the alkynylene group by 2 and, if the number of carbon atoms in the alkynylene group is uneven, rounding the result of the division down to the next integer. For example, for an alkynylene group having 9 carbon atoms, the maximum number of carbon-carbon triple bonds is 4. Preferably, the alkynylene group has 1 to 4, i.e., 1, 2, 3, or 4, more preferably 1 or 2 carbon-carbon triple bonds. Preferably, the alkynylene group comprises from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkynylene group comprises from 2 to 10 carbon atoms and 1, 2, 3, 4, or 5 (preferably 1, 2, or 3) carbon-carbon triple bonds, more preferably it comprises 2 to 8 carbon atoms and 1, 2, 3, or 4 (preferably 1 or 2) carbon-carbon triple bonds, such as 2 to 6 carbon atoms and 1, 2 or 3 carbon-carbon triple bonds or 2 to 4 carbon atoms and 1 or 2 carbon-carbon triple bonds. Exemplary alkynylene groups include ethyn-1,2-diyl, 1-propyn-1,3-diyl, 1-propyn-3,3-diyl, 1-butyn-1,3-diyl, 1-butyn-1,4-diyl, 1-butyn-3,4-diyl, 2-butyn-1,4-diyl and the like. If an alkynylene group is attached to a nitrogen atom, the triple bond cannot be alpha to the nitrogen atom. Alkynylene groups may be cyclic or acyclic, branched or unbranched, substituted or unsubstituted. Alkynylene group substituents include, but are not limited to, any of the substituents described herein, that result in the formation of a stable moiety.

As used herein and throughout the entire description, the term "cycloalkyl" or "cycloaliphatic" or "carbocyclic" or "carbocycle" represents cyclic non-aromatic versions of "alkyl" and "alkenyl" with preferably 3 to 14 carbon atoms, such as 3 to 10 carbon atoms, i.e., 3, 4, 5, 6, 7, 8, 9, or 10 carbon atoms, more preferably 3 to 8 carbon atoms, even more preferably 3 to 7 carbon atoms. In certain embodiments, the cycloalkyl group employed in the invention contains 3-14 carbon atoms ($C_{3-14}$ cycloalkyl). In certain embodiments, the cycloalkyl group employed in the invention contains 3-12 carbon atoms ($C_{3-12}$ cycloalkyl). In another embodiment, the cycloalkyl group employed in the invention contains 3-10 carbon atoms ($C_{3-10}$ cycloalkyl). In another embodiment, the cycloalkyl group employed in the invention contains 3-8 carbon atoms ($C_{3-8}$ cycloalkyl). In another embodiment, the cycloalkyl group employed in the invention contains 3-7 carbon atoms ($C_{3-7}$ cycloalkyl). In another embodiment, the cycloalkyl group employed in the invention contains 3-6 carbon atoms ($C_{3-6}$ cycloalkyl). In another embodiment, the cycloalkyl group employed in the invention contains 3-5 carbon atoms ($C_{3-5}$ cycloalkyl). In another embodiment, the cycloalkyl group employed in the invention contains 3-4 carbon atoms ($C_{3-4}$ cycloalkyl). In another embodiment, the cycloalkyl group employed in the invention contains 3 carbon atoms ($C_3$ cycloalkyl). Exemplary cycloalkyl groups include cyclopropyl, cyclopropenyl, cyclobutyl, cyclobutenyl, cyclopentyl, cyclopentenyl, cyclohexyl, cyclohexenyl, cycloheptyl, cycloheptenyl, cyclooctyl, cyclooctenyl, cyclononyl, cyclononenyl, cylcodecyl, cylcodecenyl, and adamantyl. The term "cycloalkyl" is also meant to include bicyclic and tricyclic versions thereof. If bicyclic rings are formed it is preferred that the respective rings are connected to each other at two adjacent carbon atoms, however, alternatively the two rings are connected via the same carbon atom, i.e., they form a spiro ring system or they form "bridged" ring systems. Preferred examples of cycloalkyl include $C_3$-$C_8$-cycloalkyl, in particular cyclopropyl, cyclobutyl, cyclopentyl, cyclohexyl, cycloheptyl, cyclooctyl, spiro[3,3]heptyl, spiro[3,4]octyl, spiro[4,3]octyl, bicyclo[4.1.0]heptyl, bicyclo[3.2.0]heptyl, bicyclo[2.2.1]heptyl, bicyclo[2.2.2]octyl, bicyclo[5.1.0]octyl, and bicyclo[4.2.0]octyl. Cycloalkyl group substituents include, but are not limited to, any of the substituents described herein, that result in the formation of a stable moiety.

As used herein and throughout the entire description, the term "cyclopropylene" means a cyclopropyl group as defined above in which one hydrogen atom has been removed resulting in a diradical. The cyclopropylene may link two atoms or moieties via the same carbon atom (1,1-cyclopropylene, i.e., a geminal diradical) or via two carbon atoms (1,2-cyclopropylene).

As used herein and throughout the entire description, the term "aryl" or "aromatic ring" as used herein, refers to an aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_{4-20}$ aromatic ring system having one, two, or three aromatic rings which include, but are not limited to, phenyl, biphenyl, naphthyl, and the like, which may bear one or more substituents. Preferably, the aryl group contains 3 to 14 (e.g., 5 to 10, such as 5, 6, or 10) carbon atoms, more preferably 6 to 10 carbon atoms, which can be arranged in one ring (e.g., phenyl) or two or more condensed rings (e.g., naphthyl). Exemplary aryl groups include cyclopropenylium, cyclopentadienyl, phenyl, indenyl, naphthyl, azulenyl, fluorenyl, anthryl, and phenanthryl. Preferably, "aryl" refers to a monocyclic ring containing 6 carbon atoms or an aromatic bicyclic ring system containing 10 carbon atoms. Preferred examples are phenyl and naphthyl. In certain embodiments, the aryl group employed in the invention contains 3-20 carbon atoms ($C_{3-20}$ aryl). In certain embodiments, the aryl group employed in the invention contains 3-18 carbon atoms ($C_{3-18}$ aryl). In another embodiment, the aryl group employed in the invention contains 3-16 carbon atoms ($C_{3-16}$ aryl). In another embodiment, the aryl group employed in the invention contains 6-16 carbon atoms ($C_{6-16}$ aryl). In another embodiment, the aryl group employed in the invention contains 7-16 carbon atoms ($C_{7-16}$ aryl). In another embodiment, the aryl group employed in the invention contains 6-14 carbon atoms ($C_{6-14}$ aryl). In another embodiment, the aryl group employed in the invention contains 7-14 carbon atoms ($C_{7-14}$ aryl). In another embodiment, the aryl group employed in the invention contains 6-12 carbon atoms ($C_6$-12 aryl).). In another embodiment, the aryl group employed in the invention contains 7-12 carbon atoms ($C_{7-12}$ aryl). In another embodiment, the aryl group employed in the invention contains 6-11 carbon atoms ($C_{6-11}$ aryl). In another embodiment, the aryl group employed in the invention contains 7-11 carbon atoms ($C_{7-11}$ aryl). In another embodiment, the aryl group employed in the invention contains 6-10 carbon atoms ($C_{6-10}$ aryl). In another embodiment, the aryl group employed in the invention contains 7-10 carbon atoms ($C_{7-10}$ aryl). In another embodiment, the aryl group employed in the invention contains 6-8 carbon atoms ($C_{6-8}$ aryl). In another embodiment, the aryl group employed in the invention contains 6 carbon atoms ($C_6$ aryl). In another embodiment, the aryl group employed in the invention contains 10 carbon atoms ($C_{10}$ aryl). In some embodiments Z is not a substituted monocyclic six-membered aryl or unsubstituted monocyclic six-membered aryl. In some embodiments Z is not a substituted phenyl or unsubstituted phenyl. In some embodiments Z is not a phenyl substituted with 1, 2, 3, 4 or 5 substituents selected from the group consisting of —$NO_2$, —$N_3$, halogen, —$NH_2$, hydroxyl, —$OR^{11}$ and —C(=O)$R^{11}$, wherein $R^{11}$ is hydrogen, substituted alkyl or substituted alkynyl. Aryl substituents include, but are not limited to, any of the substituents described herein, that result in the formation of a stable moiety.

As used herein and throughout the entire description, the term "arylene," as used herein refers to an aryl biradical derived from an aryl group, as defined herein, by removal of two hydrogen atoms. Arylene groups may be substituted or unsubstituted. Arylene group substituents include, but are not limited to, any of the substituents described herein, that result in the formation of a stable moiety. Additionally, arylene groups may be incorporated as a linker group into an alkylene, alkenylene, alkynylene, heteroalkylene, heteroalkenylene, or heteroalkynylene group, as defined herein.

As used herein and throughout the entire description, the term "heteroaryl" or "heteroaromatic ring" means an aryl group as defined above in which one or more carbon atoms in the aryl group are replaced by heteroatoms of O, S, or N. Preferably, the heteroaryl group contains 3 to 14 carbon atoms. Preferably, heteroaryl refers to a five or six-membered aromatic monocyclic ring wherein 1, 2, or 3 carbon atoms are replaced by the same or different heteroatoms of O, N, or S. Alternatively, it means an aromatic bicyclic or tricyclic ring system wherein 1, 2, 3, 4, or 5 carbon atoms are replaced with the same or different heteroatoms of O, N, or S. Preferably, in each ring of the heteroaryl group the maximum number of O atoms is 1, the maximum number of S atoms is 1, and the maximum total number of O and S atoms is 2. In certain embodiments, the heteroaryl group employed in the invention is a five membered aromatic monocyclic ring wherein 1, 2, or 3 carbon atoms are replaced by the same or different heteroatoms of O, N, or S. In certain embodiments, the heteroaryl group employed in the invention is a five membered aromatic monocyclic ring wherein 1, 2, or 3 carbon atoms are replaced by the same or different heteroatoms of O. In certain embodiments, the heteroaryl group employed in the invention is a five membered aromatic monocyclic ring wherein 1, 2, or 3 carbon atoms are replaced by the same or different heteroatoms of O and N. In certain embodiments, the heteroaryl group employed in the invention is a five membered aromatic monocyclic ring wherein 1, 2, or 3 carbon atoms are replaced by the same or different heteroatoms of O and S. In certain embodiments, the heteroaryl group employed in the invention is a five membered aromatic monocyclic ring wherein 1, 2, or 3 carbon atoms are replaced by the same or different heteroatoms of N and S. In certain embodiments, the heteroaryl group employed in the invention is a six membered aromatic monocyclic ring wherein 1, 2, or 3 carbon atoms are replaced by the same or different heteroatoms of O, S or N. In certain embodiments, the heteroaryl group employed in the invention is a six membered aromatic monocyclic ring wherein 1, 2, or 3 carbon atoms are replaced by N. In certain embodiments, the heteroaryl group employed in the invention is an aromatic bicyclic system wherein 1, 2, 3, 4, or 5 carbon atoms are replaced with the same or different heteroatoms of O, N, or S. In certain embodiments, the heteroaryl group employed in the invention is an aromatic bicyclic system wherein 1 carbon atom is replaced with O. In certain embodiments, the heteroaryl group employed in the invention is an aromatic bicyclic system wherein 1 carbon atom is replaced with N. In some embodiments, the heteroaryl group is substituted or unsubstituted indolyl. In certain embodiments, the heteroaryl group employed in the invention is an aromatic bicyclic system wherein 2 carbon atoms are replaced with N. In some embodiments, the heteroaryl group is substituted or unsubstituted 7-azaindolyl. In some embodiments, the heteroaryl group is substituted or unsubstituted 6-azaindolyl. In some embodiments, the heteroaryl group is substituted or unsubstituted 5-azaindolyl. In some embodiments, the heteroaryl group is substituted or unsubstituted 4-azaindolyl. In some embodiments, the heteroaryl group is substituted or unsubstituted imidazolyl. In certain embodiments, the heteroaryl group employed in the invention is an aromatic bicyclic system wherein 3 carbon atoms are replaced with N, preferably a substituted or unsubstituted diazaindolyl group. Exemplary heteroaryl groups include furanyl, thienyl, oxazolyl, isoxazolyl, oxadiazolyl (1,2,5- and 1,2,3-), pyrrolyl, imidazolyl, pyrazolyl, triazolyl (1,2,3- and 1,2,4-), tetrazolyl, thiazolyl, isothiazolyl, thiadiazolyl (1,2,3- and 1,2,5-), pyridyl, pyrimidinyl, pyrazinyl, triazinyl (1,2,3-, 1,2,4-, and 1,3,5-), benzofuranyl (1- and 2-), indolyl, azaindolyl (4-, 5-6- and 7-), diazaindolyl, isoindolyl, benzothienyl (1- and 2-), 1H-indazolyl, benzimidazolyl, benzoxazolyl, indoxazinyl, benzisoxazolyl, benzothiazolyl, benzisothiazolyl, benzotriazolyl, quinolinyl, isoquinolinyl, benzodiazinyl, quinoxalinyl, quinazolinyl, benzotriazinyl (1,2,3- and 1,2,4-benzotriazinyl), pyridazinyl, phenoxazinyl, thiazolopyridinyl, pyrrolothiazolyl, phenothiazinyl, isobenzofuranyl, chromenyl, xanthenyl, phenoxathiinyl, pyrrolizinyl, indolizinyl, indazolyl, purinyl, quinolizinyl, phthalazinyl, naphthyridinyl (1,5-, 1,6-, 1,7-, 1,8-, and 2,6-), cinnolinyl, pteridinyl, carbazolyl, phenanthridinyl, acridinyl, perimidinyl, phenanthrolinyl (1,7-, 1,8-, 1,10-, 3,8-, and 4,7-), phenazinyl, oxazolopyridinyl, isoxazolopyridinyl, pyrrolooxazolyl, pyrrolopyrrolyl, and the like, which may bear one or more substituents. Heteroaryl substituents include, but are not limited to, any of the substituents described herein, that result in the formation of a stable moiety. Exemplary 5- or 6-membered heteroaryl groups include furanyl, thienyl, oxazolyl, isoxazolyl, oxadiazolyl (1,2,5- and 1,2,3-), pyrrolyl, imidazolyl, pyrazolyl, triazolyl (1,2,3- and 1,2,4-), thiazolyl, isothiazolyl, thiadiazolyl (1,2,3- and 1,2,5-), pyridyl, pyrimidinyl, pyrazinyl, triazinyl (1,2,3-, 1,2,4-, and 1,3,5-), and pyridazinyl. Exemplary bicyclic heteroaryl groups 7-azaindolyl, 6-azaindolyl, 5-azaindolyl, 4-azaindolyl, diazaindolyl and indolyl.

As used herein and throughout the entire description, the term "diazaindolyl" or "diazaindole" refers to a compound having an indole core structure, wherein 2 carbon atoms of the annulated phenylring are replaced by N. Preferably the carbon atoms 4, 5, 6 and/or 7 of the indole core are replaced by N. Preferably the carbon atoms 4 and 5 of the indole core are replaced by N. Preferably the carbon atoms 4 and 6 of the indole core are replaced by N. Preferably the carbon atoms 4 and 7 of the indole core are replaced by N. Preferably the carbon atoms 5 and 6 of the indole core are replaced by N. Preferably the carbon atoms 6 and 7 of the indole core are replaced by N. Preferably the carbon atoms 5 and 7 of the indole core are replaced by N. In some embodiments the diazaindolyl is substituted. In some embodiments the diazaindolyl is unsubstituted.

As used herein and throughout the entire description, the term "heteroarylene," as used herein, refers to a biradical derived from a heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, that result in the formation of a stable moiety.

As used herein and throughout the entire description, the terms "arylalkyl" and "heteroarylalkyl" are meant to include those radicals in which an aryl group and heteroaryl group, respectively, is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). Preferably the Arylalkyl is a substituted or unsubstituted ($C_6$-$C_{14}$)aryl($C_1$-$C_6$)alkyl Preferably the Arylalkyl is a substituted or unsubstituted ($C_6$-$C_{10}$)aryl($C_1$-$C_6$)alkyl. Preferably the Heteroarylalkyl is a substituted or unsubstituted ($C_3$-$C_{14}$)heteroaryl($C_1$-$C_6$)alkyl. Preferably the Heteroarylalkyl is a substituted or unsubstituted ($C_3$-$C_{10}$)heteroaryl($C_1$-$C_6$)alkyl. In some embodiments the alkyl chain is a linear. In some embodiments the alkyl chain is branched. In some embodiments the alkyl chain is substituted. In some embodiments the alkyl chain is unsubstituted. In some embodiments the alkyl chain is linear and substituted or unsubstituted. In some embodiments the alkyl chain is branched and substituted or unsubstituted.

As used herein and throughout the entire description, the term "heterocyclyl" or "heterocyclic ring" or "heterocycle" refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. The heterocyclic group may be substituted or unsubstituted. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Preferably, in each ring of the heterocyclyl group the maximum number of O atoms is 1, the maximum number of S atoms is 1, and the maximum total number of O and S atoms is 2. The term "heterocyclyl" is also meant to encompass partially or completely hydrogenated forms (such as dihydro, tetrahydro or perhydro forms) of the above-mentioned heteroaryl groups. Exemplary heterocyclyl groups include morpholino, isochromanyl, chromanyl, pyrrolidinyl, imidazolidinyl, pyrazolidinyl, piperidinyl, piperazinyl, indolinyl, isoindolinyl, di- and tetrahydrofuranyl, di- and tetrahydrothienyl, di- and tetrahydrooxazolyl, di- and tetrahydroisoxazolyl, di- and tetrahydrooxadiazolyl (1,2,5- and 1,2,3-), dihydropyrrolyl, dihydroimidazolyl, dihydropyrazolyl, di- and tetrahydrotriazolyl (1,2,3- and 1,2,4-), di- and tetrahydrothiazolyl, di- and tetrahydrothiazolyl, di- and tetrahydrothiadiazolyl (1,2,3- and 1,2,5-), di- and tetrahydropyridyl, di- and tetrahydropyrimidinyl, di- and tetrahydropyrazinyl, di- and tetrahydrotriazinyl (1,2,3-, 1,2,4-, and 1,3,5-), di- and tetrahydrobenzofuranyl (1- and 2-), di- and tetrahydroindolyl, di- and tetrahydroisoindolyl, di- and tetrahydrobenzothienyl (1- and 2), di- and tetrahydro-1H-indazolyl, di- and tetrahydrobenzimidazolyl, di- and tetrahydrobenzoxazolyl, di- and tetrahydroindoxazinyl, di- and tetrahydrobenzisoxazolyl, di- and tetrahydrobenzothiazolyl, di- and tetrahydrobenzisothiazolyl, di- and tetrahydrobenzotriazolyl, di- and tetrahydroquinolinyl, di- and tetrahydroisoquinolinyl, di- and tetrahydrobenzodiazinyl, di- and tetrahydroquinoxalinyl, di- and tetrahydroquinazolinyl, di- and tetrahydrobenzotriazinyl (1,2,3- and 1,2,4-), di- and tetrahydropyridazinyl, di- and tetrahydrophenoxazinyl, di- and tetrahydrothiazolopyridinyl (such as 4,5,6-7-tetrahydro[1,3]thiazolo[5,4-c]pyridinyl or 4,5,6-7-tetrahydro[1,3]thiazolo[4,5-c]pyridinyl, e.g., 4,5,6-7-tetrahydro[1,3]thiazolo[5,4-c]pyridin-2-yl or 4,5,6-7-tetrahydro[1,3]thiazolo[4,5-c]pyridin-2-yl), di- and tetrahydropyrrolothiazolyl (such as 5,6-dihydro-4H-pyrrolo[3,4-d][1,3]thiazolyl), di- and tetrahydrophenothiazinyl, di- and tetrahydroisobenzofuranyl, di- and tetrahydrochromenyl, di- and tetrahydroxanthenyl, di- and tetrahydrophenoxathiinyl, di- and tetrahydropyrrolizinyl, di- and tetrahydroindolizinyl, di- and tetrahydroindazolyl, di- and tetrahydropurinyl, di- and tetrahydroquinolizinyl, di- and tetrahydrophthalazinyl, di- and tetrahydronaphthyridinyl (1,5-, 1,6-, 1,7-, 1,8-, and 2,6-), di- and tetrahydrocinnolinyl, di- and tetrahydropteridinyl, di- and tetrahydrocarbazolyl, di- and tetrahydrophenanthridinyl, di- and tetrahydroacridinyl, di- and tetrahydroperimidinyl, di- and tetrahydrophenanthrolinyl (1,7-, 1,8-, 1,10-, 3,8-, and 4,7-), di- and tetrahydrophenazinyl, di- and tetrahydrooxazolopyridinyl, di- and tetrahydroisoxazolopyridinyl, di- and tetrahydropyrrolooxazolyl, and di- and tetrahydropyrrolopyrrolyl. Exemplary 5- or 6-memered heterocyclyl groups include morpholino, pyrrolidinyl, imidazolidinyl, pyrazolidinyl, piperidinyl, piperazinyl, di- and tetrahydrofuranyl, di- and tetrahydrothienyl, di- and tetrahydrooxazolyl, di- and tetrahydroisoxazolyl, di- and tetrahydrooxadiazolyl (1,2,5- and 1,2,3-), dihydropyrrolyl, dihydroimidazolyl, dihydropyrazolyl, di- and tetrahydrotriazolyl (1,2,3- and 1,2,4-), di- and tetrahydrothiazolyl, di- and tetrahydroisothiazolyl, di- and tetrahydrothiadiazolyl (1,2,3- and 1,2,5-), di- and tetrahydropyridyl, di- and tetrahydropyrimidinyl, di- and tetrahydropyrazinyl, di- and tetrahydrotriazinyl (1,2,3-, 1,2,4-, and 1,3,5-), di- and tetrahydropyridazinyl and the like, which may bear one or more substituents. Preferably 2H-1-benzopyranyl (2H-chromenyl), benzodihydropyranyl (chromanyl), 4H-1-benzopyranyl (4H-chromenyl), 1H-2-benzopyranyl (1H-isochromenyl), isochromanyl, 3H-2-benzopyranyl (3H-isochromenyl), 1-benzopyran-4-on-yl (chromonyl), 4-chromanonyl, 1-benzopyran-2-on-yl (coumarinyl), dihydrocoumarinyl, 3-isochromanonyl, 2-coumaranon-yl. In some embodiments, the heterocyclyl group is substituted or unsubstituted 2H-1-benzopyranyl (2H-chromenyl). In some embodiments, the heterocyclyl group is substituted or unsubstituted benzodihydropyranyl (chromanyl). In some embodiments, the heterocyclyl group is substituted or unsubstituted 4H-1-benzopyranyl (4H-chromenyl). In some embodiments, the heterocyclyl group is substituted or unsubstituted 1H-2-benzopyranyl (1H-isochromenyl). In some embodiments, the heterocyclyl group is substituted or unsubstituted isochromanyl. In some embodiments, the heterocyclyl group is substituted or unsubstituted 3H-2-benzopyranyl (3H-isochromenyl). In some embodiments, the heterocyclyl group is substituted or unsubstituted 1-benzopyran-4-on-yl (chromonyl). In some embodiments, the heterocyclyl group is substituted or unsubstituted 4-chromanonyl. In some embodiments, the heterocyclyl group is substituted or unsubstituted 1-benzopyran-2-on-yl (coumarinyl). In some embodiments, the heterocyclyl group is substituted or unsubstituted dihydrocoumarinyl. In some embodiments, the heterocyclyl group is substituted or unsubstituted 3-isochromanonyl. In some embodiments, the heterocyclyl group is substituted or unsubstituted 2-coumaranon-yl. In some embodiments, the heterocyclyl group is a substituted or unsubstituted ($C_3$-$C_{14}$) heterocyclyl group, wherein 1, 2, 3, 4, or 5 carbon atoms are replaced with the same or different heteroatoms of O, N, or S. In some embodiments, the heterocyclyl group is a substituted or unsubstituted ($C_3$-$C_{14}$)heterocyclyl group, wherein 1, 2, 3, 4, or 5 carbon atoms are replaced with O. In some embodiments, the heterocyclyl group is a substituted or unsubstituted ($C_3$-$C_{14}$)heterocyclyl group, wherein 1, 2, 3, 4, or 5 carbon atoms are replaced with N. In some embodiments, the heterocyclyl group is a substituted or unsubstituted ($C_3$-$C_{14}$)heterocyclyl group, wherein 1, 2, 3, 4, or 5 carbon atoms are replaced with S. In some embodiments, the heterocyclyl group is a substituted or unsubstituted ($C_9$-$C_{10}$)heterocyclyl group, wherein 1, 2, 3, 4, or 5 carbon atoms are replaced with the same or different heteroatoms of O, N, or S. In some embodiments, the heterocyclyl group is a substituted or unsubstituted ($C_9$-$C_{10}$) heterocyclyl group, wherein 1, 2, 3, 4, or 5 carbon atoms are replaced with O. In some embodiments, the heterocyclyl group is a substituted or unsubstituted ($C_9$-$C_{10}$)heterocyclyl group, wherein 1, 2, 3, 4, or 5 carbon atoms are replaced with N. In some embodiments, the heterocyclyl group is a substituted or unsubstituted ($C_9$-$C_{10}$)heterocyclyl group, wherein 1, 2, 3, 4, or 5 carbon atoms are replaced with S. In some embodiments, the heterocyclyl group is a substituted or unsubstituted ($C_{10}$)heterocyclyl group, wherein 1, 2, 3, 4, or 5 carbon atoms are replaced with the same or different heteroatoms of O, N, or S. In some embodiments, the heterocyclyl group is a substituted or unsubstituted ($C_{10}$) heterocyclyl group, wherein 1, 2, 3, 4, or 5 carbon atoms are replaced with O. In some embodiments, the heterocyclyl group is a substituted or unsubstituted ($C_{10}$)heterocyclyl group, wherein 1, 2, 3, 4, or 5 carbon atoms are replaced with N. In some embodiments, the heterocyclyl group is a substituted or unsubstituted ($C_{10}$)heterocyclyl group, wherein 1, 2, 3, 4, or 5 carbon atoms are replaced with S.

As used herein and throughout the entire description, the term "heteroalkyl," as used herein, refers to an alkyl moiety, as defined herein, which contain one or more heteroatoms (e.g., oxygen, sulfur, nitrogen, phosphorus, or silicon atoms) in between carbon atoms. The heteroalkyl may be substituted or unsubstituted. In certain embodiments, the heteroalkyl group contains 1-20 carbon atoms and 1-6 heteroatoms ($C_{1-20}$ heteroalkyl). In certain embodiments, the heteroalkyl group contains 1-10 carbon atoms and 1-4 heteroatoms ($C_{1-10}$ heteroalkyl). In certain embodiments, the heteroalkyl group contains 1-6 carbon atoms and 1-3 heteroatoms ($C_{1-6}$ heteroalkyl). In certain embodiments, the heteroalkyl group contains 1-5 carbon atoms and 1-3 heteroatoms ($C_{1-5}$ heteroalkyl). In certain embodiments, the heteroalkyl group contains 1-4 carbon atoms and 1-2 heteroatoms ($C_{1-4}$ heteroalkyl). In certain embodiments, the heteroalkyl group contains 1-3 carbon atoms and 1 heteroatom ($C_{1-3}$ heteroalkyl). In certain embodiments, the heteroalkyl group contains 1-2 carbon atoms and 1 heteroatom ($C_{1-2}$ heteroalkyl). The term "heteroalkylene," as used herein, refers to a biradical derived from an heteroalkyl group, as defined herein, by removal of two hydrogen atoms. Heteroalkylene groups may be cyclic or acyclic, branched or unbranched, substituted or unsubstituted. In certain embodiments the heteroalkyl group is a substituted heteroalkyl group containing 1-6 carbon atoms and 1-3 heteroatoms ($C_{1-6}$ heteroalkyl). In certain embodiments the heteroalkyl group is an unsubstituted heteroalkyl group containing 1-6 carbon atoms and 1-3 heteroatoms ($C_{1-6}$ heteroalkyl). In some embodiments the heteroalkyl is an alkyl moiety wherein on methylene group is replaced by S. In some embodiments the heteroalkyl is an alkyl moiety wherein on methylene group is replaced by O. In some embodiments the heteroalkyl is an alkyl moiety wherein on methylene group is replaced by $NR^1$, wherein is selected from the group consisting of hydrogen, substituted or unsubstituted ($C_1$-$C_6$)alkyl, substituted or unsubstituted ($C_2$-$C_6$)alkenyl, substituted or unsubstituted ($C_2$-$C_6$)alkynyl, substituted or unsubstituted ($C_3$-$C_8$)cycloalkyl, substituted or unsubstituted ($C_6$-$C_{14}$)aryl and substituted or unsubstituted ($C_3$-$C_{14}$)heteroaryl. In some embodiments heteroalkyl is —$CH_2SCH_3$. In some embodiments heteroalkyl is —$CH_2OCH_3$.

As used herein and throughout the entire description, the Heteroalkylene group substituents include, but are not limited to, any of the substituents described herein, that result in the formation of a stable moiety.

As used herein and throughout the entire description, the term "heteroalkenyl," as used herein, refers to an alkenyl moiety, as defined herein, which further contains one or more heteroatoms (e.g., oxygen, sulfur, nitrogen, phosphorus, or silicon atoms) in between carbon atoms. In certain embodiments, the heteroalkenyl group contains 2-20 carbon atoms and 1-6 heteroatoms ($C_{2-20}$ heteroalkenyl). In certain embodiments, the heteroalkenyl group contains 2-10 carbon atoms and 1-4 heteroatoms ($C_{2-10}$ heteroalkenyl). In certain embodiments, the heteroalkenyl group contains 2-6 carbon atoms and 1-3 heteroatoms ($C_{2-6}$ heteroalkenyl). In certain embodiments, the heteroalkenyl group contains 2-5 carbon atoms and 1-3 heteroatoms ($C_{2-5}$ heteroalkenyl). In certain embodiments, the heteroalkenyl group contains 2-4 carbon atoms and 1-2 heteroatoms ($C_{2-4}$ heteroalkenyl). In certain embodiments, the heteroalkenyl group contains 2-3 carbon atoms and 1 heteroatom ($C_{2-3}$ heteroalkenyl). The term "heteroalkenylene," as used herein, refers to a biradical derived from an heteroalkenyl group, as defined herein, by removal of two hydrogen atoms. Heteroalkenylene groups may be cyclic or acyclic, branched or unbranched, substituted or unsubstituted. In certain embodiments the heteroalkenyl group is a substituted heteroalkenyl group containing 1-6 carbon atoms and 1-3 heteroatoms ($C_{1-6}$ heteroalkenyl). In certain embodiments the heteroalkenyl group is an unsubstituted heteroalkenyl group containing 1-6 carbon atoms and 1-3 heteroatoms ($C_{1-6}$ heteroalkenyl).

As used herein and throughout the entire description, the term "heteroalkynyl," as used herein, refers to an alkynyl moiety, as defined herein, which further contains one or more heteroatoms (e.g., oxygen, sulfur, nitrogen, phosphorus, or silicon atoms) in between carbon atoms. In certain embodiments, the heteroalkynyl group contains 2-20 carbon atoms and 1-6 heteroatoms ($C_{2-20}$ heteroalkynyl). In certain embodiments, the heteroalkynyl group contains 2-10 carbon atoms and 1-4 heteroatoms ($C_{2-10}$ heteroalkynyl). In certain embodiments, the heteroalkynyl group contains 2-6 carbon atoms and 1-3 heteroatoms ($C_{2-6}$ heteroalkynyl). In certain embodiments, the heteroalkynyl group contains 2-5 carbon atoms and 1-3 heteroatoms ($C_{2-5}$ heteroalkynyl). In certain embodiments, the heteroalkynyl group contains 2-4 carbon atoms and 1-2 heteroatoms ($C_{2-4}$ heteroalkynyl). In certain embodiments, the heteroalkynyl group contains 2-3 carbon atoms and 1 heteroatom ($C_{2-3}$ heteroalkynyl). The term "heteroalkynylene," as used herein, refers to a biradical derived from an heteroalkynyl group, as defined herein, by removal of two hydrogen atoms. Heteroalkynylene groups may be cyclic or acyclic, branched or unbranched, substituted or unsubstituted. In certain embodiments the heteroalkynyl group is a substituted heteroalkynyl group containing 1-6 carbon atoms and 1-3 heteroatoms ($C_{1-6}$ heteroalkynyl). In certain embodiments the heteroalkynyl group is an unsubstituted heteroalkynyl group containing 1-6 carbon atoms and 1-3 heteroatoms ($C_{1-6}$ heteroalkynyl).

In some embodiments the compound having a structure according to Formula I may be characterized in that, X is O, $NR^1$ or S;

Y is hydrogen or substituted or unsubstituted ($C_1$-$C_6$) alkyl;

Z is selected from the group consisting of substituted or unsubstituted ($C_1$-$C_6$)alkyl, substituted or unsubstituted ($C_2$-$C_6$)alkenyl, substituted or unsubstituted ($C_2$-$C_6$)alkynyl, substituted or unsubstituted ($C_3$-$C_8$)cycloalkyl, substituted or unsubstituted ($C_7$-$C_{14}$)aryl, substituted or unsubstituted ($C_6$-$C_{14}$)aryl($C_1$-$C_6$)alkyl, substituted or unsubstituted ($C_3$-$C_{14}$)heteroaryl, substituted or unsubstituted ($C_3$-$C_{14}$)heteroaryl($C_1$-$C_6$)alkyl, substituted or unsubstituted ($C_3$-$C_{14}$)heterocyclyl, substituted or unsubstituted ($C_1$-$C_6$)heteroalkyl, substituted or unsubstituted ($C_2$-$C_6$)heteroalkenyl and substituted or unsubstituted ($C_2$-$C_6$)heteroalkynyl;

$R^1$ is hydrogen or substituted or unsubstituted ($C_1$-$C_6$) alkyl, with the proviso that Z is not a substituted or unsubstituted monocyclic six-membered aryl.

In some embodiments the compound having a structure according to Formula I may be characterized in that, X is O, $NR^1$ or S;

Y is hydrogen or substituted or unsubstituted ($C_1$-$C_6$) alkyl;

Z is selected from the group consisting of substituted or unsubstituted ($C_1$-$C_6$)alkyl, substituted or unsubstituted ($C_3$-$C_{14}$)heteroaryl, substituted or unsubstituted ($C_3$-$C_{14}$)Heterocyclyl and substituted or unsubstituted ($C_1$-$C_6$)heteroalkyl;

$R^1$ is hydrogen or substituted or unsubstituted ($C_1$-$C_6$) alkyl, preferably with the proviso that Z is not a substituted or unsubstituted monocyclic six-membered aryl.

In some embodiments the compound having a structure according to Formula I may be characterized in that, X is O;

Y is hydrogen or substituted or unsubstituted ($C_1$-$C_6$) alkyl;

Z is selected from the group consisting of substituted or unsubstituted ($C_1$-$C_6$)alkyl, substituted or unsubstituted ($C_3$-$C_{14}$)heteroaryl, substituted or unsubstituted ($C_3$-$C_{14}$)heterocyclyl and substituted or unsubstituted ($C_1$-$C_6$)heteroalkyl; and preferably with the proviso that Z is not a substituted or unsubstituted monocyclic six-membered aryl.

In some embodiments the compound having a structure according to Formula I may be characterized in that, X is O, $NR^1$ or S;

Y is hydrogen or substituted or unsubstituted ($C_1$-$C_6$) alkyl;

Z is selected from the group consisting of substituted or unsubstituted ($C_3$-$C_{14}$)heteroaryl and substituted or unsubstituted ($C_3$-$C_{14}$)heterocyclyl;

$R^1$ is hydrogen or substituted or unsubstituted ($C_1$-$C_6$) alkyl; and preferably with the proviso that Z is not a substituted or unsubstituted monocyclic six-membered aryl.

In some embodiments the compound having a structure according to Formula I may be characterized in that, X is O;

Y is hydrogen or substituted or unsubstituted ($C_1$-$C_6$) alkyl;

Z is selected from the group consisting of substituted or unsubstituted ($C_3$-$C_{14}$)heteroaryl and substituted or unsubstituted ($C_3$-$C_{14}$)heterocyclyl; and preferably with the proviso that Z is not a substituted or unsubstituted monocyclic six-membered aryl.

In some embodiments the compound having a structure according to Formula I may be characterized in that, X is O, $NR^1$ or S;

Y is hydrogen or substituted or unsubstituted ($C_1$-$C_6$) alkyl;

Z is selected from the group consisting of substituted or unsubstituted 2H-1-benzopyranyl (2H-chromenyl), substituted or unsubstituted benzodihydropyranyl (chromanyl), substituted or unsubstituted 4H-1-benzopyranyl (4H-chromenyl), substituted or unsubstituted 1H-2-benzopyranyl (1H-isochromenyl), substituted or unsubstituted isochromanyl, substituted or unsubstituted 3H-2-benzopyranyl (3H-isochromenyl), substituted or unsubstituted 1-benzopyran-4-on-yl (chromonyl), substituted or unsubstituted 4-chromanonyl, substituted or unsubstituted 1-benzopyran-2-on-yl (coumarinyl), substituted or unsubstituted dihydrocoumarinyl, substituted or unsubstituted 3-isochromanonyl, substituted or unsubstituted 2-coumaranonyl, substituted or unsubstituted ($C_1$-$C_6$)alkyl, substituted or unsubstituted ($C_1$-$C_6$)heteroalkyl, substituted or unsubstituted imidazolyl, substituted or unsubstituted azaindolyl including 7-azaindolyl, 6-azaindolyl, 5-azaindolyl and 4-azaindolyl, substituted or unsubstituted diazaindolyl and substituted or unsubstituted indolyl;

$R^1$ is hydrogen or substituted or unsubstituted ($C_1$-$C_6$) alkyl, and preferably with the proviso that Z is not a substituted or unsubstituted monocyclic six-membered aryl.

In some embodiments the compound having a structure according to Formula I may be characterized in that, X is O;

Y is hydrogen or substituted or unsubstituted ($C_1$-$C_6$) alkyl;

Z is selected from the group consisting of substituted or unsubstituted 2H-1-benzopyranyl (2H-chromenyl), substituted or unsubstituted benzodihydropyranyl (chromanyl), substituted or unsubstituted 4H-1-benzopyranyl (4H-chromenyl), substituted or unsubstituted 1H-2-benzopyranyl (1H-isochromenyl), substituted or unsubstituted isochromanyl, substituted or unsubstituted 3H-2-benzopyranyl (3H-isochromenyl), substituted or unsubstituted 1-benzopyran-4-on-yl (chromonyl), substituted or unsubstituted 4-chromanonyl, substituted or unsubstituted 1-benzopyran-2-on-yl (coumarinyl), substituted or unsubstituted dihydrocoumarinyl, substituted or unsubstituted 3-isochromanonyl, substituted or unsubstituted 2-coumaranonyl, substituted or unsubstituted ($C_1$-$C_6$)alkyl, substituted or unsubstituted ($C_1$-$C_6$)heteroalkyl, substituted or unsubstituted imidazolyl, substituted or unsubstituted azaindolyl including 7-azaindolyl, 6-azaindolyl, 5-azaindolyl and 4-azaindolyl, substituted or unsubstituted diazaindolyl and substituted or unsubstituted indolyl; and preferably with the proviso that Z is not a substituted or unsubstituted monocyclic six-membered aryl.

In some embodiments the compound having a structure according to Formula I may be characterized in that, X is O, $NR^1$ or S;

Y is hydrogen or substituted or unsubstituted $(C_1-C_6)$ alkyl;

Z is selected from the group consisting of substituted or unsubstituted 1-benzopyran-2-on-yl (coumarinyl), substituted or unsubstituted dihydrocoumarinyl, substituted or unsubstituted imidazolyl, substituted or unsubstituted azaindolyl including 7-azaindolyl, 6-azaindolyl, 5-azaindolyl and 4-azaindolyl, and substituted or unsubstituted indolyl;

$R^1$ is hydrogen or substituted or unsubstituted $(C_1-C_6)$ alkyl, and preferably with the proviso that Z is not a substituted or unsubstituted monocyclic six-membered aryl.

In some embodiments the compound having a structure according to Formula I may be characterized in that, X is O;

Y is hydrogen or substituted or unsubstituted $(C_1-C_6)$ alkyl;

Z is selected from the group consisting of substituted or unsubstituted 1-benzopyran-2-on-yl (coumarinyl), substituted or unsubstituted dihydrocoumarinyl, substituted or unsubstituted imidazolyl, substituted or unsubstituted azaindolyl including 7-azaindolyl, 6-azaindolyl, 5-azaindolyl and 4-azaindolyl, and substituted or unsubstituted indolyl; and preferably with the proviso that Z is not a substituted or unsubstituted monocyclic six-membered aryl.

In some embodiments X is O. In some embodiments X is S. In some embodiments X is $NR^1$, wherein $R^1$ is selected from the group consisting of hydrogen, substituted or unsubstituted $(C_1-C_6)$alkyl, substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_6-C_{14})$aryl and substituted or unsubstituted $(C_3-C_{14})$heteroaryl, preferably hydrogen or substituted or unsubstituted $(C_1-C_6)$alkyl, more preferably hydrogen, more preferably substituted or unsubstituted $(C_1-C_6)$alkyl, even more preferably unsubstituted $(C_1-C_6)$alkyl.

In some embodiments Y is selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl. In some embodiments Y is selected from the group consisting of hydrogen, substituted or unsubstituted alkyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted Heterocyclyl and substituted or unsubstituted heteroalkyl. In some embodiments Y is selected from the group consisting of substituted or unsubstituted $(C_1-C_6)$alkyl, substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_6-C_{14})$aryl, substituted or unsubstituted $(C_6-C_{14})$aryl$(C_1-C_6)$alkyl, substituted or unsubstituted $(C_3-C_{14})$heteroaryl, substituted or unsubstituted $(C_3-C_{14})$heteroaryl$(C_1-C_6)$alkyl, substituted or unsubstituted $(C_3-C_{14})$heterocyclyl, substituted or unsubstituted $(C_1-C_6)$heteroalkyl, substituted or unsubstituted $(C_2-C_6)$heteroalkenyl and substituted or unsubstituted $(C_2-C_6)$heteroalkynyl. In some embodiments Y is hydrogen or substituted or unsubstituted $(C_1-C_6)$alkyl. In some embodiments Y is hydrogen. In some embodiments Y is substituted or unsubstituted alkyl, preferably substituted or unsubstituted $(C_1-C_6)$alkyl. In some embodiments Y is substituted or unsubstituted alkenyl, preferably substituted or unsubstituted $(C_2-C_6)$alkenyl. In some embodiments Y is substituted or unsubstituted alkynyl, preferably substituted or unsubstituted $(C_2-C_6)$alkynyl. In some embodiments Y is substituted or unsubstituted cycloalkyl, preferably substituted or unsubstituted $(C_3-C_8)$cycloalkyl. In some embodiments Y is substituted or unsubstituted aryl, preferably substituted or unsubstituted $(C_6-C_{14})$aryl. In some embodiments Y is substituted or unsubstituted Arylalkyl, preferably substituted or unsubstituted $(C_6-C_{14})$aryl$(C_1-C_6)$alkyl. In some embodiments Y is substituted or unsubstituted heteroaryl, preferably substituted or unsubstituted $(C_3-C_{14})$heteroaryl. In some embodiments Y is substituted or unsubstituted heteroarylalkyl, preferably substituted or unsubstituted $(C_3-C_{14})$heteroaryl$(C_1-C_6)$alkyl. In some embodiments Y is substituted or unsubstituted heterocyclyl, preferably substituted or unsubstituted $(C_3-C_{14})$heterocyclyl. In some embodiments Y is substituted or unsubstituted heteroalkyl, preferably substituted or unsubstituted $(C_1-C_6)$heteroalkyl. In some embodiments Y is substituted or unsubstituted heteroalkenyl, preferably substituted or unsubstituted $(C_2-C_6)$heteroalkenyl. In some embodiments Y is substituted or unsubstituted heteroalkynyl, preferably substituted or unsubstituted $(C_2-C_6)$heteroalkynyl.

In some embodiments Z is selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl; and with the proviso that Z is not a substituted or unsubstituted monocyclic six-membered aryl. In some embodiments Z is selected from the group consisting of hydrogen, substituted or unsubstituted alkyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted Heterocyclyl and substituted or unsubstituted heteroalkyl; and with the proviso that Z is not a substituted or unsubstituted monocyclic six-membered aryl. In some embodiments Z is selected from the group consisting of substituted or unsubstituted $(C_1-C_6)$alkyl, substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_7-C_{14})$aryl, substituted or unsubstituted $(C_6-C_{14})$aryl$(C_1-C_6)$alkyl, substituted or unsubstituted $(C_3-C_{14})$heteroaryl, substituted or unsubstituted $(C_3-C_{14})$heteroaryl$(C_1-C_6)$alkyl, substituted or unsubstituted $(C_3-C_{14})$heterocyclyl, substituted or unsubstituted $(C_1-C_6)$heteroalkyl, substituted or unsubstituted $(C_2-C_6)$heteroalkenyl and substituted or unsubstituted $(C_2-C_6)$heteroalkynyl; and with the proviso that Z is not a substituted or unsubstituted monocyclic six-membered aryl. In some embodiments Z is hydrogen or substituted or unsubstituted $(C_1-C_6)$alkyl. In some embodiments Z is hydrogen. In some embodiments Z is substituted or unsubstituted alkyl, preferably substituted or unsubstituted ($C_1$-$C_6$)alkyl. In some embodiments Z is substituted or unsubstituted alkenyl, preferably substituted or unsubstituted ($C_2$-$C_6$)alkenyl. In some embodiments Z is substituted or unsubstituted alkynyl, preferably substituted or unsubstituted ($C_2$-$C_6$)alkynyl. In some embodiments Z is substituted or unsubstituted cycloalkyl, preferably substituted or unsubstituted ($C_3$-$C_8$)cycloalkyl. In some embodiments Z is substituted or unsubstituted aryl, preferably substituted or unsubstituted ($C_7$-$C_{14}$)aryl preferably with the proviso that Z is not a substituted or unsubstituted monocyclic six-membered aryl. In some embodiments Z is substituted or unsubstituted Arylalkyl, preferably substituted or unsubstituted ($C_6$-$C_{14}$)aryl($C_1$-$C_6$)alkyl, preferably with the proviso that Z is not a substituted or unsubstituted monocyclic six-membered aryl. In some embodiments Z is substituted or unsubstituted heteroaryl, preferably substituted or unsubstituted ($C_3$-$C_{14}$)heteroaryl. In some embodiments Z is substituted or unsubstituted heteroarylalkyl, preferably substituted or unsubstituted ($C_3$-$C_{14}$)heteroaryl($C_1$-$C_6$)alkyl. In some embodiments Z is substituted or unsubstituted Heterocyclyl, preferably substituted or unsubstituted ($C_3$-$C_{14}$)heterocyclyl. In some embodiments Z is substituted or unsubstituted heteroalkyl, preferably substituted or unsubstituted ($C_1$-$C_6$)heteroalkyl. In some embodiments Z is substituted or unsubstituted heteroalkenyl, preferably substituted or unsubstituted ($C_2$-$C_6$)heteroalkenyl. In some embodiments Z is substituted or unsubstituted heteroalkynyl, preferably substituted or unsubstituted ($C_2$-$C_6$)heteroalkynyl. In some embodiments Z is selected from the group consisting of substituted or unsubstituted 2H-1-benzopyranyl (2H-chromenyl), substituted or unsubstituted benzodihydropyranyl (chromanyl), substituted or unsubstituted 4H-1-benzopyranyl (4H-chromenyl), substituted or unsubstituted 1H-2-benzopyranyl (1H-isochromenyl), substituted or unsubstituted isochromanyl, substituted or unsubstituted 3H-2-benzopyranyl (3H-isochromenyl), substituted or unsubstituted 1-benzopyran-4-on-yl (chromonyl), substituted or unsubstituted 4-chromanonyl, substituted or unsubstituted 1-benzopyran-2-on-yl (coumarinyl), substituted or unsubstituted dihydrocoumarinyl, substituted or unsubstituted 3-isochromanonyl, substituted or unsubstituted 2-coumaranon-yl, substituted or unsubstituted ($C_1$-$C_6$)alkyl, substituted or unsubstituted ($C_1$-$C_6$)heteroalkyl, substituted or unsubstituted imidazolyl, substituted or unsubstituted azaindolyl including 7-azaindolyl, 6-azaindolyl, 5-azaindolyl and 4-azaindolyl and substituted or unsubstituted indolyl. In some embodiments Z is substituted or unsubstituted 2H-1-benzopyranyl (2H-chromenyl). In some embodiments Z is substituted or unsubstituted benzodihydropyranyl (chromanyl). In some embodiments Z is substituted or unsubstituted 4H-1-benzopyranyl (4H-chromenyl). In some embodiments Z is substituted or unsubstituted 1H-2-benzopyranyl (1H-isochromenyl). In some embodiments Z is substituted or unsubstituted isochromanyl. In some embodiments Z is substituted or unsubstituted 3H-2-benzopyranyl (3H-isochromenyl). In some embodiments Z is substituted or unsubstituted 1-benzopyran-4-on-yl (chromonyl). In some embodiments Z is substituted or unsubstituted 4-chromanonyl. In some embodiments Z is substituted or unsubstituted 1-benzopyran-2-on-yl (coumarinyl). In some embodiments Z is substituted or unsubstituted dihydrocoumarinyl. In some embodiments Z is substituted or unsubstituted 3-isochromanonyl. In some embodiments Z is substituted or unsubstituted 2-coumaranon-yl. In some embodiments Z is substituted or unsubstituted ($C_1$-$C_6$)alkyl. In some embodiments Z is substituted or unsubstituted ($C_1$-$C_6$)heteroalkyl. In some embodiments Z is substituted or unsubstituted imidazolyl. In some embodiments Z is substituted or unsubstituted azaindolyl including 7-azaindolyl, 6-azaindolyl, 5-azaindolyl and 4-azaindolyl. In some embodiments Z is substituted or unsubstituted indolyl. In some embodiments Z is not a substituted monocyclic six-membered aryl or unsubstituted monocyclic six-membered aryl. In some embodiments Z is not a substituted phenyl or unsubstituted phenyl. In some embodiments Z is not a phenyl substituted with 1, 2, 3, 4 or 5 substituents selected from the group consisting of —$NO_2$, —$N_3$, halogen, —$NH_2$, hydroxyl, —$OR^{11}$ and —$C(=O)R^{11}$, wherein $R^{11}$ is hydrogen, substituted alkyl or substituted alkynyl.

As an alternative, the present in invention also provides a method method for the production of a functionalized polypeptide comprising (a") introducing or adding at the C-terminus of a polypeptide a recognition sequence for tubulin tyrosine ligase;

(b") contacting the polypeptide obtained in step (a) in the presence of tubulin tyrosine ligase and a compound under conditions suitable for the tubulin tyrosine ligase to functionalize said polypeptide with said compound having a structure according to Formula I

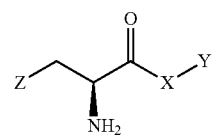

(I)

wherein

X is O, $NR^1$ or S;

Y is selected from the group consisting of a substituted or unsubstituted aliphatic group, a substituted or unsubstituted heteroaliphatic group, substituted or unsubstituted aryl, substituted or unsubstituted arylalkyl, substituted or unsubstituted heteroaryl, substituted or unsubstituted heteroarylalkyl, substituted or unsubstituted heterocyclyl, a click chemistry handle, biotin, a carrier, a polypeptide, a detectable label, a chemical compound, a nucleic acid, a carbohydrate, or a lipid;

Z is selected from the group consisting of a substituted or unsubstituted aliphatic group, a substituted or unsubstituted heteroaliphatic group, substituted or unsubstituted aryl, substituted or unsubstituted arylalkyl, substituted or unsubstituted heteroaryl, substituted or unsubstituted heteroarylalkyl, a substituted or unsubstituted heterocyclyl, a click chemistry handle, biotin, a carrier, a polypeptide, a detectable label, a chemical compound, a nucleic acid, a carbohydrate, or a lipid; and $R^1$ is selected from the group consisting of hydrogen, substituted or unsubstituted ($C_1$-$C_6$)alkyl, substituted or unsubstituted ($C_2$-$C_6$)alkenyl, substituted or unsubstituted ($C_2$-$C_6$)alkynyl, substituted or unsubstituted ($C_3$-$C_8$)cycloalkyl, substituted or unsubstituted ($C_6$-$C_{14}$)aryl and substituted or unsubstituted ($C_3$-$C_{14}$)heteroaryl; with the proviso that Z is not a substituted or unsubstituted monocyclic six-membered aryl.

Said alternative method allows, so to say, a one-step functionalization of a polypeptide in that tubulin tyrosine ligase functionalizes a polypeptide into which a recognition sequence for tubulin tyrosine ligase is introduced or added at its C-terminus with a compound having a structure according to Formula I conjugated to a chemical entity. Thus, said method, so to say, simplifies the functionalization in that no extra functionalization step is required, where tubulin tyrosine ligase first adds a compound having a structure according to Formula I to the C-terminus of a polypeptide into which a recognition sequence for tubulin tyrosine ligase is introduced or added in order to then conjugate a moiety to said functionalized polypeptide. Rather, tubulin tyrosine ligase was found by the present inventors to functionalize a polypeptide into which a recognition sequence for tubulin tyrosine ligase is introduced or added at its C-terminus with a compound having a structure according to Formula I already conjugated to a moiety.

As used herein and throughout the entire description, the term "aliphatic" includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms ($C_{1-20}$ aliphatic). In certain embodiments, the aliphatic group has 1-10 carbon atoms ($C_{1-10}$ aliphatic). In certain embodiments, the aliphatic group has 1-6 carbon atoms ($C_{1-6}$ aliphatic). In certain embodiments, the aliphatic group has 1-5 carbon atoms ($C_{1-5}$ aliphatic). In certain embodiments, the aliphatic group has 1-4 carbon atoms ($C_{1-4}$ aliphatic). In certain embodiments, the aliphatic group has 1-3 carbon atoms ($C_{1-3}$ aliphatic). In certain embodiments, the aliphatic group has 1-2 carbon atoms ($C_{1-2}$ aliphatic). Aliphatic group substituents include, but are not limited to, any of the substituents described herein, that result in the formation of a stable moiety. In some embodiments, the aliphatic group is saturated or unsaturated, unbranched or branched alkyl, preferably ($C_1$-$C_{20}$)alkyl, more preferably ($C_1$-$C_{10}$)alkyl, even more preferably ($C_1$-$C_6$)alkyl.

As used herein and throughout the entire description, the term "heteroaliphatic" refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that further contains one or more heteroatoms (e.g., oxygen, sulfur, nitrogen, phosphorus, or silicon atoms) between carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl," "heteroalkynyl," and the like. Furthermore, as used herein, the terms "heteroalkyl," "heteroalkenyl," "heteroalkynyl," and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms and 1-6 heteroatoms ($C_{1-20}$ heteroaliphatic). In certain embodiments, the heteroaliphatic group contains 1-10 carbon atoms and 1-4 heteroatoms ($C_{1-10}$ heteroaliphatic). In certain embodiments, the heteroaliphatic group contains 1-6 carbon atoms and 1-3 heteroatoms ($C_{1-6}$ heteroaliphatic). In certain embodiments, the heteroaliphatic group contains 1-5 carbon atoms and 1-3 heteroatoms ($C_{1-5}$ heteroaliphatic). In certain embodiments, the heteroaliphatic group contains 1-4 carbon atoms and 1-2 heteroatoms ($C_{1-4}$ heteroaliphatic). In certain embodiments, the heteroaliphatic group contains 1-3 carbon atoms and 1 heteroatom ($C_{1-3}$ heteroaliphatic). In certain embodiments, the heteroaliphatic group contains 1-2 carbon atoms and 1 heteroatom ($C_{1-2}$ heteroaliphatic). Heteroaliphatic group substituents include, but are not limited to, any of the substituents described herein, that result in the formation of a stable moiety. In some embodiments, the aliphatic group is saturated or unsaturated, unbranched or branched alkyl, preferably ($C_1$-$C_{20}$)heteroalkyl, more preferably ($C_1$-$C_{10}$)heteroalkyl, even more preferably ($C_1$-$C_6$) heteroalkyl.

As used herein and throughout the entire description, the term "click chemistry" refers to a chemical philosophy introduced by Kolb, Finn and Sharpless in 2001 and encompasses a group of powerful linking reactions that are able to generate covalent bonds quickly and reliably by joining small units comprising reactive groups together. Click chemistry reactions are typically modular, wide in scope, give high chemical yields, generate inoffensive byproducts, are stereospecific, exhibit a large thermodynamic driving force >84 kJ/mol to favor a reaction with a single reaction product, and/or can be carried using readily available starting materials and reagents out under simple, physiological reaction conditions. In addition, click chemistry reactions preferably use no toxic solvents or use a solvent that is benign or easily removed (preferably water), and/or provides simple product isolation by non-chromatographic methods (crystallisation or distillation). A distinct exothermic reaction makes a reactant "spring loaded".

As used herein and throughout the entire description, the term "click chemistry handle," as used herein, refers to a reactant, or a reactive group, that can partake in a click chemistry reaction. Such a reactant or reactive group is preferably an unnatural (non-natural) functional group for a chemoselective or bioorthogonal modification; however, it may alternatively be a natural functional group for a chemoselective or bioorthogonal modification. For example, a strained alkyne, e.g., a cyclooctyne, is a click chemistry handle, since it can partake in a strain-promoted cycloaddition, e.g. strain-promoted azide-alkyne cycloaddition (SPAAC). In general, click chemistry reactions require at least two molecules comprising click chemistry handles that can react with each other. Such click chemistry handle pairs that are reactive with each other are sometimes referred to herein as "partner click chemistry handles". For example, an azide is a partner click chemistry handle to a cyclooctyne or any other alkyne. In the context of the present invention, the click chemistry handle can preferably be selected from the group consisting of terminal alkyne, azide, strained alkyne, diene, dieneophile, alkoxyamine, carbonyl, phosphine, hydrazide, thiol, tetrazine, alkene, and cyclooctyne. Other suitable click chemistry handles are readily accessible to the person skilled in the art.

Click chemistry reactions comprise, e.g., cycloaddition reactions, especially from the 1,3-dipolar family, hetero-Diels-Alder reactions; nucleophilic ring-opening reactions, e.g. of strained heterocyclic electrophiles, such as epoxides, aziridines, cyclic sulfates, cyclic sulfamidates, aziridinium ions and episulfonium ions; carbonyl chemistry of the non-aldol type (e.g. the formation of oxime ethers, hydrazones and aromatic heterocycles); and addition to carbon-carbon multiple bonds; e.g. oxidation reactions, such as epoxidation, dihydroxylation, aziridination, and nitrosyl and sulfenyl halide additions but also certain Michael addition reactions. General principles of click chemistry reactions have been described by Kolb, Finn and Sharpless (2001). It is within the knowledge of the person skilled in the art to select a click chemistry reaction that is suitable for attaching a desired moiety to the compound having a structure according to Formula I covalently bonded to the polypeptide of the invention.

In the context of conjugation via click chemistry, the conjugation is via a covalent bond formed by the reaction of the click chemistry handles. In certain embodiments, the association is covalent, and the entities are said to be "conjugated" to one another. In some embodiments, a protein is post-translationally conjugated to another molecule, for example, a second protein, by forming a covalent bond between the protein and the other molecule after the protein has been translated, and, in some embodiments, after the protein has been isolated. In some embodiments, the post-translational conjugation of the protein and the second molecule, for example, the second protein, is effected via installing a click chemistry handle on the protein, and a second click chemistry handle, which can react to the first click chemistry handle, on the second molecule, and carrying out a click chemistry reaction in which the click chemistry handles react and form a covalent bond between the protein and the second molecule, thus generating a chimeric protein. In some embodiments, two proteins are conjugated at their respective C-termini, generating a C—C conjugated chimeric protein. In some embodiments, two proteins are conjugated at their respective N-termini, generating an N—N conjugated chimeric protein.

As used herein and throughout the entire description, the term "carrier" when used herein refers to a moiety, such as, e.g., a molecule or polymer, which acts to improve delivery, effectiveness and/or stability of the polypeptide of the invention. For example, if the polypeptide of the invention is envisaged for treatment of a subject as described herein, the carrier may be a pharmaceutically acceptable carrier that can direct the polypeptide of the invention to a specific location, facilitate its transport, enhance its serum stability, bioavailability, and the like. Pharmaceutically acceptable carriers are described herein. A carrier may, however, also be a bead, such as a magnetic bead, or a solid surface. A solid surface may be selected from polystyrene, polypropylene, polyvinylchloride, polyacrylamide, celluloses, dextrans, synthetic polymers and co-polymers, latex, silica, agarose, metal, glass, or carbon.

The polypeptide moiety may be an antibody or fragment thereof. As is well known in the art, an antibody is an immunoglobulin molecule capable of specific binding to a target, such as a carbohydrate, polynucleotide, lipid, polypeptide, etc., through at least one epitope recognition site, located in the variable region of the immunoglobulin molecule. As used herein and throughout the entire description, the term encompasses monoclonal antibodies, chimeric antibodies, humanized antibodies, human antibodies, scFv, DART, domain antibodies, nanobodies, adnectin, affibodies, anticalins, DARPins, aptamers or functional equivalents thereof of any one of the aforementioned antibody species as well as affinity binders.

As used herein and throughout the entire description, a "detectable label" is a molecule or material that can produce a detectable (such as visually, electronically or otherwise) signal that indicates the presence and/or concentration of the label in a sample. Thereby, e.g., the presence, location and/or concentration of the polypeptide in a sample can be detected by detecting the signal produced by the detectable label. A detectable label can be detected directly or indirectly. It will be appreciated that the label may be attached to or incorporated into a molecule, for example, a protein, polypeptide, or other entity, at any position. It will be appreciated that, in certain embodiments, a label may react with a suitable substrate (e.g., a luciferin) to generate a detectable signal. In particular, the detectable label can be a fluorophore, an enzyme (peroxidase, luciferase), a radioisotope, a fluorescent protein, or a fluorescent dye. Other dectectable lables include chemiluminescent labels, electrochemiluminescent labels, bioluminescent labels, polymers, polymer particles, metal particles, haptens, and dyes.

As used herein and throughout the entire description, a "fluorophore" (or fluorochrome) is a fluorescent chemical compound that can re-emit light upon light excitation. Examples of fluorophores include 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeton Red, inorganic fluorescent labels such as particles based on semiconductor material like coated CdSe nanocrystallites.

As used herein and throughout the entire description, examples for fluorescent proteins include Exemplary fluorescent proteins include, e.g., Sirius, Azurite, EBFP, EBFP2, TagBFP, mTurquoise, ECFP, Cerulean, CyPet, TagCFP, mTFPI, mUkGl, mAGI, AcGFPI, TagGFP2, EGFP, GFP, mWasabi, EmGFP, YFP, TagYPF, Ypet, EYFP, Topaz, SYFP2, Venus, Citrine, mKO, mK02, mOrange, mOrange2, TagRFP, TagRFP-T, mStrawberry, mRuby, mCherry, mRaspberry, mKate2, mPlum, mNeptune, mKalama2, T-Sapphire, mAmetrine, mKeima, UnaG, dsRed, eqFP611, Dronpa, KFP, EosFP, Dendra, and IrisFP.

As used herein and throughout the entire description, examples of enzymes used as enzymatic labels include horseradish peroxidase (HRP), alkaline phosphatase (ALP or AP), β-galactosidase (GAL), glucose-6-phosphate dehydrogenase, β-N-acetylglucosamimidase, β-glucuronidase, invertase, Xanthine Oxidase, firefly luciferase and glucose oxidase (GO).

As used herein and throughout the entire description, examples of radioactive labels include radioactive isotopes of hydrogen, iodide, cobalt, selenium, tritium, carbon, sulfur and phosphorous. $^{2}H$, $^{3}H$, $^{13}C$, $^{14}C$, $^{15}N$, $^{18}F$, $^{31}P$, $^{32}P$, $^{35}S$, $^{67}Ga$, $^{76}Br$, $^{99m}Tc$, (Tc-99m), $^{m}In$, $^{123}I$, $^{125}I$, $^{131}I$, $^{153}Gd$, $^{169}Yb$, and $^{186}Re$.

As used herein and throughout the entire description, a "chemical compound" can in general be any chemical compound that can be covalently linked to the compound having a structure according to Formula I attached to the polypeptide of the invention. In particular, the chemical compound can be a small molecule, a polymer, such as a synthetic polymer (PEG) or a therapeutic agent, such as a cytotoxic agent. As such, for example an antibody can be equipped by the means and methods of the present invention with a cytotoxic drug to become an antibody-drug conjugate (ADC). Of course, it is envisaged that a linker is conjugated to a compound having a structure according to Formula I and a cytotoxic drug, if necessary. However, the cytotoxic drug may also be conjugated to the compound having a structure according to Formula I without a linker. Examples of cytotoxic drugs are doxorubicin or derivatives thereof, maytanosinoids, e.g. DM1 or DM4, auristatins, e.g. auristatin E or auristatin F, calicheamicins, CC-1065, duocarmycins, anthracyclines, pyrrolobentodiazepins, centanamycin, iriontecan metabolite (SN38).

As used herein and throughout the entire description, exemplary small molecules include hormones, nucleotides, amino acids, sugars, lipids and organic compounds having a molecular weight of less than 100 kD. In some embodiments, small molecules that are approved by the FDA can be preferred.

As used herein and throughout the entire description, exemplary polymers include peptides, oligonucleotides, and polymeric organic compounds. In particular, suitable polymers include, e.g., elastin-like polypeptides (ELP), polypeptide chains of varying length (e.g., XTEN® technology or PASylation®), and carbohydrates, such as hydroxyethyl starch (e.g., HESylation®), polysialic acid (e.g., PolyXen® technology) or polyethylene glycol (PEGylation®).

As used herein and throughout the entire description, the term "nucleic acid" refers to a polymer of nucleotides linked together by phosphodiester bonds. The term in general includes any polynucleotide in any possible configuration, such as single stranded, double stranded, linear, circular or a combination thereof. Nucleic acids include, e.g., DNA molecules, RNA molecules, analogues of the DNA or RNA generated using nucleotide analogues, and aptamers. An aptamer is typically a nucleic acid molecule that is able to bind molecules such as peptides, proteins and low molecular weight compounds.

In some embodiments the compound having a structure according to Formula I may be characterized in that,
X is O;
Y is selected from the group consisting of a substituted or unsubstituted aliphatic group, a substituted or unsubstituted heteroaliphatic group, substituted or unsubstituted aryl, substituted or unsubstituted arylalkyl, substituted or unsubstituted heteroaryl, substituted or unsubstituted heteroarylalkyl, substituted or unsubstituted heterocyclyl, a click chemistry handle, biotin, a carrier, a polypeptide, a detectable label, a chemical compound, a nucleic acid, a carbohydrate, or a lipid;
Z is selected from the group consisting of a substituted or unsubstituted aliphatic group, a substituted or unsubstituted heteroaliphatic group, substituted or unsubstituted aryl, substituted or unsubstituted arylalkyl, substituted or unsubstituted heteroaryl, substituted or unsubstituted heteroarylalkyl, substituted or unsubstituted heterocyclyl, a click chemistry handle, biotin, a carrier, a polypeptide, a detectable label, a chemical compound, a nucleic acid, a carbohydrate, or a lipid; and
with the proviso that Z is not a substituted or unsubstituted monocyclic six-membered aryl.

In some embodiments the compound having a structure according to Formula I may be characterized in that,
X is $NR^1$;
Y is selected from the group consisting of a substituted or unsubstituted aliphatic group, a substituted or unsubstituted heteroaliphatic group, substituted or unsubstituted aryl, substituted or unsubstituted arylalkyl, substituted or unsubstituted heteroaryl, substituted or unsubstituted heteroarylalkyl, substituted or unsubstituted heterocyclyl, a click chemistry handle, biotin, a carrier, a polypeptide, a detectable label, a chemical compound, a nucleic acid, a carbohydrate, or a lipid;
Z is selected from the group consisting of a substituted or unsubstituted aliphatic group, a substituted or unsubstituted heteroaliphatic group, substituted or unsubstituted aryl, substituted or unsubstituted arylalkyl, substituted or unsubstituted heteroaryl, substituted or unsubstituted heteroarylalkyl, substituted or unsubstituted heterocyclyl, a click chemistry handle, biotin, a carrier, a polypeptide, a detectable label, a chemical compound, a nucleic acid, a carbohydrate, or a lipid;
$R^1$ is hydrogen or substituted or unsubstituted $(C_1-C_6)$alkyl, substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_6-C_{14})$aryl and substituted or unsubstituted $(C_3-C_{14})$heteroaryl; and
with the proviso that Z is not a substituted or unsubstituted monocyclic six-membered aryl.

In some embodiments Y is selected from the group consisting of substituted or unsubstituted aliphatic group, a substituted or unsubstituted heteroaliphatic group, a click chemistry handle, biotin, a carrier, a polypeptide, a detectable label, a chemical compound, a nucleic acid, a carbohydrate, or a lipid. In some embodiments Y is selected from the group consisting of substituted or unsubstituted aliphatic group, a substituted or unsubstituted heteroaliphatic group, a click chemistry handle, biotin, a carrier, a polypeptide, a detectable label, a chemical compound or a nucleic acid. In some embodiments Y is a substituted or unsubstituted aliphatic group. In some embodiments Y is a substituted or unsubstituted heteroaliphatic group. In some embodiments Y is a substituted or unsubstituted aryl, preferably substituted or unsubstituted $(C_6-C_{14})$aryl. In some embodiments Y is a substituted or unsubstituted arylalkyl, preferably substituted or unsubstituted $(C_6-C_{14})$aryl$(C_1-C_6)$alkyl. In some embodiments Y is a substituted or unsubstituted heteroaryl, preferably substituted or unsubstituted $(C_3-C_{14})$heteroaryl. In some embodiments Y is a substituted or unsubstituted heteroarylalkyl, preferably substituted or unsubstituted $(C_3-C_{14})$heteroaryl$(C_1-C_6)$alkyl. In some embodiments Y is a substituted or unsubstituted heterocyclyl. In some embodiments Y is a click chemistry handle. In some embodiments Y is a biotin. In some embodiments Y is a carrier. In some embodiments Y is a polypeptide. In some embodiments Y is a detectable label. In some embodiments Y is a chemical compound. In some embodiments Y is a nucleic acid. In some embodiments Y is a carbohydrate. In some embodiments Y is a lipid.

In some embodiments Z is selected from the group consisting of substituted or unsubstituted aliphatic group, a substituted or unsubstituted heteroaliphatic group, a click chemistry handle, biotin, a carrier, a polypeptide, a detectable label, a chemical compound, a nucleic acid, a carbohydrate, or a lipid. In some embodiments Z is selected from the group consisting of substituted or unsubstituted aliphatic group, a substituted or unsubstituted heteroaliphatic group, a click chemistry handle, biotin, a carrier, a polypeptide, a detectable label, a chemical compound or a nucleic acid. In some embodiments Z is a substituted or unsubstituted aliphatic group. In some embodiments Z is a substituted or unsubstituted heteroaliphatic group. In some embodiments Z is a substituted or unsubstituted aryl, preferably substituted or unsubstituted $(C_7-C_{14})$aryl, preferably with the proviso that Z is not a substituted or unsubstituted monocyclic six-membered aryl. In some embodiments Z is a substituted or unsubstituted arylalkyl, preferably substituted or unsubstituted $(C_6-C_{14})$aryl$(C_1-C_6)$alkyl, preferably with the proviso that Z is not a substituted or unsubstituted monocyclic six-membered aryl. In some embodiments Z is a substituted or unsubstituted heteroaryl, preferably substituted or unsubstituted $(C_3-C_{14})$heteroaryl. In some embodiments Z is a substituted or unsubstituted heteroarylalkyl, preferably substituted or unsubstituted $(C_3-C_{14})$heteroaryl$(C_1-C_6)$alkyl. In some embodiments Z is a substituted or unsubstituted heterocyclyl. In some embodiments Z is a click chemistry handle. In some embodiments Z is a biotin. In some embodiments Z is a carrier. In some embodiments Z is a polypeptide. In some embodiments Z is a detectable label. In some embodiments Z is a chemical compound. In some embodiments Z is a nucleic acid. In some embodiments Z is a carbohydrate. In some embodiments Z is a lipid. In some embodiments Z is not a substituted monocyclic six-membered aryl or unsubstituted monocyclic six-membered aryl. In some embodiments Z is not a substituted phenyl or unsubstituted phenyl. In some embodiments Z is not a phenyl substituted with 1, 2, 3, 4 or 5 substituents selected from the group consisting of —$NO_2$, —$N_3$, halogen, —$NH_2$, hydroxyl, —$OR^{11}$ and —$C(=O)R^{11}$, wherein $R^{11}$ is hydrogen, substituted alkyl or substituted alkynyl.

The introduction or addition of a recognition sequence for TTL at the C-terminus of a polypeptide is done as described herein. For example, such a recognition sequence may be introduced or added by genetic engineering or by synthesis, either chemical protein synthesis or via synthetic biology.

Several factors may affect the rate at which enzymatic reactions proceed: temperature, pH, enzyme concentration, substrate concentration, and the presence of any inhibitors or activators. In some embodiments, it is envisaged that a buffer containing a nucleoside triphosphate, such as ATP, potassium chloride, magnesium chloride, and a reducing agent such as DTT is employed in the method of the invention in order to provide suitable conditions suitable for the TTL to tyrosinate the polypeptide of the invention. Other exemplary conditions are described in Ruediger et al. (1994), loc. cit.

It is envisaged herein that the pH value in the method of the invention in order to provide suitable conditions for the TTL to functionalize the polypeptide of the invention with a compound having a structure according to Formula I is in the range of 5 to 9, preferably 5.5 to 8.5, even more preferably 6 to 8.

Furthermore, it is envisaged herein that the concentration of the compound having a structure according to Formula I in the method of the invention in order to provide suitable conditions for the TTL to tyrosinate the polypeptide of the invention may be in the range of 0.1 mM to 10 mM, preferably 0.25 mM to 5 mM, more preferably 0.5 mM to 3 mM, and even more preferably 1 mM to 2 mM.

It is also envisaged herein that the reaction temperature in the method of the invention in order to provide suitable conditions for the TTL to functionalize the polypeptide of the invention with a compound having a structure according to Formula I may be in the range of 1° C. to 70° C., preferably 5° C. to 65° C., more preferably 10° C. to 60° C., even more preferably 15° C. to 55° C., most preferably 19° C. to 43° C., and for example 19° C. to 37° C.

A suitable reaction time for the TTL to functionalize the polypeptide of the invention with a compound having a structure according to Formula I may be in the range of 5 minutes to 48 hours, preferably 5 minutes to 24 hours, more preferably 5 minutes to 4 hours, even more preferably 10 minutes to 3 hours, still more preferably 1 hour to 3 hours.

The present invention preferably pertains to a "recombinant" or "synthetic" polypeptide. A "synthetic" polypeptide in the context of the present invention refers to a polypeptide that has been obtained by methods of synthetic biology, including solid phase peptide synthesis (SPPS), prior thiol capture strategy, native chemical ligation (NCL), expressed protein ligation (EPL) and Staudinger ligation, and the 0-acyl isopeptide method. Such a synthetic polypeptide contains a TTL recognition sequence that is introduced either by addition or modification of the amino acid sequence of the synthetic polypeptide.

As used herein and throughout the entire description, the term "synthetic" polypeptide as used herein also includes polypeptides which have been treated to alter their natural amino acid sequence, e.g., by deamidation.

As used herein and throughout the entire description, the term "recombinant" in the context of the present invention refers to a polypeptide that is genetically engineering, i.e., modified to introduce or add a recognition sequence for TTL at the C-terminus of a polypeptide. It thus excludes such tubulins which naturally contain a TTL recognition sequence.

As used herein and throughout the entire description, "Modified to introduce a recognition sequence" means that the amino acid sequence of a polypeptide is modified to introduce a TTL recognition sequence, such as replacing or deleting, but not adding or inserting, one or more amino acids in order to build a TTL recognition sequence at the C-terminus of a polypeptide.

As used herein and throughout the entire description, "Modified to add a recognition sequence" means that the amino acid sequence of a polypeptide is modified to add a TTL recognition sequence, i.e., adding or inserting one or more amino acids in order to equip a polypeptide with a TTL recognition sequence at its C-Terminus.

As used herein and throughout the entire description, examples of polypeptides or proteins include recombinant or synthetic hormones, cytokines and lymphokines, antibodies, receptors, adhesion molecules, and enzymes as well as fragments thereof. A non-exhaustive list of desired polypeptides include, e. g., recombinant or synthetic human growth hormone, bovine growth hormone, parathyroid hormone, thyroid stimulating hormone, follicle stimulating hormone growth, luteinizing hormone; hormone releasing factor; lipoproteins; alpha-1-antitrypsin; insulin A-chain; insulin B-chain; proinsulin; calcitonin; glucagon; molecules such as renin; clotting factors such as factor VIIIC, factor IX, tissue factor, and von Willebrands factor; anti-clotting factors such as Protein C, atrial natriuretic factor, lung surfactant; a plasminogen activator, such as urokinase or human urine or tissue-type plasminogen activator (t-PA); bombesin; thrombin; hemopoietic growth factor; tumor necrosis factor-alpha and-beta; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-or B-chain; prorelaxin; mouse gonadotropin-associated peptide; DNase; inhibin; activin; receptors for hormones or growth factors; integrin; protein A or D; rheumatoid factors; a neurotrophic factor such as bone-derived neurotrophic factor (BDNF), neurotrophin-3,-4,-5, or-6 (NT-3, NT-4, NT-5, or NT-6), growth factors including vascular endothelial growth factor (VEGF), nerve growth factor such as NGF-; platelet-derived growth factor (PDGF); fibroblast growth factor such as aFGF, bFGF, FGF-4, FGF-5, FGF-6; epidermal growth factor (EGF); transforming growth factor (TGF) such as TGF-alpha and TGF-beta, including TGF-p1, TGF-p2, TGF-p3, TGF-p4, or TGF-p5; insulin-like growth factor-I and-II (IGF-I and IGF-11); des (1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha,-beta, and-gamma; colony stimulating factors (CSFs), e.g., M-CSF, GM-CSF, and G-CSF; interleukins (ILs), e.g., IL-1 to IL-10; superoxide dismutase; erythropoietin; T-cell receptors; surface membrane proteins e.g., HER2; decoy accelerating factor; viral antigen such as, for example, a portion of the AIDS envelope; transport proteins; homing receptors; addressins; regulatory proteins; antibodies; chimeric proteins such as immunoadhesins and fragments of any of the above-listed polypeptides.

The polypeptide of the invention is modified to comprise a recognition sequence for tubulin-tyrosine ligase (TTL) at its C-terminus, comprising at least the amino acid sequence $X_4X_3X_2X_1$. The term "recognition sequence" or "recognition motif" are used interchangeably herein and refer to a stretch of amino acids that is recognized by the TTL. Such recognition sequences are known in the art; see, e.g., Ruediger et al. (1994), Eur. J. Biochem. 220, 309-320 or Prota e al. (2013), J. Cell. Biol. 200, No. 3, 259-270. Moreover, the skilled person can easily test whether or not an amino acid sequence of interest is a TTL recognition sequence by applying, e.g., the assay "Tyrosination of peptides by TTL" described in Ruediger et al. "Recognized" by the TTL includes binding of the TTL to the recognition motif. The recognition motif advantageously comprises at least 4 amino acids which are designated $X_4$, $X_3$, $X_2$ and $X_1$ herein. In general, "X" can denote any amino acid unless indicated otherwise herein. Amino acids include includes but is not limited to the twenty "standard" amino acids: isoleucine (Ile, I), leucine (Leu, L), lysine (Lys, K), methionine (Met, M), phenylalanine (Phe, F), threonine (Thr, T), tryptophan (Trp, W), valine (Val, V), alanine (Ala, A), asparagine (Asn, N), aspartate (Asp, D), cysteine (Cys, C), glutamate (Glu, E), glutamine (Gln, Q), glycine (Gly, G), proline (Prol, P), serine (Ser, S), tyrosine (Tyr, Y), arginine (Arg, R) and histidine (His, H). The present invention also includes, without limitation, D-configuration amino acids, β-amino acids, amino acids having side chains as well as all non-natural amino acids known to one skilled in the art.

$X_1$ refers to the ultimate C-terminal amino acid in the polypeptide, $X_2$ to the second to the last, and so on. $X_1$ is E, and $X_2$ is selected from E, D or C. $X_3$ is preferably G, S, A, V, or F, whereas $X_4$ is preferably selected from E, D, A, K or P. In some embodiments, $X_5$ (i.e. the next amino acid towards the N-terminus of $X_4$) is selected from E, A and V. In some embodiments, $X_6$ (i.e. the amino acid following $X_5$) can be selected from E, A, K and G. In some embodiments the recognition sequence for tubulin tyrosine ligase has at least the amino acid sequence $X_1X_2X_3X_4$ (SEQ ID No: 9), wherein $X_1$ and $X_2$ is any amino acid, $X_3$ is E, D or C and $X_4$ is E. In some embodiments $X_2$ is G, S, A, V, or F. In some embodiments $X_1$ is E, D, A, K, or P. In some embodiments the recognition sequence is EGEE (SEQ ID No. 2). In general, any combination of $X_1$ and $X_2$ is conceivable which does not abolish the ability of the TTL to recognize the respective recognition motif. The TTL recognition sequence introduced in or added to the polypeptide of the invention can for example be EGEE (SEQ ID No. 2). In one particular embodiment, the TTL recognition sequence is VDSVEG-EGEEEGEE (SEQ ID No. 3), sometimes also referred to herein as TTL reactive motif), SVEGEGEEEGEE (SEQ ID No. 4), SADGEDEGEE (SEQ ID No. 5), SVEAEAEEGEE (SEQ ID No. 6), SYEDEDEGEE (SEQ ID No. 7), or SFEEENEGEE (SEQ ID No. 8). In general, any recognition sequence is envisaged wherein $X_1$ is E and $X_2$ is E, D or C, which is recognized by the TTL. In some embodiments said polypeptide comprises a linker sequence preceding the recognition sequence of tubulin tyrosine ligase.

As used herein and throughout the entire description, the term "having biological activity" means that a polypeptide has a specific functionality. For example, if the polypeptide of the invention is a modified antibody, "having biological activity" can mean, e.g., having antigen-binding activity. If the polypeptide of the invention is a modified enzyme, "having biological activity" can mean, e.g., having enzymatic activity.

The polypeptide can comprise a linker sequence preceding the recognition sequence of tubulin tyrosine ligase. A "linker sequence" (also referred to as a "spacer sequence") is an amino acid sequence that is introduced between the polypeptide of the invention and the TTL recognition sequence, so as to connect the polypeptide and the TTL recognition sequence. A linker sequence can for example be required in order to allow accurate folding of the polypeptide of the invention, and/or to ensure flexibility and accessibility of the TTL recognition sequence. There are a great variety of possible linker sequences and it is within the knowledge of the person skilled in the art to choose a suitable linker sequence based on, e.g., the size, sequence and physical properties (such as hydrophobicity) of the polypeptide of the invention. Linker sequences can be composed of flexible residues like glycine and serine. It may be preferred that the linker sequence does not adopt a secondary structure (such as a α-helical structure or a β-sheet) in order to ensure maximal flexibility of the attached TTL recognition motif.

In the polypeptide of the invention, a compound having a structure according to Formula I can be covalently bonded to said recognition sequence. The compound having a structure according to Formula I may be conjugated to a moiety via Y, Z or the β-methylene-group of the amino acid or amino acid derivative according to formula I. In other words the moiety is connected to Y, Z or the β-methylene-group of the amino acid or amino acid derivative according to formula I. Said moiety may be connected directly at the above mentioned positions or via a spacer, such as an alkyl spacer in between. The moiety is preferably covalently conjugated to group Y, group Z or the β-methylene-group of the amino acid or amino acid derivative according to formula I. The moiety may be conjugated to such group by common methods in the art such as Staudinger reactions (e.g. Staudinger-ligation, Staudinger-Phosphite reaction), strain-promoted cycloadditions, tetrazine ligations, inverse-electron demand Diels-Alder reactions, thiazolidine-forming reactions of aldehydes or ketones with 1,2-aminothiols, oxazolidine-forming reactions of aldehydes or ketones with 1,2-aminoalcohols, acetal-forming reactions of aldehydes or ketones with 1,2-diols, metal-catalyzed, in particular Pd—, Cu, Ni and Fe-catalyzed cross couplings, amide formation and the like. It is also obvious for the skilled person that the group Y, group z or the β-methylene-group of the amino acid or amino acid derivative according to formula I and/or the moiety may require modification in order to be attached to each other.

It is envisaged that a moiety can be attached to the compound having a structure according to Formula I covalently bonded to the polypeptide of the invention, for example, by click chemistry or any other suitable method as described herein. A moiety may thus be conjugated to the compound having a structure according to Formula I of a functionalized polypeptide by a non-peptidic bond, however, in the alternative it may also be conjugated to the compound having a structure according to Formula I of a functionalized polypeptide by a peptidic-bond. The moiety can be also already attached to the compound having a structure according to Formula I. Such compound connected to a moiety can also be connected to a polypeptide into which a recognition sequence for tubulin tyrosine ligase is introduced or added at its C-terminus mediated by TTL, as described above. Said moiety can be a carrier, a polypeptide, a detectable label, a chemical compound, a nucleic acid, a carbohydrate, or a lipid. The polypeptide can be, in particular, an antibody or fragment thereof selected from the group consisting of a monoclonal antibody, chimeric antibody, humanized antibody, human antibody, scFv, a DART, domain antibody, nanobody, an adnectin, an affibody, an anticalin, a DARPin, or an aptamer. The detectable label may comprise a fluorophore, an enzyme (peroxidase, luciferase), a radioisotope, a fluorescent protein, or a fluorescent dye. The chemical compound can be a small molecule, a polymer, such as a synthetic polymer (PEG) or a therapeutic agent. The nucleic acid can be DNA, RNA, or an aptamer.

Alternatively, the moiety that is conjugated to the compound having a structure according to Formula I attached to the polypeptide of the invention is a polypeptide (herein and throughout the entire description referred to as "polypeptide moiety"). Any polypeptide is conceivable that can be attached to the compound having a structure according to Formula I covalently bonded to the polypeptide of the invention. The polypeptide moiety may require modification in order to be able to be attached.

In one particular embodiment, the polypeptide moiety is an antibody or fragment thereof. As is well known in the art, an antibody is an immunoglobulin molecule capable of specific binding to a target, such as a carbohydrate, polynucleotide, lipid, polypeptide, etc., through at least one epitope recognition site, located in the variable region of the immunoglobulin molecule. As used herein and throughout the entire description, the term encompasses monoclonal antibodies, chimeric antibodies, humanized antibodies, human antibodies, scFv, DART, domain antibodies, nanobodies, adnectin, affibodies, anticalins, DARPins, aptamers or functional equivalents thereof of any one of the aforementioned antibody species as well as affinity binders.

The present invention also provides a polypeptide which is obtainable by the methods, particularly by said above methods of the present invention. Such polypeptide obtainable by the methods of the present invention and applied therein may advantageously have a length of more than 19 amino acids and/or may be a polypeptide other than tubulin or the polypeptide may be tubulin.

The conjugation of a moiety to the compound having a structure according to Formula I of a funtionalized polypeptide is done as described herein.

The invention additionally provides a pharmaceutical composition comprising the polypeptide of the invention. A pharmaceutical composition according to the present invention may further comprise one or more pharmaceutically acceptable carriers. In a specific embodiment, the term "pharmaceutically acceptable" means approved by a regulatory agency or other generally recognized pharmacopoeia for use in animals, and more particularly in humans. Pharmaceutically acceptable carriers are well known in the art and include, for example, aqueous solutions such as water, 5% dextrose, or physiologically buffered saline or other solvents or vehicles such as glycols, glycerol, oils such as olive oil, or injectable organic esters that are suitable for administration to a human or non-human subject. Particular exemplary pharmaceutically acceptable carriers include (biodegradable) liposomes; microspheres made of the biodegradable polymer poly(D,L-lactic-coglycolic acid (PLGA), albumin microspheres; synthetic polymers (soluble); nanofibers, protein-DNA complexes; protein conjugates; erythrocytes; or virosomes. Various carrier based dosage forms comprise solid lipid nanoparticles (SLNs), polymeric nanoparticles, ceramic nanoparticles, hydrogel nanoparticles, copolymerized peptide nanoparticles, nanocrystals and nanosuspensions, nanocrystals, nanotubes and nanowires, functionalized nanocarriers, nanospheres, nanocapsules, liposomes, lipid emulsions, lipid microtubules/microcylinders, lipid microbubbles, lipospheres, lipopolyplexes, inverse lipid micelles, dendrimers, ethosomes, multicomposite ultrathin capsules, aquasomes, pharmacosomes, colloidosomes, niosomes, discomes, proniosomes, microspheres, microemulsions and polymeric micelles. Other suitable pharmaceutically acceptable carriers and excipients are inter alia described in Remington's Pharmaceutical Sciences, $15^{th}$ Ed., Mack Publishing Co., New Jersey (1991) and Bauer et al., Pharmazeutische Technologie, $5^{th}$ Ed., Govi-Verlag Frankfurt (1997).See, e.g., Remington: The Science and Practice of Pharmacy, $21^{st}$ edition; Lippincott Williams & Wilkins, 2005.

In some embodiments, a pharmaceutically acceptable carrier or composition is sterile. A pharmaceutical composition can comprise, in addition to the active agent, physiologically acceptable compounds that act, for example, as bulking agents, fillers, solubilizers, stabilizers, osmotic agents, uptake enhancers, etc. Physiologically acceptable compounds include, for example, carbohydrates, such as glucose, sucrose, lactose; dextrans; polyols such as mannitol; antioxidants, such as ascorbic acid or glutathione; preservatives; chelating agents; buffers; or other stabilizers or excipients.

The choice of a pharmaceutically acceptable carrier(s) and/or physiologically acceptable compound(s) can depend for example, on the nature of the active agent, e.g., solubility, compatibility (meaning that the substances can be present together in the composition without interacting in a manner that would substantially reduce the pharmaceutical efficacy of the pharmaceutical composition under ordinary use situations) and/or route of administration of the composition.

Pharmaceutical compositions of the invention comprise a therapeutically effective amount of the polypeptide of the invention and can be formulated in various forms, e.g. in solid, liquid, gaseous or lyophilized form and may be, inter alia, in the form of an ointment, a cream, transdermal patches, a gel, powder, a tablet, solution, an aerosol, granules, pills, suspensions, emulsions, capsules, syrups, liquids, elixirs, extracts, tincture or fluid extracts or in a form which is particularly suitable for topical or oral administration. A variety of routes are applicable for administration of the polypeptide of the invention, including, but not limited to, orally, topically, transdermally, subcutaneously, intravenously, intraperitoneally, intramuscularly or intraocularly. However, any other route may readily be chosen by the person skilled in the art if desired.

The pharmaceutical compositions can be used for the treatment of a wide variety of different diseases and disorders. Thus the invention also envisages methods of treatment comprising administering an inventive polypeptide to a subject in need thereof. The subject is typically a mammal, e.g., a human. In some embodiments the subject is a non-human animal that serves as a model for a disease or disorder that affects humans. The animal model may be used, e.g., in preclinical studies, e.g., to assess efficacy and/or determine a suitable dose. In some embodiments, an inventive protein is administered prophylactically, e.g., to a subject who does not exhibit signs or symptoms of the disease or disorder (but may be at increased risk of developing the disorder or is expected to develop the disease or disorder). In some embodiments an inventive protein is administered to a subject who has developed one or more signs or symptoms of the disease or disorder, e.g., the subject has been diagnose as having the disease or disorder. Optionally, the method comprises diagnosing the subject as having a disease or disorder for which the protein is an appropriate treatment. By "therapeutically effective amount" is meant an amount of the polypeptide of the invention that elicits a desired therapeutic effect. The exact amount dose will depend on the purpose of the treatment, and will be ascertainable by one skilled in the art using known techniques. As is known in the art and described above, adjustments for age, body weight, general health, sex, diet, drug interaction and the severity of the condition may be necessary, and will be ascertainable with routine experimentation by those skilled in the art.

The pharmaceutical composition of the present invention may further comprise one or more additional therapeutic agents. Preferably, said agents are therapeutically effective for treatment of the respective disease.

Further, the invention relates to a diagnostic composition comprising the polypeptide of the invention. The diagnostic composition may comprise means for diagnosis, such as detection agents.

Also, a kit comprising means for performing the methods described herein is provided. The kit may comprise an expression vector which allows expression of a protein of interest fused at its C-Terminus to a recognition sequence for tubulin tyrosine ligase, tubulin tyrosine ligase and a compound having a structure according to formula I

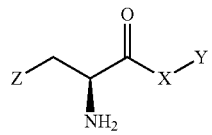

(I)

wherein

X is O, NR$^1$ or S;

Y is selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl;

Z is selected from the group consisting of substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl;

R$^1$ is selected from the group consisting of hydrogen, substituted or unsubstituted $(C_1-C_6)$alkyl, substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_6-C_{14})$aryl and substituted or unsubstituted $(C_3-C_{14})$heteroaryl; and with the proviso that Z is not a substituted or unsubstituted monocyclic six-membered aryl.

Alternatively, the kit may comprise comprises an expression vector which allows expression of a protein of interest fused at its C-Terminus to a recognition sequence for tubulin tyrosine ligase, tubulin tyrosine ligase and a compound having a structure according to formula I

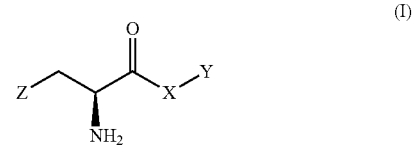

(I)

wherein

X is O, NR$^1$ or S;

Y is selected from the group consisting of a substituted or unsubstituted aliphatic group, a substituted or unsubstituted heteroaliphatic group, substituted or unsubstituted aryl, substituted or unsubstituted arylalkyl, substituted or unsubstituted heteroaryl, substituted or unsubstituted heteroarylalkyl, substituted or unsubstituted heterocyclyl, a click chemistry handle, biotin, a carrier, a polypeptide, a detectable label, a chemical compound, a nucleic acid, a carbohydrate, or a lipid;

Z is selected from the group consisting of a substituted or unsubstituted aliphatic group, a substituted or unsubstituted heteroaliphatic group, substituted or unsubstituted aryl, substituted or unsubstituted arylalkyl, substituted or unsubstituted heteroaryl, substituted or unsubstituted heteroarylalkyl, substituted or unsubstituted heterocyclyl, a click chemistry handle, biotin, a carrier, a polypeptide, a detectable label, a chemical compound, a nucleic acid, a carbohydrate, or a lipid;

R$^1$ is selected from the group consisting of hydrogen, substituted or unsubstituted $(C_1-C_6)$alkyl, substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_6-C_{14})$aryl and substituted or unsubstituted $(C_3-C_{14})$heteroaryl; and with the proviso that Z is not a substituted or unsubstituted monocyclic six-membered aryl.

Such a polypeptide may be an antibody or fragment thereof selected from the group consisting of a monoclonal antibody, chimeric antibody, humanized antibody, human antibody, scFv, a DART, domain antibody, nanobody, an adnectin, an affibody, an anticalin, a DARPin, or an aptamer. Such a detectable label may comprise a fluorophore, an enzyme (peroxidase, luciferase), a radioisotope, a PET-tracer, a fluorescent protein, or a fluorescent dye. Such a chemical compound may be a small molecule, a polymer, such as a synthetic polymer (PEG) or a therapeutic agent. Such a nucleic acid may be DNA, RNA, or an aptamer.

The kit may comprise additionally a buffer solution as described herein which can be used for the functionalization of the polypeptide of the invention with a compound having a structure according to Formula I. In some embodiments the protein of interest is not tubulin.

As used herein and throughout the entire description, the term "expression vector" refers to a carrier nucleic acid molecule which has the ability to incorporate and transcribe heterologous nucleic acid sequences in a host, host cell or in vitro. Selection of appropriate expression or transcription vectors is within the knowledge of those skilled in the art. Many prokaryotic and eukaryotic expression vectors are commercially available. Examples of vectors used in the present invention include plasmids, viruses, phagemids, bacteriophages, retroviruses, cosmids or F-factors. Specific vectors may be used for specific host or host cell types. Numerous examples of vectors are known in the art and are commercially available (Sambrook and Russell, Molecular Cloning: A Laboratory Manual, 3rd edition (Jan. 15, 2001) Cold Spring Harbor Laboratory Press, ISBN: 0879695765). Examples of vectors commonly used with bacteria include the pET series (Novagen), pGEX series (Ge Healthcare), pBAD-series (Invitrogen). Examples of vectors in yeasts are the pPic series for *Pichia* (Invitrogen), the pKlac system from *Kluyveromyces lactis* (New England biolabs), *S. cerevisae* vectors (Patel et al. Biotechnol Lett. 2003 25(4):331-334) and the pYes system for *S. cereviseae* (Invitrogen). Examples of vectors for use in fungi are the pBAR series (described in Pall et al.1993. Fungal Genetics Newsletter 40: 59-61). The plEx plasmid based system (Merck) or the baculovirus based system (Merck) are two examples of systems useful for insect cells. Examples of vectors for use in insect cells include the tetracycline regulated systems pTet and pTre, the adenovirus-based system Adeno-X, the retrovirus-based system Retro-X (Clontech) and the pcDNA vectors (Invitrogen). The expression vector may be naturally-occurring or artificial, linear or circular. The vector may also contain an intron.

Also provided by the present invention is the use of tubulin tyrosine ligase for functionalizing a polypeptide having at its C-terminus a recognition sequence for tubulin tyrosine ligase, with a compound having a structure according to formula I

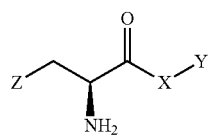

(I)

wherein
X is O, $NR^1$ or S;
Y is selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl;
Z is selected from the group consisting of substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl;
$R^1$ is selected from the group consisting of hydrogen, substituted or unsubstituted ($C_1$-$C_6$)alkyl, substituted or unsubstituted ($C_2$-$C_6$)alkenyl, substituted or unsubstituted ($C_2$-$C_6$)alkynyl, substituted or unsubstituted ($C_3$-$C_8$)cycloalkyl, substituted or unsubstituted ($C_6$-$C_{14}$)aryl and substituted or unsubstituted ($C_3$-$C_{14}$)heteroaryl; and
with the proviso that Z is not a substituted or unsubstituted monocyclic six-membered aryl.

Also provided by the present invention is the use of tubulin tyrosine ligase for functionalizing a polypeptide having at its C-terminus a recognition sequence for tubulin tyrosine ligase, with a compound having a structure according to formula I

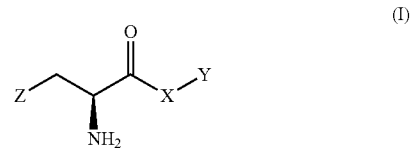

(I)

wherein
X is O, $NR^1$ or S;
Y is selected from the group consisting of a substituted or unsubstituted aliphatic group, substituted or unsubstituted aryl, substituted or unsubstituted arylalkyl, substituted or unsubstituted heteroaryl, substituted or unsubstituted heteroarylalkyl, a substituted or unsubstituted heteroaliphatic group, substituted or unsubstituted heterocyclyl, a click chemistry handle, biotin, a carrier, a polypeptide, a detectable label, a chemical compound, a nucleic acid, a carbohydrate, or a lipid;
Z is selected from the group consisting of a substituted or unsubstituted aliphatic group, a substituted or unsubstituted heteroaliphatic group, substituted or unsubstituted aryl, substituted or unsubstituted arylalkyl, substituted or unsubstituted heteroaryl, substituted or unsubstituted heteroarylalkyl, substituted or unsubstituted heterocyclyl, a click chemistry handle, biotin, a carrier, a polypeptide, a detectable label, a chemical compound, a nucleic acid, a carbohydrate, or a lipid;
$R^1$ is selected from the group consisting of hydrogen, substituted or unsubstituted ($C_1$-$C_6$)alkyl, substituted or unsubstituted ($C_2$-$C_6$)alkenyl, substituted or unsubstituted ($C_2$-$C_6$)alkynyl, substituted or unsubstituted ($C_3$-$C_8$)cycloalkyl, substituted or unsubstituted ($C_6$-$C_{14}$)aryl and substituted or unsubstituted ($C_3$-$C_{14}$)heteroaryl; and
with the proviso that Z is not a substituted or unsubstituted monocyclic six-membered aryl.

Such a polypeptide that is conjugated to a functionalized polypeptide may be an antibody or fragment thereof selected from the group consisting of a monoclonal antibody, chimeric antibody, humanized antibody, human antibody, scFv, a DART, domain antibody, nanobody, an adnectin, an affibody, an anticalin, a DARPin, or an aptamer. Such a detectable label may comprise a fluorophore, an enzyme (peroxidase, luciferase), a radioisotope, a PET-tracer, a fluorescent protein, or a fluorescent dye. Such a chemical compound may be a small molecule, a polymer, such as a synthetic polymer (PEG) or a therapeutic agent. Such a nucleic acid may be DNA, RNA, or an aptamer.

The polypeptide is preferably a polypeptide other than tubulin.

The embodiments and definitions of terms described in the context of the means such as polypeptides of the invention are equally applicable to the methods and uses described above, *mutatis mutandis*.

Further, the invention shall be explained in more detail by the following Examples.

Items

The present invention can also be characterized by the following items:

1. A method for the production of a functionalized polypeptide comprising
   (a) introducing or adding at the C-terminus of a polypeptide a recognition sequence for tubulin tyrosine ligase;
   (b) contacting the polypeptide obtained in step (a) in the presence of tubulin tyrosine ligase and a compound under conditions suitable for the tubulin tyrosine ligase to functionalize said polypeptide with said compound, wherein said compound having a structure according to Formula I

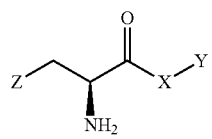

wherein
X is O, NR$^1$ or S;
Y is selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl;
Z is selected from the group consisting of substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl; and
R$^1$ is selected from the group consisting of hydrogen, substituted or unsubstituted (C$_1$-C$_6$)alkyl, substituted or unsubstituted (C$_2$-C$_6$)alkenyl, substituted or unsubstituted (C$_2$-C$_6$)alkynyl, substituted or unsubstituted (C$_3$-C$_8$)cycloalkyl, substituted or unsubstituted (C$_6$-C$_{14}$)aryl and substituted or unsubstituted (C$_3$-C$_{14}$)heteroaryl;
with the proviso that Z is not a substituted or unsubstituted monocyclic six-membered aryl.

2. The method of item 1, further comprising
   (c) conjugating a moiety to said functionalized polypeptide obtained in step (b).

3. A method for the production of a functionalized polypeptide comprising
   (a') introducing or adding at the C-terminus of a polypeptide a recognition sequence for tubulin tyrosine ligase; and
   (b') contacting the polypeptide obtained in step (a') in the presence of tubulin tyrosine ligase and a compound conjugated to a moiety under conditions suitable for the tubulin tyrosine ligase to functionalize said polypeptide with said compound conjugated to said moiety, wherein said compound having a structure according to Formula I

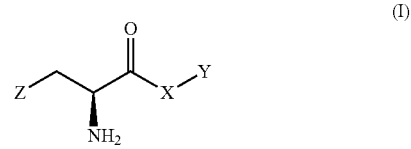

wherein
X is O, NR$^1$ or S;
Y is selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl;
Z is selected from the group consisting of substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl; and
R$^1$ is selected from the group consisting of hydrogen, substituted or unsubstituted (C$_1$-C$_6$)alkyl, substituted or unsubstituted (C$_2$-C$_6$)alkenyl, substituted or unsubstituted (C$_2$-C$_6$)alkynyl, substituted or unsubstituted (C$_3$-C$_8$)cycloalkyl, substituted or unsubstituted (C$_6$-C$_{14}$)aryl and substituted or unsubstituted (C$_3$-C$_{14}$)heteroaryl, and
wherein said moiety is conjugated to the Y-group and/or Z-group, with the proviso that
(i) said Y group is not hydrogen when conjugated to said moiety;
(ii) Z is not a substituted or unsubstituted monocyclic six-membered aryl.

4. The method of any one of items 1-3, wherein the compound having a structure according to formula I is characterized in that, X is O, NR¹ or S;

Y is hydrogen or substituted or unsubstituted $(C_1-C_6)$ alkyl;

Z is selected from the group consisting of substituted or unsubstituted $(C_1-C_6)$alkyl, substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_7-C_{14})$aryl, substituted or unsubstituted $(C_6-C_{14})$aryl$(C_1-C_6)$alkyl, substituted or unsubstituted $(C_3-C_{14})$heteroaryl, substituted or unsubstituted $(C_3-C_{14})$heteroaryl$(C_1-C_6)$alkyl, substituted or unsubstituted $(C_3-C_{14})$heterocyclyl, substituted or unsubstituted $(C_1-C_6)$heteroalkyl, substituted or unsubstituted $(C_2-C_6)$heteroalkenyl and substituted or unsubstituted $(C_2-C_6)$heteroalkynyl; and R¹ is hydrogen or substituted or unsubstituted $(C_1-C_6)$ alkyl.

5. The method of any one of items 1-4, wherein the compound having a structure according to formula I is characterized in that, X is O, NR¹ or S;

Y is hydrogen or substituted or unsubstituted $(C_1-C_6)$ alkyl;

Z is selected from the group consisting of substituted or unsubstituted 2H-1-benzopyranyl (2H-chromenyl), substituted or unsubstituted benzodihydropyranyl (chromanyl), substituted or unsubstituted 4H-1-benzopyranyl (4H-chromenyl), substituted or unsubstituted 1H-2-benzopyranyl (1H-isochromenyl), substituted or unsubstituted isochromanyl, substituted or unsubstituted 3H-2-benzopyranyl (3H-isochromenyl), substituted or unsubstituted 1-benzopyran-4-on-yl (chromonyl), substituted or unsubstituted 4-chromanonyl, substituted or unsubstituted 1-benzopyran-2-on-yl (coumarinyl), substituted or unsubstituted dihydrocoumarinyl, substituted or unsubstituted 3-isochromanonyl, substituted or unsubstituted 2-coumaranon-yl, substituted or unsubstituted $(C_1-C_6)$alkyl, substituted or unsubstituted $(C_1-C_6)$heteroalkyl, substituted or unsubstituted imidazolyl, substituted or unsubstituted azaindolyl including 7-azaindolyl, 6-azaindolyl, 5-azaindolyl and 4-azaindolyl and substituted or unsubstituted indolyl; and R¹ is hydrogen or substituted or unsubstituted $(C_1-C_6)$ alkyl.

6. A method for the production of a functionalized polypeptide comprising (a") introducing or adding at the C-terminus of a polypeptide a recognition sequence for tubulin tyrosine ligase;

(b") contacting the polypeptide obtained in step (a) in the presence of tubulin tyrosine ligase and a compound under conditions suitable for the tubulin tyrosine ligase to functionalize said polypeptide with said compound having a structure according to Formula I

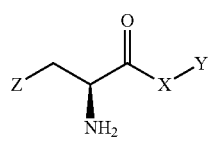

(I)

wherein

X is O, NR¹ or S;

Y is selected from the group consisting of a substituted or unsubstituted aliphatic group, a substituted or unsubstituted heteroaliphatic group, substituted or unsubstituted aryl, substituted or unsubstituted arylalkyl, substituted or unsubstituted heteroaryl, substituted or unsubstituted heteroarylalkyl, substituted or unsubstituted heterocyclyl, a click chemistry handle, biotin, a carrier, a polypeptide, a detectable label, a chemical compound, a nucleic acid, a carbohydrate, or a lipid;

Z is selected from the group consisting of a substituted or unsubstituted aliphatic group, a substituted or unsubstituted heteroaliphatic group, substituted or unsubstituted aryl, substituted or unsubstituted arylalkyl, substituted or unsubstituted heteroaryl, substituted or unsubstituted heteroarylalkyl, substituted or unsubstituted heterocyclyl, a click chemistry handle, biotin, a carrier, a polypeptide, a detectable label, a chemical compound, a nucleic acid, a carbohydrate, or a lipid; and R¹ is selected from the group consisting of hydrogen, substituted or unsubstituted $(C_1-C_6)$alkyl, substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_6-C_{14})$aryl and substituted or unsubstituted $(C_3-C_{14})$heteroaryl;

with the proviso that Z is not a substituted or unsubstituted monocyclic six-membered aryl.

7. The method of any of the preceding items, wherein the recognition sequence for tubulin tyrosine ligase has at least the amino acid sequence $X_1X_2X_3X_4$ (SEQ ID No: 9), wherein $X_1$ and $X_2$ is any amino acid, $X_3$ is E, D or C and $X_4$ is E.

8. The method of any one of preceding items, wherein $X_2$ is G, S, A, V, or F.

9. The method of any one of the preceding items, wherein $X_1$ is E, D, A, K, or P.

10. The method of any one of the preceding items, wherein the recognition sequence is EGEE (SEQ ID No. 2).

11. The method of any one of the preceding items, wherein the recognition sequence is VDSVEGEGEEEGEE (SEQ ID No. 3), SVEGEGEEEGEE (SEQ ID No. 4), SADGEDEGEE (SEQ ID No. 5), SVEAEAEEGEE (SEQ ID No. 6), SYEDEDEGEE (SEQ ID No. 7), or SFEEENEGEE (SEQ ID No. 8).

12. The method of any one of the preceding items, wherein said polypeptide comprises a linker sequence preceding the recognition sequence of tubulin tyrosine ligase.

13. The method of any one of items 1-5 and 7-12, wherein said moiety conjugated to a functionalized polypeptide is a carrier, a polypeptide, a detectable label, a chemical compound, a nucleic acid, a carbohydrate, or a lipid.

14. The method of item 6 and 13, wherein the polypeptide moiety is an antibody or fragment thereof selected from the group consisting of a monoclonal antibody, chimeric antibody, humanized antibody, human antibody, scFv, a DART, domain antibody, nanobody, an adnectin, an affibody, an anticalin, a DARPin, or an aptamer.

15. The method of item 6 and 13, wherein the detectable label comprises a fluorophore, an enzyme (peroxidase, luciferase), a radioisotope, a fluorescent protein, or a fluorescent dye.

16. The method of item 6 and 13, wherein said chemical compound is a small molecule, a polymer, such as a synthetic polymer (PEG) or a therapeutic agent.

17. The method of item 6 and 13, wherein the nucleic acid is DNA, RNA, or an aptamer.

18. The method of any one of the preceding items, wherein the suitable conditions comprise a buffer containing a nucleoside triphosphate, such as ATP, potassium chloride, magnesium chloride, a reducing agent such as DTT.

19. The method of any of the preceding items, wherein the suitable conditions further comprise a pH-value in the range of 5 to 9.

20. The method of any of the preceding items, wherein the suitable conditions further comprise a concentration of the compound having a structure according to formula I in the range of 0.1 mM to 10 mM.

21. The method of any of the preceding items, wherein the suitable conditions further comprise a reaction temperature in the range of 1° C. to 70° C., preferably 19° C. to 37° C.

22. The method of any of the preceding items, wherein the suitable conditions further comprise a reaction time in the range of 5 minutes to 4 hours, preferably 1 hour to 3 hours.

23. The method of any one of the preceding items, wherein said polypeptide has a length of more than 19 amino acids.

24. The method of any one of the preceding items, wherein said polypeptide is a polypeptide other than tubulin.

25. A polypeptide which is obtainable by the method of any one of items 1 to 24, wherein said polypeptide is preferably a polypeptide other than tubulin.

26. A diagnostic composition comprising the polypeptide of item 25.

27. A pharmaceutical composition comprising the polypeptide of item 25.

28. A kit comprising means for performing the method of any one of items 1 to 24.

29. The kit of item 28 which comprises an expression vector which allows expression of a protein of interest fused at its C-Terminus to a recognition sequence for tubulin tyrosine ligase, tubulin tyrosine ligase and a compound having a structure according to formula I

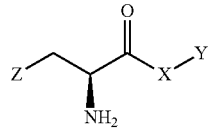

wherein

X is O, NR$^1$ or S;

Y is selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl;

Z is selected from the group consisting of substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl; and R$^1$ is selected from the group consisting of hydrogen, substituted or unsubstituted (C$_1$-C$_6$)alkyl, substituted or unsubstituted (C$_2$-C$_6$)alkenyl, substituted or unsubstituted (C$_2$-C$_6$)alkynyl, substituted or unsubstituted (C$_3$-C$_8$)cycloalkyl, substituted or unsubstituted (C$_6$-C$_{14}$)aryl and substituted or unsubstituted (C$_3$-C$_{14}$)heteroaryl;

with the proviso that Z is not a substituted or unsubstituted monocyclic six-membered aryl.

30. The kit of item 28 which comprises an expression vector which allows expression of a protein of interest fused at its C-Terminus to a recognition sequence for tubulin tyrosine ligase, tubulin tyrosine ligase and a compound having a structure according to formula I

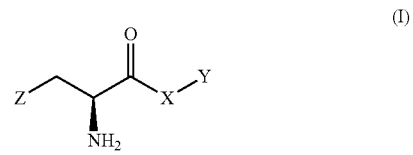

wherein

X is O, NR$^1$ or S;

Y is selected from the group consisting of a substituted or unsubstituted aliphatic group, a substituted or unsubstituted heteroaliphatic group, substituted or unsubstituted aryl, substituted or unsubstituted arylalkyl, substituted or unsubstituted heteroaryl, substituted or unsubstituted heteroarylalkyl, substituted or unsubstituted heterocyclyl, a click chemistry handle, biotin, a carrier, a polypeptide, a detectable label, a chemical compound, a nucleic acid, a carbohydrate, or a lipid;

Z is selected from the group consisting of a substituted or unsubstituted aliphatic group, a substituted or unsubstituted heteroaliphatic group, substituted or unsubstituted aryl, substituted or unsubstituted arylalkyl, substituted or unsubstituted heteroaryl, substituted or unsubstituted heteroarylalkyl, substituted or unsubstituted heterocyclyl, a click chemistry handle, biotin, a carrier, a polypeptide, a detectable label, a chemical compound, a nucleic acid, a carbohydrate, or a lipid; and R$^1$ is selected from the group consisting of hydrogen, substituted or unsubstituted (C$_1$-C$_6$)alkyl, substituted or unsubstituted (C$_2$-C$_6$)alkenyl, substituted or unsubstituted (C$_2$-C$_6$)alkynyl, substituted or unsubstituted (C$_3$-C$_8$)cycloalkyl, substituted or unsubstituted (C$_6$-C$_{14}$)aryl and substituted or unsubstituted (C$_3$-C$_{14}$)heteroaryl;

with the proviso that Z is not a substituted or unsubstituted monocyclic six-membered aryl.

31. Use of tubulin tyrosine ligase for functionalizing a polypeptide having at its C-terminus a recognition sequence for tubulin tyrosine ligase, with a compound having a structure according to formula I

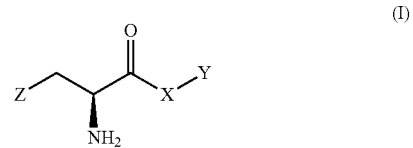

wherein

X is O, NR$^1$ or S;

Y is selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl;

Z is selected from the group consisting of substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl; and $R^1$ is selected from the group consisting of hydrogen, substituted or unsubstituted $(C_1-C_6)$alkyl, substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_6-C_{14})$aryl and substituted or unsubstituted $(C_3-C_{14})$heteroaryl;

with the proviso that Z is not a substituted or unsubstituted monocyclic six-membered aryl.

32. Use of tubulin tyrosine ligase for functionalizing a polypeptide having at its C-terminus a recognition sequence for tubulin tyrosine ligase, with a compound having a structure according to formula I

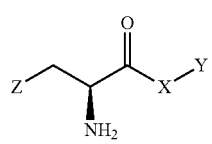

(I)

wherein

X is O, $NR^1$ or S;

Y is selected from the group consisting of a substituted or unsubstituted aliphatic group, substituted or unsubstituted aryl, substituted or unsubstituted arylalkyl, substituted or unsubstituted heteroaryl, substituted or unsubstituted heteroarylalkyl, a substituted or unsubstituted heteroaliphatic group, substituted or unsubstituted heterocyclyl, a click chemistry handle, biotin, a carrier, a polypeptide, a detectable label, a chemical compound, a nucleic acid, a carbohydrate, or a lipid;

Z is selected from the group consisting of a substituted or unsubstituted aliphatic group, a substituted or unsubstituted heteroaliphatic group, substituted or unsubstituted aryl, substituted or unsubstituted arylalkyl, substituted or unsubstituted heteroaryl, substituted or unsubstituted heteroarylalkyl, substituted or unsubstituted heterocyclyl, a click chemistry handle, biotin, a carrier, a polypeptide, a detectable label, a chemical compound, a nucleic acid, a carbohydrate, or a lipid; and $R^1$ is selected from the group consisting of hydrogen, substituted or unsubstituted $(C_1-C_6)$alkyl, substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_6-C_{14})$aryl and substituted or unsubstituted $(C_3-C_{14})$heteroaryl;

with the proviso that Z is not a substituted or unsubstituted monocyclic six-membered aryl.

33. The use of any one of items 31-32, wherein the polypeptide is a polypeptide other than tubulin.

EXAMPLES

1) General Information

Analytical HPLC was conducted on a SHIMADZU HPLC system (Shimadzu Corp., Kyoto, Japan) with a SIL-20A autosampler, 2 pumps $LC_2$ AAT, a 2489 UV/Visible detector, a CTO-20A column oven and an RF-10 A $X_2$ fluorescence detector using an Agilent Eclipse C18 5 µm, 250×4.6 mm RP-HPLC-column with a flow rate of 0.5 mL/min. The following gradient was used: Method A: (A=$H_2O$+0.1% TFA, B=MeCN+0.1% TFA) 10-100% B, 0-30 min, 100% B 31-40 min, 100-10% B 40-45 min. UV chromatograms were recorded at 220 nm.

Analytical UPLC: UPLC-UV traces were obtained on a Waters H-class instrument equipped with a Quaternary Solvent Manager, a Waters autosampler and a Waters TUV detector connected to a 3100 mass detector with an Acquity UPLC-BEH C18 1.7 µm, 2.1×50 mm RP column with a flow rate of 0.6 mL/min. The following gradient was used: Method B: (A=$H_2O$+0.1% TFA, B=MeCN+0.1% TFA) 5-95% B 0-3 min, 95% B 3-5 min. UPLC-UV chromatograms were recorded at 220 nm.

Preparative HPLC was performed on a Gilson PLC 2020 system (Gilson Inc., Wis., Middleton, USA) using a Macherey-Nagel Nucleodur C18 HTec Spum column (Macherey-Nagel GmbH & Co. Kg, Duren, Germany). The following gradient was used: Method C: (A=$H_2O$+0.1% TFA, B=MeCN+0.1% TFA) flow rate 32 mL/min, 10% B 0-5 min, 10-100% B 5-35 min, 100% B 35-40 min. Method D: (A=$H_2O$+0.1% TFA, B=MeCN+0.1% TFA) 10% B 0-5 min, 10-100% B 5-50 min, 100% B 50-55 min.

Analytical HPLC-MSMS: Peptides were analyzed by a Ultimate 3000 nanoLC system (Thermo Scientific, Waltham, Mass., USA) connected to an LTQ Orbitrap XL mass spectrometer (Thermo Scientific). LC separations were performed on a capillary column (Acclaim PepMap100, C18, 3 µm, 100 Å, 75 µm i.d. ×25 cm, Thermo Scientific) at an eluent flow rate of 300 nL/min. The following gradient was used: Method E: (A=$H_2O$+0.1% formic acid, B=MeCN+0.1% formic acid) 3-50% B 0-50 min Mass spectra were acquired in a data-dependent mode with one MS survey scan with a resolution of 30,000 (LTQ Orbitrap XL) or 60,000 (Orbitrap Elite) and MS/MS scans of the five or 5 most intense precursor ions in the linear trap quadrupole, respectively.

Column chromatography was performed on silica gel (Acros Silica gel 60 Å, 0.035-0.070 mm).

High resolution mass spectra (HRMS) were measured on an Acquity UPLC system and a LCT Premier™ (Waters Micromass, Milford, Mass., USA) time-of-flight mass spectrometer with electrosp ray ionization using water and acetonitrile (10-90% gradient) with 0.1% formic acid as eluent.

NMR spectra were recorded with a Bruker Ultrashield 300 MHz spectrometer (Bruker Corp. Billerica, Mass., USA) at ambient temperature. The chemical shifts are reported in ppm relatively to the residual solvent peak.

Reagents and solvents were, unless stated otherwise, commercially available as reagent grade and did not require further purification. Resins and Fmoc-protected amino acids were purchased from IRIS BioTEch (Marktredwitz, Germany) or Novabiochem (Darmstadt, Germany).

SPPS was either carried out manually or with an Activo-P11 automated peptide synthesizer (Activotec, Cambridge, UK) via standard Fmoc-based conditions (Fast-moc protocol with HOBt/HBUT conditions).

2) Abbreviations

Bn benzyl
Cbz carboxybenzyl
Da Dalton
DIC diisopropylcarbodiimide
DIPEA diisopropylethylamine
DMADHP N,N-dimethyl-2-amino-4,6-dihydropyrimidine
DMF N,N-dimethylformamide
DTT dithiotreitol
EtOAc ethylacetate
eq equivalents
Em emission wavelength in nanometer
Ex excitation wavelength in nanometer
Fmoc fluorenylmethyloxycarbonyl
HBTU N,N',N'-Tetramethyl-O-(1H-benzotriazol-1-yl)uranium hexafluorophosphate
HOAc acetic acid
HOBt hydroxybenzotriazole
HPLC high performance liquid chromatography
HRMS high resolution mass spectrometry
IPTG isopropyl-β-D-thiogalactopyranosid
LC liquid chromatography
MS/MS Tandem mass spectrometry
MeCN acetonitrile
MES 2-(N-Morpholino)ethanesulfonic acid
MHz megahertz
PMSF phenylmethylsulfonylfluorid
RP-HPLC reversed phase high performance liquid chromatography
SDS-PAGE sodium dodecyl sulfate polyacrylamide gel electrophoresis
SPPS solid phase peptide synthesis
TFA trifluoroacetic acid
THF tetrahydrofurane
TIS triisopropylsilane
TTL tubulin-tyrosine ligase
Tub-tag Tubulin derived TTL recognition sequence
UPLC ultra performance liquid chromatography
UV ultraviolet

3) Synthesis of Tyr(o-propargyl) (5)

The synthesis of the Tyr(o-propargyl) was performed according to a known procedure in literature (S. Milles, S. Tyagi, N. Banterle, C. Koehler, V. VanDelinder, T. Plass, A. P. Neal, E. A. Lemke, *J Am Chem Soc* 2012, 134, 5187-5195).

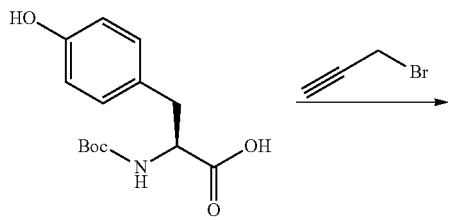

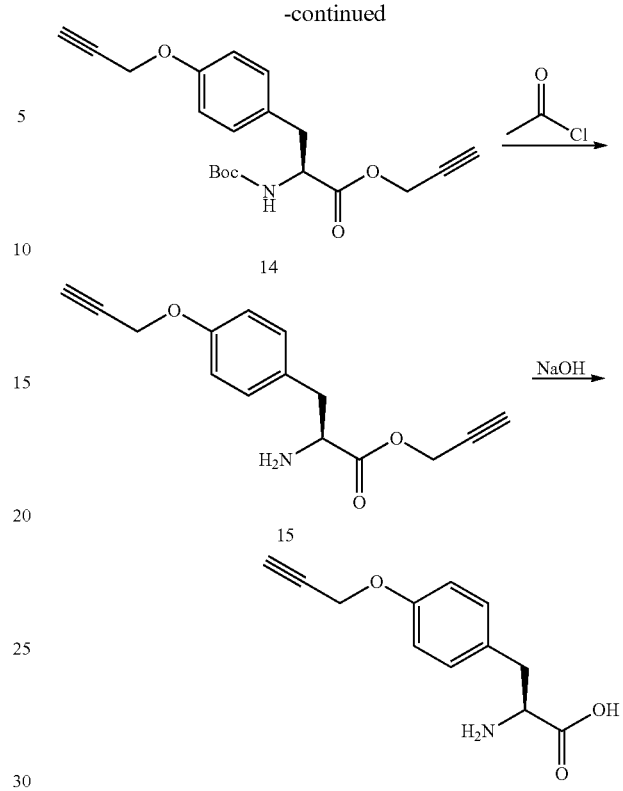

3.1) Intermediate 14

Boc-L-Tyr-OH (2.51 g, 8.9 mmol) and K2003 were suspended in dry DMF (20 mL). Propargyl bromide (80% in toluene, 2.88 mL, 26.75 mmol) was slowly added stirred at ambient temperature for 24 h. H2O and Et2O (50 mL each) were added and the org. phase separated and the aqueous layer extracted with Et2O (2×40 mL). The combined org. phases were dried over MgSO4 and evaporated under reduced pressure to give 2.85 g (90%) of intermediate 14. The compound was used without further purification.

3.2) Intermediate 15

Acetyl chloride (7.27 g, 658 mL, 92.6 mmol) was slowly added to dry methanol (55 mL) at 0° C. and added to compound 14 (6.02 g, 16.86 mmol) at 0° C. and slowly warmed to ambient temperature. The mixture was stirred for additional 20 h and all volatile compounds removed to give the HCl salt of 15 as a white solid (4.01 g, 13.63 mmol, 80%). The compound was used without further purification.

3.3) Tyr(o-propargyl) (5)

15 (4.01 g, 13.63 mmol) was dissolved in MeOH (15 mL) and aqueous 2N NaOH (20 mL) was added slowly. The mixture was stirred at ambient temperature for 20 h and acidified with conc. HCl and stored at 4° C. for 20 h. The white precipitate was filtered of and dried in the vacuum to yield the HCl-salt of 5 (3.05 g, 11 mmol, 88%). $^1$H NMR (300 MHz, DMSO-$d_6$) δ 7.20 (d, J=8.3 Hz, 2H), 6.90 (d, J=8.3 Hz, 2H), 4.75 (d, J=2.4 Hz, 2H), 3.56 (t, J=2.3 1H), 3.45 (dd, J=7.8, 4.6 Hz, 1H), 3.08 (dd, J=14.4, 4.6 Hz, 1H), 2.85 (dd, J=14.4, 7.9 Hz, 1H).

4) Synthesis of (1S)-1-Carboxy-2-(7-hydroxy-2-oxo-2H-chromen-4-yl)ethyl ammonium trifluoroacetate (7)

The synthesis of the Coumarin-derivative was performed according to a known procedure in literature (M. P. Brun, L. Bischoff, C. Garbay, *Angew Chem Int Ed Engl* 2004, 43, 3432-3436).

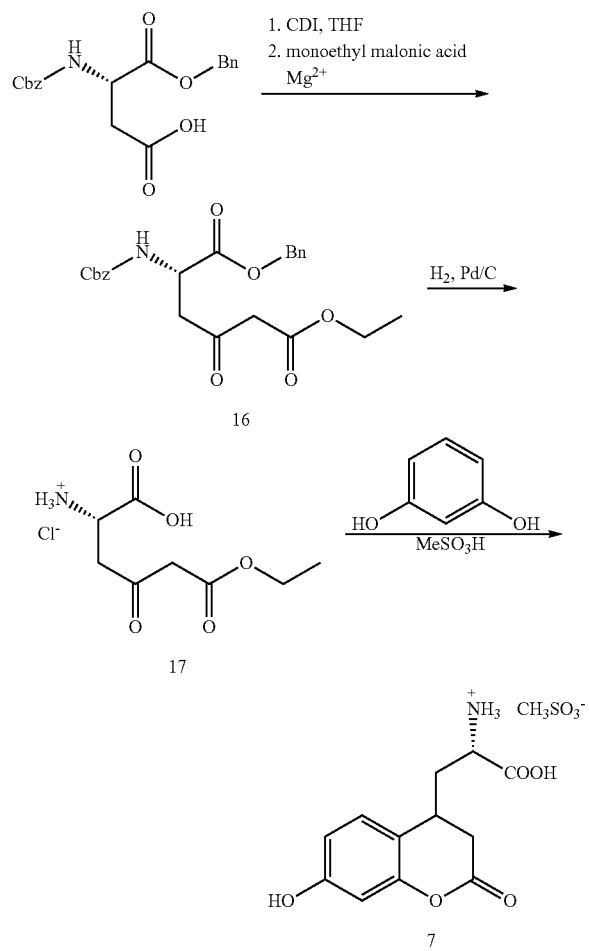

4.1) (2S)-2-Benzyloxycarbonylamino-4-oxo-hexane-dioic acid 1-benzyl ester 6-ethyl ester (16)

A solution of Cbz-(L)-Asp-OBn and carbonyldiimidazole (1.1 eq) in THF was stirred for two hours at ambient temperature, cooled to 0° C. and 0.54 eq. of monoethyl malonic acid magnesium salt was added. The mixture was stirred overnight at ambient temperature. The mixture was diluted with ether (15 mL) and acidified with conc. HCl at 0° C. and the two phases separated. The organic phase was washed with 10% $NaHCO_3$, 4:1$H_2O$: $KHSO_4$(1M), $H_2O$ and brine, dried over $MgSO_4$ and the solvent removed. A final flash purification (1:1 EtOAc:hexane) resulted in 1.67 g (70%) of compound 16 as a white solid. The analytical data matched the literature (M. P. Brun, L. Bischoff, C. Garbay, *Angew Chem Int Ed Engl* 2004, 43, 3432-3436).

4.2) (1S)-(1-Carboxy-4-ethoxycarbonyl-3-oxo-butyl) ammonium chloride (17)

Compound 2 was dissolved in 10 mL of 1:1 AcOEt:95% EtOH and 1 eq. 1N HCl and 0.05 eq. of 10% Pd on charcoal was added and stirred for 2 h at ambient temperature. The Pd was filtered off, washed with 95% EtOH and the filtrate concentrated. The residue was taken up in water an lyophilised to give 0.429 g (90%) of compound 17. The analytical data matched the literature (M. P. Brun, L. Bischoff, C. Garbay, *Angew Chem Int Ed Engl* 2004, 43, 3432-3436).

4.3) (1S)-1-Carboxy-2-(7-hydroxy-2-oxo-2H-chromen-4-yl)ethyl ammonium trifluoroacetate (7)

Compound 17 (200 mg, 0.98 mmol) and 3-hydroxyphenol (0.161 g, 1.47 mmol) were mixed and 99% methansulfonic acid (1.59 mL, 25 eq.) added at 0° C. and stirred at ambient temperature for two additional hours. The mixture was taken up in cold ether and centrifuged 20 minutes at 4000 g, the ether removed and the residue taken up in water. A final preparative HPLC (Method C) purification gave 0.136 g (40%) of Coumarin derivative 7. $^1$H-NMR (300 MHz, DMSO-$d_6$): δ 10.72 (s, 1H), 8.57-7.88 (br, 3H), 7.61 (d, J=8.7 Hz, 1H), 6.84 (dd, J=8.8, 2.4 Hz, 1H), 6.76 (d, J=2.3 Hz, 1H). 6.20 (s, 1H). 4.08 (dd, J=9.2, 5.0 Hz, 1H), 3.39 (dd, J=10.2 Hz, 1H), 3.05 (dd, J=14.6, 9.3 Hz, 1H). $^{13}$C-NMR (300 MHz, DMSO-$d_6$): 170.13, 161.70, 160.36, 155.66, 149.71, 126.39, 113.41, 111.12, 110.69. 102.96, 51.67, 32.10.

5) Synthesis of Peptide CF-Tub-Tag (18)

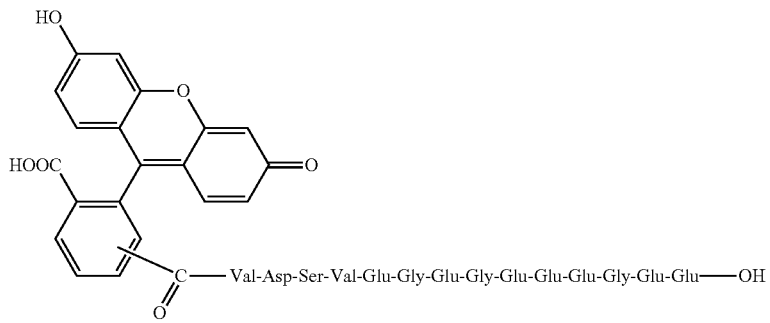

5(6)-carboxyfluorescein labelled peptide 18 (SEQ ID No. 3).

Peptide 18 (SEQ ID No. 3) was synthesized by standard Fmoc-based chemistry in a linear synthesis on an Activotec peptide synthesizer followed by manual coupling of 5(6)-carboxyfluorescein. 0.1 mmol of Fmoc-L-Glu(tBu)-Wang resin (subst: 0.58 mmol/g) was added to a reaction vessel and synthesis performed with five-fold amino acid excess. Coupling was achieved by HOBt/HBTU/DIPEA addition. After the final amino acid coupling, the fluorophore was coupled in a double coupling procedure with 5 eq of 5(6)-carboxyfluorescein, HOBt, HBTU and DIPEA in DMF for 1 h. The peptide was cleaved off the resin by addition of TFA/DTT/Tis/thioanisol (95/2/2/1) in 4 h. Subsequently, the cleavage cocktail was evaporated by $N_2$-flow and the peptide was precipitated by the addition of ice-cold diethyl ether. The precipitate was spun down, dissolved in water and acetonitrile and purified by preparative HPLC (method D). The peptide was obtained with a yield of 8% (16 mg, 8 µmol); molar mass peptide=1850.6 Da; HRMS: m/z: 926.3065 $[M+2H]^{2+}$ (calc. m/z: 926.3165).

6) TTL Expression and Purification

TTL (Canis lupus) having NCBI Accession number XP_540180.2 was expressed in *E. coli* (BL21 DE3) as Sumo-TTL fusion protein with an N-terminal His-Tag. Cells were induced with 0.5 mM IPTG and incubated at 18° C. for 18 h. Lysis was performed in presence of Lysozyme (100 µg/ml), DNAse (25 µg/ml) and PMSF (2 mM) followed by sonification (Branson® Sonifier; 16×8sec, 20% Amplitude) and debris centrifugation at 20.000 g for 30 min. His-Sumo-TTL was purified using a 5 ml His-Trap. For removal of the Sumo-Tag, peak fractions were incubated with SenP2 protease at 4° C. overnight. A second His-Trap run then removed the Sumo fraction. Purified protein was then desalted on a PD10 column (GE Healthcare); buffer was exchanged to MES/K pH 6.8 (20 mM MES, 100 mM KCl, 10 mM $MgCl_2$). Protein aliquots were shock-frozen and stored at −80° C. at 0.8 g/l.

7) GBP-Tub-Tag Expression and Purification

The expression and purification of the GBP nanobody was performed according to a previously published protocol (D. Schumacher, J. Helma, F. A. Mann, G. Pichler, F. Natale, E. Krause, M. C. Cardoso, C. P. Hackenberger, H. Leonhardt, *Angew Chem Int Ed Engl* 2015, 54, 13787-13791.). The GBP—Tub-tag fusion expression constructs was generated by standard molecular biology and was expressed in *E. coli* (JM109). Cells were induced with 0.5 mM IPTG and incubated at 18° C. for 18 h. Lysis was performed in presence of Lysozyme (100 µg/mL), DNAse (25 µg/mL) and PMSF (2 mM) followed by sonication (Branson® Sonifiers 16×8sec, 20% Amplitude) and debris centrifuged at 20.000 g for 30 min. The protein was purified with an Äkta FPLC system using a 5 mL His-Trap (GE Healthcare, USA) column, peak fractions were concentrated to 2 mL using Amicon filter columns (cut-off 3 kDa (Merck Millipore, Germany) and further purified by size exclusion chromatography (Superdex 75 column, GE Healthcare, USA). Peak fractions were pooled and protein aliquots were shock-frozen and stored at 80° C.

8) Ubiquitin-Tub-Tag Expression and Purification

The expression and purification of ubiquitin-Tub-tag was performed according to a previously published protocol (D. Schumacher, J. Helma, F. A. Mann, G. Pichler, F. Natale, E. Krause, M. C. Cardoso, C. P. Hackenberger, H. Leonhardt, *Angew Chem Int Ed Eng*/2015, 54, 13787-13791.). Proteins were expressed in *E. coli* BL21 (DE3). Cells were induced with 0.5 mM IPTG and incubated at 37° C. for 5 h. Lysis was performed using a high pressure homogenizer (Micrufluidics LM10 Microfluidizer) and debris centrifugation at 20.000 g for 30 min. The protein was purified with an NGC™ Chromatography System (BioRad, USA) using a 5 mL His,Trap (GE Healthcare, USA) column, peak fractions were concentrated to 2 mL using Amicon filter columns (cut-off 3 kDa (Merck Millipore, Germany) and futher purified by size-exclusion chromatography (Superdex 75 column, GE Healthcare, USA). Peak fractions were pooled and protein aliquots were shock-frozen and stored at,80° C.

9) Annexin V-Tub-Tag Expression and Purification

The coding sequence of Annexin V in fusion with a C-terminal Tub-tag sequence was cloned into pet22b bacterial expression vector using standard molecular biology techniques. Annexin V was expressed in *E. coli* BL21 (DE3). Cells were induced with 1 mM IPTG and incubated at 37° C. for 3 h. Lysis was performed in PBS (1.8 mM $KH_2PO_4$, 10 mM $Na_2HPO_4$, 2.7 mM KCl and 137 mM NaCl, pH 7.4) using a high-pressure homogenizer (Micrufluidics LM10 Microfluidizer) and debris centrifugation at 20.000 g for 30 min. The protein was purified with an NGC™ Chromatography System (BioRad, USA) using a 5 mL GST-Column (Bio-Scale™ Mini-Profinity™ GST, Bio-Rad, USA), protein eluted with 500 mM glutathione in PBS and peak fractions desalted and concentrated to 2 mL using Amicon filter columns (cut-off 5 kDa (Merck Millipore, Germany). Precission protease (2000 u/mL, GE Healthcare, USA) was added to the protein fractions and incubated for 16 h at 16° C. To remove the free GST, the solution was applied to another purification using 5 mL Bio-Scale Mini Profinity GST Cartridge (BioRad, USA) as described above. The flowthrough fraction was collected and concentrated to 1 mL using Vivaspin 20 (cut-off 3 kDa; Merck Millipore, Germany) and subjected to a final size exclusion chromatography in PBS using a Superdex 75 10/300 GL column (GE Healthcare, USA). Peak fractions were pooled and aliquots were shock-frozen and stored at −80° C. until further use.

10) Determination of TTL Activity Using Carboxyfluorescein-peptide (18)

Functionalization reactions were performed in a 250 µL solution consisting of 20 mM MES/K pH 7.0, 100 mM KCl, 10 mM $MgCl_2$, 2.5 mM ATP, 1 mM substrate (1-13), 0.2 mM peptide, 1 µM TTL and 5 mM DTT. The mixture was incubated at 37° C. for five hours and aliquots (25 µL) were taken, mixed with equal volumes of $H_2O$ O+0.1% TFA and subjected either to analytical HPLC (Method A) or analytical UPLC-MS analysis (Method B). Quantities of substrate and product peptides were estimated from the corresponding peak-area in the TIC or UV detection spectrum.

11) Ligation of Coumarin-Derivative (7) to Ubiquitin

Functionalization reactions were performed in a 150 µL solution consisting of 20 mM MES/K pH 7.0, 100 mM KCl, 10 mM $MgCl_2$, 2.5 mM ATP, 1 mM (7), 1 µM TTL, 5 µM ubiquitin and 5 mM DTT. The mixture was incubated at 37° for 1-6 h. Proteins were separated and analysed by SDS-PAGE and a ChemiDoc™ XRS+gel imaging system (Bio-Rad, Hercules, Calif., US).

12) Ligation of Coumarin-Derivative 7 GBP

Functionalization reactions were performed in a 150 µL solution consisting of 20 mM MES/K pH 7.0, 100 mM KCl, 10 mM $MgCl_2$, 2.5 mM ATP, 1 mM (7), 1 µM TTL, 5 µM nanobody and 5 mM DTT. The mixture was incubated at 37° for 1-6 h. Proteins were separated and analysed by SDS-PAGE and a ChemiDoc™ XRS+gel imaging system (Bio-Rad, Hercules, Calif., US).

13) Ligation of Coumarin-Derivative 7 to Annexin V

Functionalization reactions were performed in a 150 µL solution consisting of 20 mM MES/K pH 7.0, 100 mM KCl, 10 mM $MgCl_2$, 2.5 mM ATP, 1 mM (24), 1 µM TTL, 5 µM nanobody and 5 mM DTT. The mixture was incubated at 37° for 1-6 h. Proteins were separated and analysed by SDS-PAGE and a ChemiDoc™ XRS+gel imaging system (Bio-Rad, Hercules, Calif., US).

14) Immunostaining

Coumarin-functionalized GFP binding nanobody (GBP-Coumarin) was used for immunostaining. First, HeLa cells were seeded on coverslips in 6-well plates (Greiner, Germany), transfected with plasmids encoding GFP-PCNA (H. Leonhardt, H. P. Rahn, P. Weinzierl, A. Sporbert, T. Cremer, D. Zink, M. C. Cardoso, *J Cell Biol* 2000, 149, 271-280.), GFP-Dnmt1 (H. P. Easwaran, L. Schermelleh, H. Leonhardt, M. C. Cardoso, *EMBO Rep* 2004, 5, 1181-1186.) and GFP-LaminB1 (N. Daigle, J. Beaudouin, L. Hartnell, G. lmreh, E. Hallberg, J. Lippincott-Schwartz, J. Ellenberg, *J Cell Biol* 2001, 154, 71-84.) using lipofectamine transfection reagent (Life Technologies). 24 h after transfection, cells were fixed with 4% paraformaldehyde (Sigma, Germany), permeabilized with Triton $X_{100}$ (Roth, Germany) and blocked with 2% BSA (Roth, Germany). Coverslips were then incubated with 1 µg GBP-Coumarin for 1 h and counterstained with DAPI. Samples were then subjected to fluorescence microscopy using a Leica SP5 confocal microscope.

15) Annexin V Staining

~$2 \times 10^4$ cells/well were seeded in a 96-well µclear plate (Greiner, Austria). Following 3 h induction of apoptosis with 5 µM Staurosporine (Sigma-Aldrich, UK), cells were stained with either commercial AnnexinV_Alexa350 (5 µg/$1 \times 10^5$ cells) or Coumarin-functionalized Annexin V (5 µg/$1 \times 10^5$ cells). Cells were fixed in 3.7% formaldehyde in PBS for 10 min at RT, washed with PBS-T and permeabilized with 0.5% Triton X-100 (neoLab Laborbedarf, Germany) for 10 min. Cells were counterstained with Propidium Iodide at 100 µg/ml (Sigma-Aldrich, UK) for 10 min in the dark and followed by repeated washing with PBS-T.

16) Microscopy

Confocal Imaging was carried out with a Leica SP5 II confocal point scanner (Leica Microsystems, Germany). Image acquisition was performed with a 60x/1.4,0.6 NA Planapo-chromat oil immersion objective lens. To visualize Coumarin and GFP the 405 and 488 nm excitation lasers were used, respectively. Microscopic analysis of apoptotic cells, visualized by Annexin V was performed with an Operetta high-content imaging platform (Perkin Elmer, USA). Propidium iodide and Coumarin/Alexa350 were detected using the preset DsRed and DAPI filter combinations.

17) Discussion

In order to elucidate whether tubulin tyrosine ligase accepts compounds as substrate that are structurally unrelated to tyrosine (FIG. 1), ligation experiments have been performed using a 5,6-carboxyfluorescein-labeled peptide that mimics the TTL recognition motif (CF-Tub-tag peptide 18). compounds 1-13 were co-incubated as substrates (FIG. 2) and the reaction process of each substrate after five hours of incubation time analysed by UPLC-MS and HPLC analysis (FIGS. 3 and 4). Surprisingly, the amino acids leucine (FIG. 3*a*), histidine (FIG. 3*b*), methionine (FIG. 3*c*) and tryptophan (FIG. 3*d*) were ligated to peptide 18 by TTL (yields: 3-75%). Moreover, derivatives of tryptophan (FIG. 3*e-j*) and coumarin amino acids (FIG. 3*k*), azulenyl amino acids (FIG. 3*m*) as well as esterified amino acids (FIG. 4) were tolerated, too (yields: 5-73%). These findings are in particular unexpected, since enzymes usually are very limited in respect to their substrate scope. Subsequently, the reactivity of substrates 5, 7 and 11 where further analysed and product formation quantified at different time points (FIG. 5-7). Encouraged by these results, it was tested whether this concept can be transferred for the site-specific labelling of functional proteins. The Tub-tag sequence (VDSVEGEGEEEGEE) was fused to the C-terminus of ubiquitin, to a GFP-specific single domain nanobody (GBP) as well as the apoptosis marker Annexin V and TTL mediated labelling experiments were performed with the fluorescent compound 7. Both proteins were successfully functionalized with the fluorescent coumarin derivative 7 as analysed by SDS-PAGE and in-gel fluorescence analysis (ubiquitin FIG. 8, GBP FIG. 9, Annexin V FIG. 10). Subsequently it was studied, whether the site-specifically labelled GBP can be used to immunostain cellular proteins and structures. Hela cells expressing GFP-PCNA (H. Leonhardt, H. P. Rahn, P. Weinzierl, A. Sporbert, T. Cremer, D. Zink, M. C. Cardoso, *J Cell Biol* 2000, 149, 271-280.), GFP-Lamin (N. Daigle, J. Beaudouin, L. Hartnell, G. lmreh, E. Hallberg, J. Lippincott-Schwartz, J. Ellenberg, *J Cell Biol* 2001, 154, 71-84.) and GFP-Dnmt1 (H. P. Easwaran, L. Schermelleh, H. Leonhardt, M. C. Cardoso, *EMBO Rep* 2004, 5, 1181-1186.) were fixed and co-incubated with GBP functionalized with compound 7 (GBP-Coumarin). Confocal microscopy revealed high colocalization of GBP-Coumarin with GFP-Dnmt1 (FIG. 7*a*), GFP-PCNA (FIG. 7*b*) and GFP-Lamin (FIG. 7*c*). Finally, we used Tub-tagged Annexin V functionalized with coumarin 7 for detection of apoptotic cells. Annexin V is an endogenous human protein used as a marker for apoptosis. Annexin V strongly binds to phosphatidylserine, a phospholipid present in the cell membrane, that flips from the cytosolic to the extracellular surface upon apoptosis during programmed cell death. For in vivo use of Annexin V, the site-specific and controlled attachment of probes is highly important. After chemical induction of apoptosis with 5 µM Staurosporine, apoptotic cells were visualized with coumarin-labeled Annexin V in comparable quality to a commercial probe (FIG. 12).

It will be clear that the invention may be practiced otherwise than as particularly described in the foregoing description and examples. Numerous modifications and variations of the present invention are possible in light of the above teachings and, therefore, are within the scope of the appended claims.

The invention claimed is:

1. A method for the production of a functionalized polypeptide comprising (a) introducing or adding at the C-terminus of a polypeptide a recognition sequence for tubulin tyrosine ligase, wherein said polypeptide is a polypeptide other than tubulin;

(b) contacting the polypeptide obtained in step (a) in the presence of tubulin tyrosine ligase and a compound under conditions suitable for the tubulin tyrosine ligase to functionalize said polypeptide with said compound, wherein said compound having a structure according to Formula I

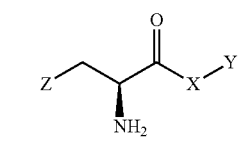

wherein
X is O, NR¹ or S;
Y is selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl;

Z is selected from the group consisting of substituted or unsubstituted alkyl, substituted or unsubstituted alkenyl, substituted or unsubstituted alkynyl, substituted or unsubstituted cycloalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, substituted or unsubstituted heteroalkyl, substituted or unsubstituted heteroalkenyl and substituted or unsubstituted heteroalkynyl; and $R^1$ is selected from the group consisting of hydrogen, substituted or unsubstituted $(C_1$-$C_6)$alkyl, substituted or unsubstituted $(C_2$-$C_6)$alkenyl, substituted or unsubstituted $(C_2$-$C_6)$alkynyl, substituted or unsubstituted $(C_3$-$C_8)$cycloalkyl, substituted or unsubstituted $(C_6$-$C_{14})$aryl and substituted or unsubstituted $(C_3$-$C_{14})$heteroaryl;

with the proviso that Z is not a substituted or unsubstituted monocyclic six-membered aryl;

wherein the recognition sequence for tubulin tyrosine ligase has at least the amino acid sequence $X_1X_2X_3X_4$ (SEQ ID No: 9), wherein $X_1$ and $X_2$ is any amino acid, $X_3$ is E, D or C, and $X_4$ is E.

2. The method of claim 1, further comprising
(c) conjugating a moiety to said functionalized polypeptide obtained in step (b).

3. The method of claim 1, wherein the compound having a structure according to formula I is characterized in that,
X is O, $NR^1$ or S;
Y is hydrogen or substituted or unsubstituted $(C_1$-$C_6)$alkyl;
Z is selected from the group consisting of substituted or unsubstituted $(C_1$-$C_6)$alkyl, substituted or unsubstituted $(C_2$-$C_6)$alkenyl, substituted or unsubstituted $(C_2$-$C_6)$alkynyl, substituted or unsubstituted $(C_3$-$C_5)$cycloalkyl, substituted or unsubstituted $(C_7$-$C_{14})$aryl, substituted or unsubstituted $(C_6$-$C_{14})$aryl$(C_1$-$C_6)$alkyl, substituted or unsubstituted $(C_3$-$C_{14})$heteroaryl, substituted or unsubstituted $(C_3$-$C_{14})$heteroaryl$(C_1$-$C_6)$alkyl, substituted or unsubstituted $(C_3$-$C_{14})$heterocyclyl, substituted or unsubstituted $(C_1$-$C_6)$heteroalkyl, substituted or unsubstituted $(C_2$-$C_6)$heteroalkenyl and substituted or unsubstituted $(C_2$-$C_6)$heteroalkynyl; and
$R^1$ is hydrogen or substituted or unsubstituted $(C_1$-$C_6)$alkyl.

4. The method of claim 1, wherein $X_2$ is G, S, A, V, or F.

5. The method of claim 1, wherein the recognition sequence is EGEE (SEQ ID No. 2), VDSVEGEGEEEGEE (SEQ ID No. 3), SVEGEGEEEGEE (SEQ ID No. 4), SADGEDEGEE (SEQ ID No. 5), SVEAEAEEGEE (SEQ ID No. 6), SYEDEDEGEE (SEQ ID No. 7), or SFEEENEGEE (SEQ ID No. 8).

6. The method of claim 1, wherein said polypeptide comprises a linker sequence preceding the recognition sequence of tubulin tyrosine ligase.

7. The method of claim 2, wherein said moiety conjugated to a functionalized polypeptide is a carrier, a polypeptide, a detectable label, a nucleic acid, a carbohydrate, or a lipid.

8. The method of claim 7, wherein the polypeptide moiety is an antibody or fragment thereof selected from the group consisting of a monoclonal antibody, chimeric antibody, humanized antibody, human antibody, scFv, a DART, domain antibody, nanobody, an adnectin, an affibody, an anticalin, a DARPin, or an aptamer.

9. The method of claim 7, wherein the detectable label comprises a fluorophore, an enzyme, a radioisotope, a fluorescent protein, or a fluorescent dye.

10. The method of claim 7, wherein the nucleic acid is DNA, RNA, or an aptamer.

11. The method of claim 1, wherein the suitable conditions comprise a buffer containing a nucleoside triphosphate potassium chloride, magnesium chloride, a reducing agent.

12. The method of claim 1, wherein the suitable conditions further comprise a pH-value in the range of 5 to 9.

13. The method of claim 1, wherein the suitable conditions further comprise a concentration of the compound having a structure according to formula I in the range of 0.1 mM to 10 mM.

14. The method of claim 1, wherein the suitable conditions further comprise a reaction temperature in the range of 1° C. to 70° C., or a reaction temperature in the range of 19° C. to 37° C.

15. The method of claim 1, wherein the suitable conditions further comprise a reaction time in the range of 5 minutes to 4 hours, or a reaction time in the range of 1 hour to 3 hours.

16. The method of claim 1, wherein said polypeptide has a length of more than 19 amino acids.

17. The method of claim 1, wherein the compound having a structure according to formula I is characterized in that,
X is O, $NR^1$ or S;
Y is hydrogen or substituted or unsubstituted $(C_1$-$C_6)$alkyl;
Z is selected from the group consisting of substituted or unsubstituted 2H-1-benzopyranyl (2H-chromenyl), substituted or unsubstituted benzodihydropyranyl (chromanyl), substituted or unsubstituted 4H-1-benzopyranyl (4H-chromenyl), substituted or unsubstituted 1H-2-benzopyranyl (1H-isochromenyl), substituted or unsubstituted isochromanyl, substituted or unsubstituted 3H-2-benzopyranyl (3H-isochromenyl), substituted or unsubstituted 1-benzopyran-4-on-yl (chromonyl), substituted or unsubstituted 4-chromanonyl, substituted or unsubstituted 1-benzopyran-2-on-yl (coumarinyl), substituted or unsubstituted dihydrocoumarinyl, substituted or unsubstituted 3-isochromanonyl, substituted or unsubstituted 2-coumaranonyl, substituted or unsubstituted $(C_1$-$C_6)$alkyl, substituted or unsubstituted $(C_1$-$C_6)$heteroalkyl, substituted or unsubstituted imidazolyl, substituted or unsubstituted azaindolyl including 7-azaindolyl, 6-azaindolyl, 5-azaindolyl and 4-azaindolyl and substituted or unsubstituted indolyl; and
$R^1$ is hydrogen or substituted or unsubstituted $(C_1$-$C_6)$alkyl.

18. The method of claim 2, wherein said moiety conjugated to a functionalized polypeptide is a chemical compound.

19. The method of claim 9, wherein the enzyme is a peroxidase or a luciferase.

20. The method of claim 11, wherein the nucleoside triphosphate is ATP.

21. The method of claim 11, wherein the reducing agent is DTT.

22. The method of claim 4, wherein $X_1$ is E, D, A, K, or P.

23. The method of claim 18, wherein said chemical compound is a small molecule, a polymer, or a therapeutic agent.

24. The method of claim 23, wherein the polymer is a synthetic polymer.

25. The method of claim 24, wherein the synthetic polymer is PEG.

\* \* \* \* \*

SEQUENCE LISTING

<160> NUMBER OF SEQ ID NOS: 10

<210> SEQ ID NO 1
<211> LENGTH: 450
<212> TYPE: PRT
<213> ORGANISM: Homo sapiens

<400> SEQUENCE: 1

```
Met Arg Glu Cys Ile Ser Ile His Val Gly Gln Ala Gly Val Gln Ile
1               5                  10                   15

Gly Asn Ala Cys Trp Glu Leu Tyr Cys Leu Glu His Gly Ile Gln Pro
            20                  25                  30

Asp Gly Gln Met Pro Ser Asp Lys Thr Ile Gly Gly Gly Asp Asp Ser
        35                  40                  45

Phe Asn Thr Phe Phe Ser Glu Thr Gly Ala Gly Lys His Val Pro Arg
    50                  55                  60

Ala Val Phe Val Asp Leu Glu Pro Thr Val Ile Asp Glu Val Arg Thr
65                  70                  75                  80

Gly Thr Tyr Arg Gln Leu Phe His Pro Glu Gln Leu Ile Thr Gly Lys
                85                  90                  95

Glu Asp Ala Ala Asn Asn Tyr Ala Arg Gly His Tyr Thr Ile Gly Lys
            100                 105                 110

Glu Ile Ile Asp Leu Val Leu Asp Arg Ile Arg Lys Leu Ala Asp Gln
        115                 120                 125

Cys Thr Gly Leu Gln Gly Phe Leu Val Phe His Ser Phe Gly Gly Gly
    130                 135                 140

Thr Gly Ser Gly Phe Thr Ser Leu Leu Met Glu Arg Leu Ser Val Asp
145                 150                 155                 160

Tyr Gly Lys Lys Ser Lys Leu Glu Phe Ser Ile Tyr Pro Ala Pro Gln
                165                 170                 175

Val Ser Thr Ala Val Val Glu Pro Tyr Asn Ser Ile Leu Thr Thr His
            180                 185                 190

Thr Thr Leu Glu His Ser Asp Cys Ala Phe Met Val Asp Asn Glu Ala
        195                 200                 205

Ile Tyr Asp Ile Cys Arg Arg Asn Leu Asp Ile Glu Arg Pro Thr Tyr
    210                 215                 220

Thr Asn Leu Asn Arg Leu Ile Gly Gln Ile Val Ser Ser Ile Thr Ala
225                 230                 235                 240

Ser Leu Arg Phe Asp Gly Ala Leu Asn Val Asp Leu Thr Glu Phe Gln
                245                 250                 255

Thr Asn Leu Val Pro Tyr Pro Arg Ile His Phe Pro Leu Ala Thr Tyr
            260                 265                 270

Ala Pro Val Ile Ser Ala Glu Lys Ala Tyr His Glu Gln Leu Ser Val
        275                 280                 285

Ala Glu Ile Thr Asn Ala Cys Phe Glu Pro Ala Asn Gln Met Val Lys
    290                 295                 300

Cys Asp Pro Arg His Gly Lys Tyr Met Ala Cys Cys Leu Leu Tyr Arg
305                 310                 315                 320

Gly Asp Val Val Pro Lys Asp Val Asn Ala Ala Ile Ala Thr Ile Lys
                325                 330                 335

Thr Lys Arg Thr Ile Gln Phe Val Asp Trp Cys Pro Thr Gly Phe Lys
            340                 345                 350

Val Gly Ile Asn Tyr Gln Pro Pro Thr Val Val Pro Gly Gly Asp Leu
        355                 360                 365
```

```
Ala Lys Val Gln Arg Ala Val Cys Met Leu Ser Asn Thr Thr Ala Ile
        370                 375                 380

Ala Glu Ala Trp Ala Arg Leu Asp His Lys Phe Asp Leu Met Tyr Ala
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Met Ala Ala Leu Glu Lys Asp Tyr
            420                 425                 430

Glu Glu Val Gly Val Asp Ser Val Glu Gly Glu Gly Glu Glu Glu Gly
                435                 440                 445

Glu Glu
    450

<210> SEQ ID NO 2
<211> LENGTH: 4
<212> TYPE: PRT
<213> ORGANISM: artificial
<220> FEATURE:
<223> OTHER INFORMATION: TTL recognition sequence

<400> SEQUENCE: 2

Glu Gly Glu Glu
1

<210> SEQ ID NO 3
<211> LENGTH: 14
<212> TYPE: PRT
<213> ORGANISM: artificial
<220> FEATURE:
<223> OTHER INFORMATION: TTL recognition sequence

<400> SEQUENCE: 3

Val Asp Ser Val Glu Gly Glu Gly Glu Glu Gly Glu Glu
1               5                   10

<210> SEQ ID NO 4
<211> LENGTH: 12
<212> TYPE: PRT
<213> ORGANISM: artificial
<220> FEATURE:
<223> OTHER INFORMATION: TTL recognition sequence

<400> SEQUENCE: 4

Ser Val Glu Gly Glu Gly Glu Glu Gly Glu Glu
1               5                   10

<210> SEQ ID NO 5
<211> LENGTH: 10
<212> TYPE: PRT
<213> ORGANISM: artificial
<220> FEATURE:
<223> OTHER INFORMATION: TTL recognition sequence

<400> SEQUENCE: 5

Ser Ala Asp Gly Glu Asp Glu Gly Glu Glu
1               5                   10

<210> SEQ ID NO 6
<211> LENGTH: 11
<212> TYPE: PRT
<213> ORGANISM: artificial
<220> FEATURE:
<223> OTHER INFORMATION: TTL recognition sequence

<400> SEQUENCE: 6
```

```
Ser Val Glu Ala Glu Ala Glu Gly Glu Glu
1               5                   10

<210> SEQ ID NO 7
<211> LENGTH: 10
<212> TYPE: PRT
<213> ORGANISM: artificial
<220> FEATURE:
<223> OTHER INFORMATION: TTL recognition sequence

<400> SEQUENCE: 7

Ser Tyr Glu Asp Glu Asp Glu Gly Glu Glu
1               5                   10

<210> SEQ ID NO 8
<211> LENGTH: 10
<212> TYPE: PRT
<213> ORGANISM: artificial
<220> FEATURE:
<223> OTHER INFORMATION: TTL recognition sequence

<400> SEQUENCE: 8

Ser Phe Glu Glu Glu Asn Glu Gly Glu Glu
1               5                   10

<210> SEQ ID NO 9
<211> LENGTH: 4
<212> TYPE: PRT
<213> ORGANISM: artificial
<220> FEATURE:
<223> OTHER INFORMATION: TTL recognition sequence
<220> FEATURE:
<221> NAME/KEY: misc
<222> LOCATION: (1)..(1)
<223> OTHER INFORMATION: X can be any amino acid
<220> FEATURE:
<221> NAME/KEY: misc
<222> LOCATION: (2)..(2)
<223> OTHER INFORMATION: X can be any amino acid
<220> FEATURE:
<221> NAME/KEY: misc
<222> LOCATION: (3)..(3)
<223> OTHER INFORMATION: X can be E, D or C
<220> FEATURE:
<221> NAME/KEY: misc
<222> LOCATION: (4)..(4)
<223> OTHER INFORMATION: X can be E

<400> SEQUENCE: 9

Xaa Xaa Xaa Xaa
1

<210> SEQ ID NO 10
<211> LENGTH: 377
<212> TYPE: PRT
<213> ORGANISM: Homo sapiens

<400> SEQUENCE: 10

Met Tyr Thr Phe Val Val Arg Asp Glu Asn Ser Ser Val Tyr Ala Glu
1               5                   10                  15

Val Ser Arg Leu Leu Leu Ala Thr Gly His Trp Lys Arg Leu Arg Arg
            20                  25                  30

Asp Asn Pro Arg Phe Asn Leu Met Leu Gly Glu Arg Asn Arg Leu Pro
        35                  40                  45

Phe Gly Arg Leu Gly His Glu Pro Gly Leu Val Gln Leu Val Asn Tyr
    50                  55                  60
```

-continued

```
Tyr Arg Gly Ala Asp Lys Leu Cys Arg Lys Ala Ser Leu Val Lys Leu
 65                  70                  75                  80

Ile Lys Thr Ser Pro Glu Leu Ala Glu Ser Cys Thr Trp Phe Pro Glu
                 85                  90                  95

Ser Tyr Val Ile Tyr Pro Thr Asn Leu Lys Thr Pro Val Ala Pro Ala
            100                 105                 110

Gln Asn Gly Ile Gln Pro Pro Ile Ser Asn Ser Arg Thr Asp Glu Arg
            115                 120                 125

Glu Phe Phe Leu Ala Ser Tyr Asn Arg Lys Lys Glu Asp Gly Glu Gly
        130                 135                 140

Asn Val Trp Ile Ala Lys Ser Ser Ala Gly Ala Lys Gly Glu Gly Ile
145                 150                 155                 160

Leu Ile Ser Ser Glu Ala Ser Glu Leu Leu Asp Phe Ile Asp Asn Gln
                165                 170                 175

Gly Gln Val His Val Ile Gln Lys Tyr Leu Glu His Pro Leu Leu Leu
            180                 185                 190

Glu Pro Gly His Arg Lys Phe Asp Ile Arg Ser Trp Val Leu Val Asp
            195                 200                 205

His Gln Tyr Asn Ile Tyr Leu Tyr Arg Glu Gly Val Leu Arg Thr Ala
            210                 215                 220

Ser Glu Pro Tyr His Val Asp Asn Phe Gln Asp Lys Thr Cys His Leu
225                 230                 235                 240

Thr Asn His Cys Ile Gln Lys Glu Tyr Ser Lys Asn Tyr Gly Lys Tyr
                245                 250                 255

Glu Glu Gly Asn Glu Met Phe Phe Lys Glu Phe Asn Gln Tyr Leu Thr
            260                 265                 270

Ser Ala Leu Asn Ile Thr Leu Glu Ser Ser Ile Leu Leu Gln Ile Lys
            275                 280                 285

His Ile Ile Arg Asn Cys Leu Leu Ser Val Glu Pro Ala Ile Ser Thr
            290                 295                 300

Lys His Leu Pro Tyr Gln Ser Phe Gln Leu Phe Gly Phe Asp Phe Met
305                 310                 315                 320

Val Asp Glu Glu Leu Lys Val Trp Leu Ile Glu Val Asn Gly Ala Pro
                325                 330                 335

Ala Cys Ala Gln Lys Leu Tyr Ala Glu Leu Cys Gln Gly Ile Val Asp
            340                 345                 350

Ile Ala Ile Ser Ser Val Phe Pro Pro Asp Val Glu Gln Pro Gln
            355                 360                 365

Thr Gln Pro Ala Ala Phe Ile Lys Leu
370                 375
```

UNITED STATES PATENT AND TRADEMARK OFFICE
CERTIFICATE OF CORRECTION

PATENT NO. : 11,572,384 B2  
APPLICATION NO. : 16/096787  
DATED : February 7, 2023  
INVENTOR(S) : Christian Hackenberger et al.

Page 1 of 1

It is certified that error appears in the above-identified patent and that said Letters Patent is hereby corrected as shown below:

On the Title Page

Item [73]:
"Ludwig-Mavimilians-Universität München, Munich (DE)"
Should read:
--Ludwig-Maximilians-Universität München, Munich (DE)--.

In the Claims

Column 81, Claim 3, Lines 40-41:
"$(C_3-C_5)$cycloalkyl,"
Should read:
--$(C_3-C_8)$cycloalkyl,--.

Signed and Sealed this  
Seventh Day of January, 2025

Derrick Brent  
*Acting Director of the United States Patent and Trademark Office*